United States Patent
Lu et al.

(10) Patent No.: US 12,077,538 B2
(45) Date of Patent: *Sep. 3, 2024

(54) DIACYLGLYCEROL KINASE (DGK) ALPHA INHIBITORS AND USES THEREOF

(71) Applicant: Insilico Medicine IP Limited, Hong Kong (HK)

(72) Inventors: Hongfu Lu, Shanghai (CN); Huaxing Yu, Shanghai (CN); Xiao Ding, Shanghai (CN); Feng Ren, Shanghai (CN)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 18/507,595

(22) Filed: Nov. 13, 2023

(65) Prior Publication Data

US 2024/0116935 A1 Apr. 11, 2024

Related U.S. Application Data

(63) Continuation of application No. PCT/CN2023/078948, filed on Mar. 1, 2023.

(30) Foreign Application Priority Data

| | | |
|---|---|---|
| Mar. 1, 2022 | (WO) | PCT/CN2022/078653 |
| May 7, 2022 | (WO) | PCT/CN2022/091497 |
| Oct. 24, 2022 | (WO) | PCT/CN2022/127020 |
| Jan. 12, 2023 | (WO) | PCT/CN2023/071857 |

(51) Int. Cl.
*C07D 471/04* (2006.01)

(52) U.S. Cl.
CPC ................ *C07D 471/04* (2013.01)

(58) Field of Classification Search
None
See application file for complete search history.

(56) References Cited

U.S. PATENT DOCUMENTS

| | | | |
|---|---|---|---|
| 5,846,514 A | 12/1998 | Foster et al. | |
| 6,334,997 B1 | 1/2002 | Foster et al. | |
| 7,173,036 B2 | 2/2007 | Sircar et al. | |
| 2021/0188845 A1 | 6/2021 | Gentles et al. | |
| 2024/0051958 A1 | 2/2024 | Lu et al. | |

FOREIGN PATENT DOCUMENTS

| | | |
|---|---|---|
| WO | WO-2004081008 A1 | 9/2004 |
| WO | WO-2006032470 A1 | 3/2006 |
| WO | WO-2008075109 A1 | 6/2008 |
| WO | WO-2011075747 A1 | 6/2011 |
| WO | WO-2017019723 A1 | 2/2017 |
| WO | WO-2019141153 A1 | 7/2019 |
| WO | WO-2020006016 A1 | 1/2020 |
| WO | WO-2020006018 A1 | 1/2020 |
| WO | WO-2021001453 A1 | 1/2021 |
| WO | WO-2021041588 A1 | 3/2021 |
| WO | WO-2021074365 A1 | 4/2021 |
| WO | WO-2021105115 A1 | 6/2021 |
| WO | WO-2021105116 A1 | 6/2021 |
| WO | WO-2021105117 A1 | 6/2021 |
| WO | WO-2021127554 A1 | 6/2021 |
| WO | WO-2021130638 A1 | 7/2021 |
| WO | WO-2021133748 A1 | 7/2021 |
| WO | WO-2021133749 A1 | 7/2021 |
| WO | WO-2021133750 A1 | 7/2021 |
| WO | WO-2021133751 A1 | 7/2021 |
| WO | WO-2021133752 A1 | 7/2021 |
| WO | WO-2021258010 A1 | 12/2021 |
| WO | WO-2022133083 A1 | 6/2022 |
| WO | WO-2022271650 A1 | 12/2022 |
| WO | WO-2022271659 A1 | 12/2022 |
| WO | WO-2022271677 A1 | 12/2022 |
| WO | WO-2022271684 A1 | 12/2022 |
| WO | WO-2023011456 A1 | 2/2023 |
| WO | WO-2023165504 A1 | 9/2023 |
| WO | WO-2023165509 A1 | 9/2023 |
| WO | WO-2023165525 A1 | 9/2023 |
| WO | WO-2023165528 A1 | 9/2023 |
| WO | WO-2023184327 A1 | 10/2023 |
| WO | WO-2023186060 A1 | 10/2023 |

OTHER PUBLICATIONS

Dominguez. Cancer Discovery, 2013, 3(7), 782-797 (Year: 2013).*
Zhong. Nature Immunology, 2003, 4(9), 882-890 (Year: 2003).*
Co-pending U.S. Appl. No. 18/486,374, inventors Lu; Hongfu et al., filed Oct. 13, 2023.
De Fusco et al. Fragment-Based Design of a Potent MAT2a Inhibitor and in VivoEvaluation in an MTAP Null Xenograft Model. J Med Chem 64:6814-6826 (2021).
Deng et al. Synthesis and anticonvulsant activity of 5-substituted-[1,2,4]triazolo[4,3-a]quinazolines. Chinese Journal of Organic Chemistry 31(12):2082 (2011) (English Abstract).
PCT/CN2023/078948 International Search Report and Written Opinion dated May 29, 2023.
PCT/CN2023/078973 International Search Report and Written Opinion dated Jun. 13, 2023.
PCT/CN2023/079062 International Search Report and Written Opinion dated Apr. 21, 2023.
PCT/CN2023/079066 International Search Report and Written Opinion dated Apr. 21, 2023.

* cited by examiner

*Primary Examiner* — Noble E Jarrell
(74) *Attorney, Agent, or Firm* — WILSON SONSINI GOODRICH & ROSATI

(57) ABSTRACT

Described herein are DGKalpha inhibitors and pharmaceutical compositions comprising said inhibitors. The subject compounds and compositions are useful for the treatment of a disease or disorder associated with DGKalpha.

20 Claims, No Drawings

DIACYLGLYCEROL KINASE (DGK) ALPHA INHIBITORS AND USES THEREOF

CROSS-REFERENCE

This application is a continuation of International Application No. PCT/CN2023/078948, filed Mar. 1, 2023, which claims the benefit of International Application No. PCT/CN2022/078653, filed Mar. 1, 2022; International Application No. PCT/CN2022/091497, filed May 7, 2022; International Application No. PCT/CN2022/127020, filed Oct. 24, 2022; and International Application No. PCT/CN2023/071857, filed Jan. 12, 2023; which are incorporated herein by reference in their entirety.

BACKGROUND

Diacylglycerol kinases (DGKs) represent a family of enzymes that catalyze phosphorylation of the membrane lipid sn-1,2 diacylglycerol (DAG) to form phosphatidic acid (PA). In T cells, DAG is formed downstream of the T cell receptor (TCR) after activation of the gamma 1 isoform of phospholipase C (PLCyl) and cleavage of phosphatidylinositol 4,5-biphosphate (PIP2) into DAG and an additional second messenger, inositol 1,4,5-triphosphate (IP3). Whereas, IP3 is important in facilitating release of calcium from the endoplasmic reticulum, DAG interacts with other proteins important in TCR signal transduction, such as Protein kinase CO and the Ras activating protein RasGRPI. Although, three isoforms of DGK are known to be present within T cells (DGKalpha, DGKdelta, and DGKzeta), only two, DGKalpha and DGKzeta, are thought to play an important role in facilitating DAG metabolism downstream of the TCR.

Supporting evidence include knock-out mouse models of either DGKalpha or DGKzeta which show a hyper-responsive T cell phenotype and improved anti-tumor immune activity (Riese M. J. et al., Journal of Biological Chemistry, (2011) 7: 5254-5265; Zha Y et al., Nature Immunology, (2006) 12:1343; Olenchock B. A. et al., (2006) 11: 1174-81). Furthermore tumor infiltrating lymphocytes isolated from human renal cell carcinoma patients were observed to overexpress DGKalpha which resulted in inhibited T cell function (Prinz, P. U. et al., J Immunology (2012) 12:5990-6000). Thus, DGKalpha and DGKzeta are viewed as targets for cancer immunotherapy (Riese M. J. et al., Front Cell Dev Biol. (2016) 4: 108; Chen, S. S. et al., Front Cell Dev Biol. (2016) 4: 130; Avila-Flores, A. et al., Immunology and Cell Biology (2017) 95: 549-563; Noessner, E., Front Cell Dev Biol. (2017) 5: 16; Krishna, S., et al., Front Immunology (2013) 4:178; Jing, W. et al., Cancer Research (2017) 77: 5676-5686. There remains a need for compounds useful as inhibitors of one or both of DGKalpha and DGKzeta, especially compounds that have selectivity over other diacylglycerol kinases, protein kinases, and/or other lipid kinases. There remains a need for compounds that are safe and effective in restoring T cell activation, lowering antigen threshold, enhancing antitumor functionality, and/or overcoming the suppressive effects of one or more endogenous immune checkpoints, such as PD-1, PD-L1, and CTLA-4, would be an important addition for the treatment of patients with proliferative disorders, such as cancer, as well as a viral infections.

SUMMARY

Disclosed herein is a compound of Formula (I), or a pharmaceutically acceptable salt thereof:

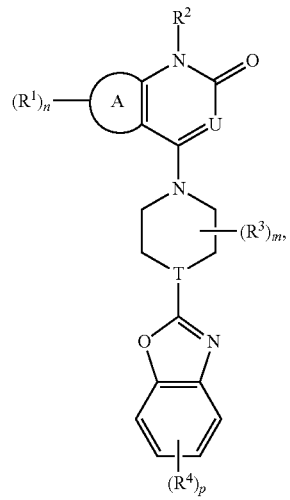

Formula (I)

wherein:
Ring A is phenyl or 6-membered heteroaryl;
each $R^1$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;
n is 0-4;
$R^2$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl;
U is N or CR$^U$;
$R^U$ is hydrogen, halogen, —OH, —OR$^a$, —NR$^c$R$^d$, —C(=O)R$^a$, —C(=O)OR$^b$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;
each $R^3$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;
or two $R^3$ on the same atom are taken together to form an oxo;

or two R³ on adjacent carbons are taken together to form an alkenylene;

or two R³ on the same or different carbons are taken together to form a cycloalkyl or heterocycloalkyl, each optionally substituted with one or more R;

m is 0-8;

T is N or CR$^T$;

R$^T$ is hydrogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;

each R⁴ is independently halogen, —CN, —NO₂, —OH, —OR$^a$, —OC(=O)R$^a$, —OC(=O)OR$^b$, —OC(=O)NR$^c$R$^d$, —SH, —SR$^a$, —S(=O)R$^a$, —S(=O)₂R$^a$, —S(=O)₂NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)₂R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

p is 0-4;

each R$^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

or two R$^a$ are taken together with the atom to which they are attached to form a heterocycloalkyl optionally substituted with one or more R;

each R$^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

or two R$^b$ are taken together with the atom to which they are attached to form a heterocycloalkyl optionally substituted with one or more R;

R$^c$ and R$^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

or R$^c$ and R$^d$ are taken together with the atom to which they are attached to form a heterocycloalkyl optionally substituted with one or more R; and each R is independently halogen, —CN, —OH, —S(=O)CH₃, —S(=O)₂CH₃, —S(=O)₂NH₂, —S(=O)₂NHCH₃, —S(=O)₂N(CH₃)₂, —NH₂, —NHCH₃, —N(CH₃)₂, —C(=O)CH₃, —C(=O)OH, —C(=O)OCH₃, $C_1$-$C_6$alkyl, $C_1$-$C_6$alkoxy, $C_1$-$C_6$haloalkyl, $C_1$-$C_6$hydroxyalkyl, $C_1$-$C_6$aminoalkyl, $C_1$-$C_6$heteroalkyl, or $C_3$-$C_6$cycloalkyl;

or two R on the same atom form an oxo.

In some embodiments of a compound of Formula (I), the compound is of Formula (Ia):

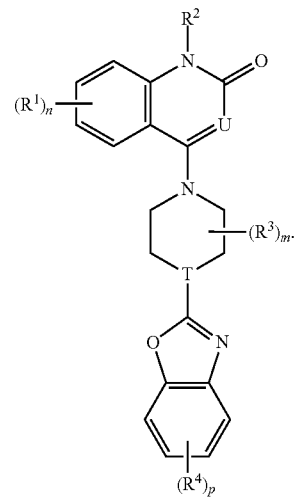

Formula (Ia)

In some embodiments of a compound of Formula (I), the compound is of Formula (Ib):

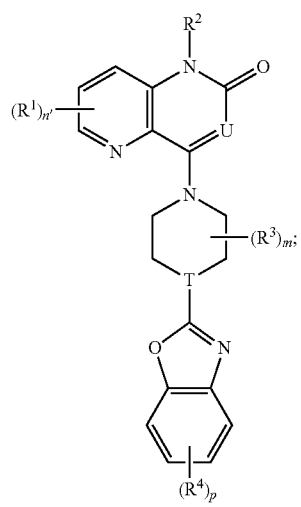

Formula (Ib)

wherein n' is 0-3

In some embodiments of a compound of Formula (I), the compound is of Formula (Ic):

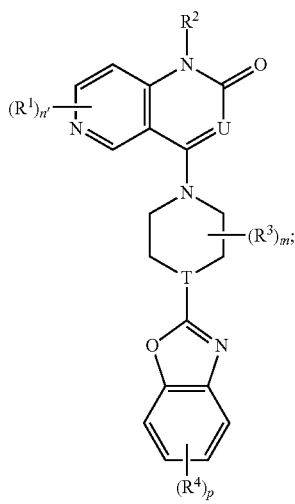

Formula (Ic)

wherein n' is 0-3

In some embodiments of a compound of Formula (I), the compound is of Formula (Id):

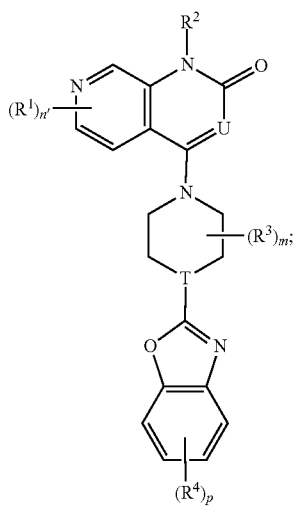

Formula (Id)

wherein n' is 0-3

In some embodiments of a compound of Formula (I), the compound is of Formula (Ie):

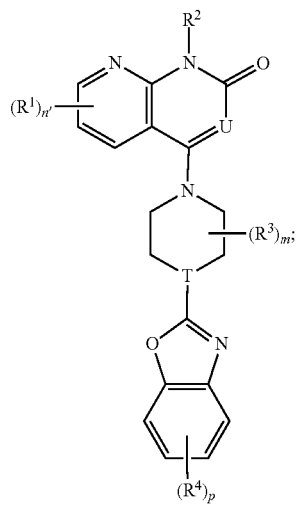

Formula (Ie)

wherein n' is 0-3

In some embodiments of a compound of Formula (I), the compound is of Formula (If):

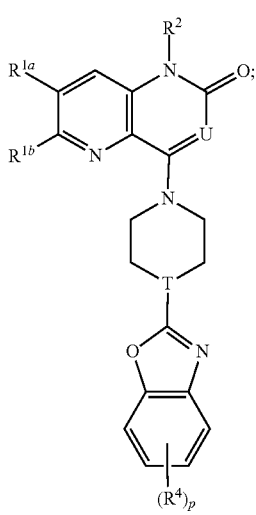

Formula (If)

wherein each $R^{1a}$ and $R^{1b}$ are independently selected from $R^1$.

In some embodiments of a compound of Formula (I), the compound is of Formula (Ig):

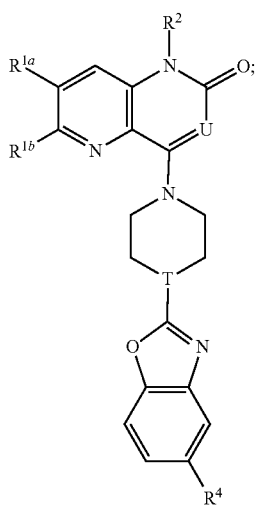

Formula (Ig)

wherein each $R^{1a}$ and $R^{1b}$ are independently selected from $R^1$.

Disclosed herein is a compound of Formula (II), or a pharmaceutically acceptable salt thereof:

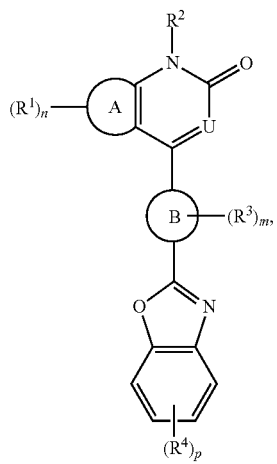

Formula (II)

wherein:

Ring A is phenyl or 6-membered heteroaryl;

each $R^1$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

n is 0-4;

$R^2$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl;

U is N or CR$^U$;

$R^U$ is hydrogen, halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

Ring B is a bicyclic ring;

each $R^3$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

or two $R^3$ on the same atom are taken together to form an oxo;

m is 0-8;

each $R^4$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

p is 0-4;

each $R^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or two $R^a$ are taken together with the atom to which they are attached to form a heterocycloalkyl optionally substituted with one or more R;

each $R^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or two $R^b$ are taken together with the atom to which they are attached to form a heterocycloalkyl optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl), wherein each alkyl, alkylene, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$alkoxy, $C_1$-$C_6$haloalkyl, $C_1$-$C_6$hydroxyalkyl, $C_1$-$C_6$aminoalkyl, $C_1$-$C_6$heteroalkyl, or $C_3$-$C_6$cycloalkyl;

or two R on the same atom form an oxo.

In some embodiments of a compound of Formula (II), the compound is of Formula (IIa):

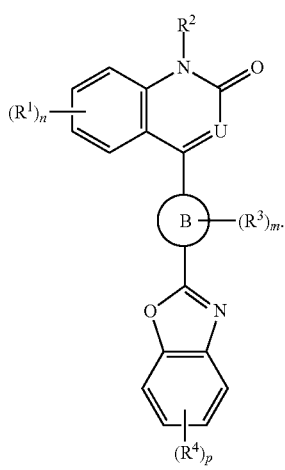

Formula (IIa)

In some embodiments of a compound of Formula (II), the compound is of Formula (IIb):

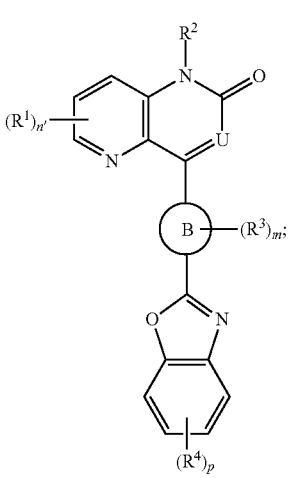

Formula (IIb)

wherein n' is 0-3

In some embodiments of a compound of Formula (II), the compound is of Formula (IIc):

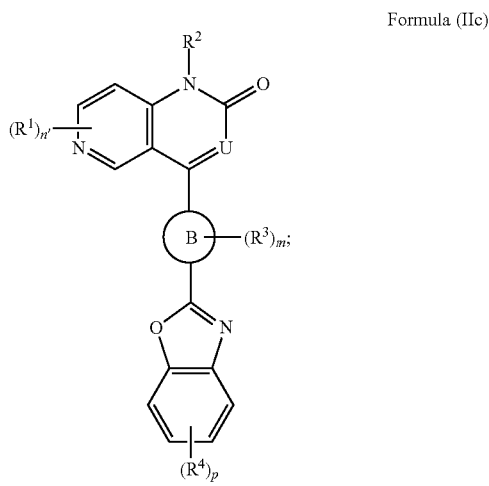

Formula (IIc)

wherein n' is 0-3

In some embodiments of a compound of Formula (II), the compound is of Formula (IId):

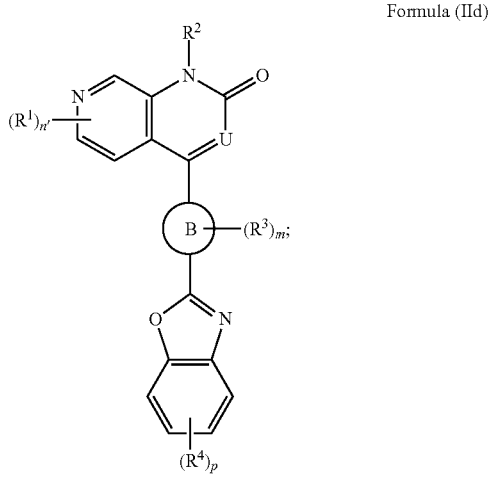

Formula (IId)

wherein n' is 0-3

In some embodiments of a compound of Formula (II), the compound is of Formula (IIe):

Formula (IIe)

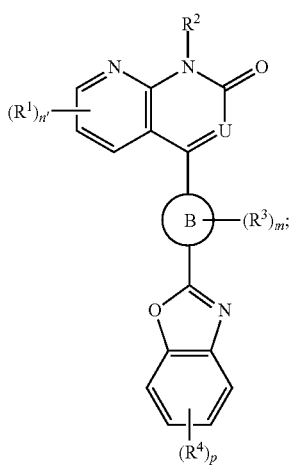

wherein n' is 0-3

Also disclosed herein is a pharmaceutical composition comprising a compound disclosed herein, or a pharmaceutically acceptable salt thereof, and a pharmaceutically acceptable excipient.

Also disclosed herein is a method of inhibiting the activity of at least one of diacylglycerol kinase selected from diacylglycerol kinase alpha (DGKalpha) and diacylglycerol kinase zeta (DGKzeta), in a subject in need thereof, the method comprising administering to the subject a compound disclosed herein, or a pharmaceutically acceptable salt thereof.

Also disclosed herein is a method of inhibiting the activity of diacylglycerol kinase alpha (DGKalpha), in a subject in need thereof, the method comprising administering to the subject a compound disclosed herein, or a pharmaceutically acceptable salt thereof.

Also disclosed herein is a method of a disease associated with aberrant diacylglycerol kinase signaling, in a subject in need thereof, the method comprising administering to the subject a compound disclosed herein, or a pharmaceutically acceptable salt thereof.

In some embodiments, the diacylglycerol kinase is diacylglycerol kinase alpha. In some embodiments, the disease is cancer or a viral infection. In some embodiments, the method further comprises administering an additional therapeutic agent. In some embodiments, the additional therapeutic agent is an anti-cancer agent or an anti-viral agent.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Carboxyl" refers to —COOH.

"Cyano" refers to —CN.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "C$_2$-C$_6$ alkenyl" or "C$_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "C$_2$-C$_6$ alkynyl" or "C$_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom), spiro, or bridged ring systems. In some embodiments, the cycloalkyl is fully saturated. Representative cycloalkyls include, but are not limited to, cycloalkyls having from three to fifteen carbon atoms (C$_3$-C$_{15}$ fully saturated cycloalkyl or C$_3$-C$_{15}$ cycloalkenyl), from three to ten carbon atoms (C$_3$-C$_{10}$ fully saturated cycloalkyl or C$_3$-C$_{10}$ cycloalkenyl), from three to eight carbon atoms (C$_3$-C$_5$ fully saturated cycloalkyl or C$_3$-C$_5$ cycloalkenyl), from three to six carbon atoms (C$_3$-C$_6$ fully saturated cycloalkyl or C$_3$-C$_6$ cycloalkenyl), from three to five carbon atoms (C$_3$-C$_5$ fully saturated cycloalkyl or C$_3$-C$_5$ cycloalkenyl), or three to four carbon atoms (C$_3$-C$_4$ fully saturated cycloalkyl or C$_3$-C$_4$ cycloalkenyl). In some embodiments, the cycloalkyl is a 3- to 10-membered fully saturated cycloalkyl or a 3- to 10-membered cycloalkenyl. In some embodiments, the cycloalkyl is a 3- to 6-membered fully saturated cycloalkyl or a 3- to 6-membered cycloalkenyl. In some embodiments, the cycloalkyl is a 5- to 6-membered fully saturated cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ fully saturated heterocycloalkyl or $C_2$-$C_{15}$ heterocycloalkenyl), from two to ten carbon atoms ($C_2$-$C_{10}$ fully saturated heterocycloalkyl or $C_2$-$C_{10}$ heterocycloalkenyl), from two to eight carbon atoms ($C_2$-$C_8$ fully saturated heterocycloalkyl or $C_2$-$C_8$ heterocycloalkenyl), from two to seven carbon atoms ($C_2$-$C_7$ fully saturated heterocycloalkyl or $C_2$-$C_7$ heterocycloalkenyl), from two to six carbon atoms ($C_2$-$C_6$ fully saturated heterocycloalkyl or $C_2$-$C_6$ heterocycloalkenyl), from two to five carbon atoms ($C_2$-$C_5$ fully saturated heterocycloalkyl or $C_2$-$C_5$ heterocycloalkenyl), or two to four carbon atoms ($C_2$-$C_4$ fully saturated heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns that are sterically impractical and/or synthetically non-feasible. Thus, any substituents described should generally be understood as having a maximum molecular weight of about 1,000 daltons, and more typically, up to about 500 daltons.

The term "one or more" when referring to an optional substituent means that the subject group is optionally substituted with one, two, three, or four substituents. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents.

An "effective amount" or "therapeutically effective amount" refers to an amount of a compound administered to a mammalian subject, either as a single dose or as part of a series of doses, which is effective to produce a desired therapeutic effect.

The terms "treat," "treating" or "treatment," as used herein, include alleviating, abating, or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition.

As used herein, a "disease or disorder associated with DGK" or, alternatively, "a DGK-mediated disease or disorder" means any disease or other deleterious condition in which DGK, or a mutant thereof, is known or suspected to play a role.

As used herein, a "disease or disorder associated with DGKalpha" or, alternatively, "a DGKalpha-mediated disease or disorder" means any disease or other deleterious condition in which DGKalpha, or a mutant thereof, is known or suspected to play a role.

As used herein, a "disease or disorder associated with DGKzeta" or, alternatively, "a DGKzeta-mediated disease or disorder" means any disease or other deleterious condition in which DGKzeta, or a mutant thereof, is known or suspected to play a role.

Compounds

Described herein are compounds, or a pharmaceutically acceptable salt thereof useful in the treatment of a disease or disorder associated with DGK, especially DGKalpha.

Disclosed herein is a compound of Formula (I), or a pharmaceutically acceptable salt thereof:

Formula (I)

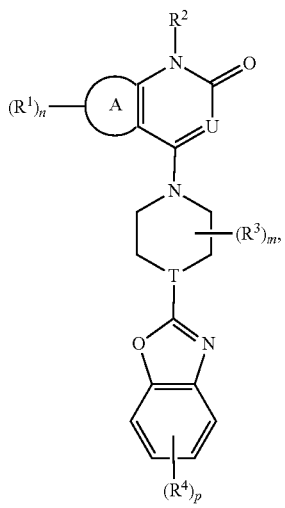

wherein:

Ring A is phenyl or 6-membered heteroaryl;

each $R^1$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

n is 0-4;

$R^2$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl;

U is N or CR$^U$;

$R^U$ is hydrogen, halogen, —OH, —OR$^a$, —NR$^c$R$^d$, —C(=O)R$^a$, —C(=O)OR$^b$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

each $R^3$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

or two $R^3$ on the same atom are taken together to form an oxo;

or two $R^3$ on adjacent carbons are taken together to form an alkenylene;

or two $R^3$ on the same or different carbons are taken together to form a cycloalkyl or heterocycloalkyl, each optionally substituted with one or more R;

m is 0-8;

T is N or CR$^T$;

$R^T$ is hydrogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

each $R^4$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

p is 0-4;

each $R^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or two $R^a$ are taken together with the atom to which they are attached to form a heterocycloalkyl optionally substituted with one or more R;

each $R^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or two $R^b$ are taken together with the atom to which they are attached to form a heterocycloalkyl optionally substituted with one or more R;

$R^c$ and $R^d$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)

OCH$_3$, C$_1$-C$_6$alkyl, C$_1$-C$_6$alkoxy, C$_1$-C$_6$haloalkyl, C$_1$-C$_6$hydroxyalkyl, C$_1$-C$_6$aminoalkyl, C$_1$-C$_6$heteroalkyl, or C$_3$-C$_6$cycloalkyl;

or two R on the same atom form an oxo.

Disclosed herein is a compound of Formula (I), or a pharmaceutically acceptable salt thereof:

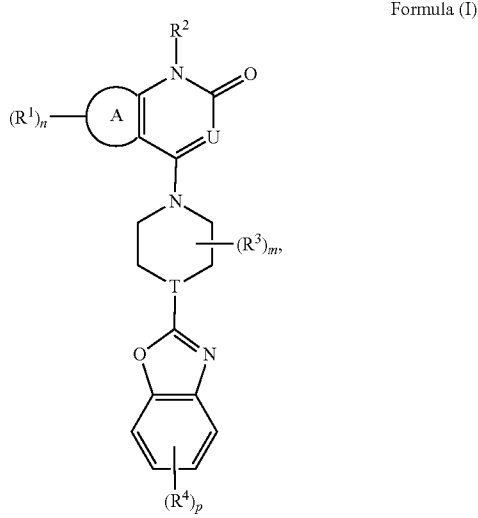

Formula (I)

wherein:

Ring A is phenyl or 6-membered heteroaryl;

each R$^1$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

n is 0-4;

R$^2$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl;

U is N or CR$^U$;

R$^U$ is hydrogen, halogen, —OH, —OR$^a$, —NR$^c$R$^d$, —C(=O)R$^a$, —C(=O)OR$^b$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

each R$^3$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

or two R$^3$ on the same atom are taken together to form an oxo;

or two R$^3$ on the same or different carbons are taken together to form a cycloalkyl or heterocycloalkyl, each optionally substituted with one or more R;

m is 0-8;

T is N or CR$^T$;

R$^T$ is hydrogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

each R$^4$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

p is 0-4;

each R$^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or two R$^a$ are taken together with the atom to which they are attached to form a heterocycloalkyl optionally substituted with one or more R;

each R$^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or two R$^b$ are taken together with the atom to which they are attached to form a heterocycloalkyl optionally substituted with one or more R;

R$^c$ and R$^d$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or R$^c$ and R$^d$ are taken together with the atom to which they are attached to form a heterocycloalkyl optionally substituted with one or more R; and each R is independently halogen, —CN, —OH, —S(=O)CH₃, —S(=O)₂CH₃, —S(=O)₂NH₂, —S(=O)₂NHCH₃, —S(=O)₂N(CH₃)₂, —NH₂, —NHCH₃, —N(CH₃)₂, —C(=O)CH₃, —C(=O)OH, —C(=O)OCH₃, $C_1$-$C_6$alkyl, $C_1$-$C_6$alkoxy, $C_1$-$C_6$haloalkyl, $C_1$-$C_6$hydroxyalkyl, $C_1$-$C_6$aminoalkyl, $C_1$-$C_6$heteroalkyl, or $C_3$-$C_6$cycloalkyl;

or two R on the same atom form an oxo.

In some embodiments of a compound of Formula (I), Ring A is phenyl. In some embodiments of a compound of Formula (I), Ring A is 6-membered heteroaryl. In some embodiments of a compound of Formula (I), Ring A is pyridinyl.

In some embodiments of a compound of Formula (I), the compound is of Formula (Ia):

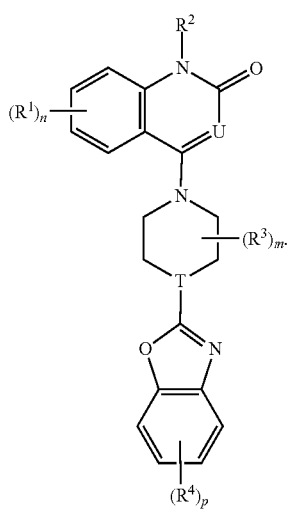

Formula (Ia)

In some embodiments of a compound of Formula (I), the compound is of Formula (Ib):

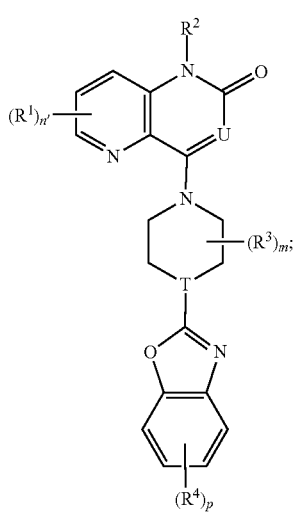

Formula (Ib)

wherein n' is 0-3

In some embodiments of a compound of Formula (I), the compound is of Formula (Ic):

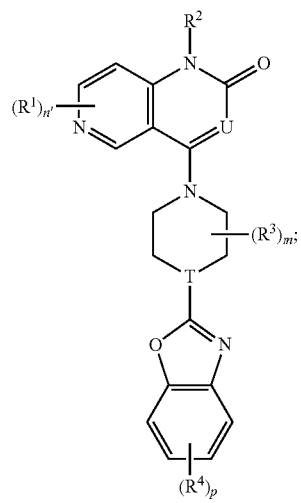

Formula (Ic)

wherein n' is 0-3

In some embodiments of a compound of Formula (I), the compound is of Formula (Id):

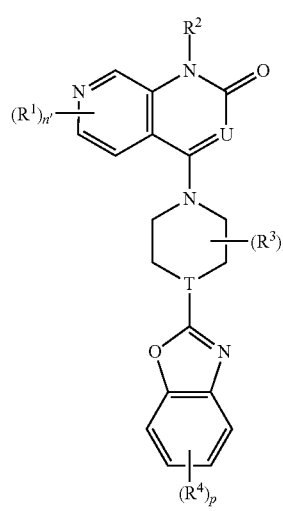

Formula (Id)

wherein n' is 0-3

In some embodiments of a compound of Formula (I), the compound is of Formula (Ie):

Formula (Ie)

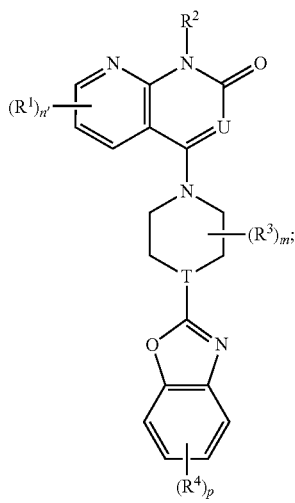

wherein n' is 0-3

In some embodiments of a compound of Formula (I), the compound is of Formula (If):

Formula (If)

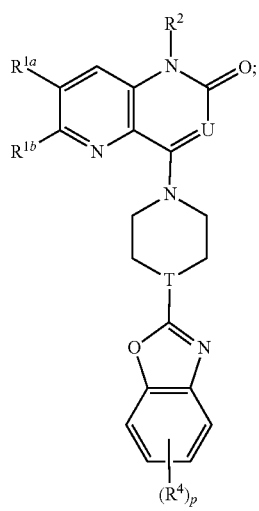

wherein each $R^{1a}$ and $R^{1b}$ are independently selected from $R^1$.

In some embodiments of a compound of Formula (I), the compound is of Formula (Ig):

Formula (Ig)

wherein each $R^{1a}$ and $R^{1b}$ are independently selected from $R^1$.

In some embodiments of a compound of Formula (Ib), n' is 1 or 2; each $R^1$ is independently —CN, —O-heterocycloalkyl, —O—$C_1$-$C_6$alkyl, —O—$C_1$-$C_6$haloalkyl, —O—$C_1$-$C_6$hydroxylalkyl, or —O—$C_1$-$C_6$aminoalkyl; $R^2$ is $C_1$-$C_6$alkyl; T is CH; U is N or CH; p is 1 or 2; and each $R^4$ is independently halogen or $C_1$-$C_6$alkyl. In some embodiments of a compound of Formula (Ib), p is 1. In some embodiments of a compound of Formula (Ib), p is 2. In some embodiments, $R^4$ is halogen such as F. In some embodiments, $R^4$ is $C_1$-$C_6$alkyl. In some embodiments of a compound of Formula (Ib), $R^4$ is $C_1$-$C_3$alkyl. In some embodiments of a compound of Formula (Ib), $R^4$ is methyl. In some embodiments, $R^2$ is $C_1$-$C_3$alkyl. In some embodiments of a compound of Formula (Ib), $R^2$ is methyl. In some embodiments of a compound of Formula (Ib), U is N. In some embodiments, U is CH. In some embodiments of a compound of Formula (Ib), each $R^1$ is independently —CN, —O-heterocycloalkyl, —O—$C_1$-$C_6$haloalkyl, —O—$C_1$-$C_6$hydroxylalkyl, or —O—$C_1$-$C_6$aminoalkyl. In some embodiments of a compound of Formula (Ib), each $R^1$ is independently —CN or —O-heterocycloalkyl. In some embodiments of a compound of Formula (Ib), each $R^1$ is independently —CN or —O—$C_1$-$C_6$haloalkyl. In some embodiments of a compound of Formula (Ib), each $R^1$ is independently —CN or —O—$C_1$-$C_6$hydroxylalkyl. In some embodiments of a compound of Formula (Ib), each $R^1$ is independently —CN or —O—$C_1$-$C_3$hydroxylalkyl. In some embodiments of a compound of Formula (Ib), each $R^1$ is independently —CN or —O—$C_1$-$C_6$aminoalkyl. In some embodiments of a compound of Formula (Ib), each $R^1$ is independently —CN or —O—$CH_2CH_2OH$. In some embodiments of a compound of Formula (Ib), at least one $R^1$ is CN. In some embodiments of a compound of Formula (Ib), n' is 1. In some embodiments of a compound of Formula (Ib), n' is 2.

In some embodiments of a compound of Formula (If), each $R^{1a}$ and $R^{1b}$ are independently —CN, —O-heterocycloalkyl, —O—$C_1$-$C_6$alkyl, —O—$C_1$-$C_6$haloalkyl, —O—$C_1$-$C_6$hydroxylalkyl, or —O—$C_1$-$C_6$aminoalkyl; $R^2$ is $C_1$-$C_6$alkyl; T is CH; U is N or CH; p is 1 or 2; and each $R^4$ is independently halogen or $C_1$-$C_6$alkyl. In some embodiments of a compound of Formula (If), p is 1. In some embodiments of a compound of Formula (If), p is 2. In some embodiments of a compound of Formula (If), $R^4$ is halogen such as F. In some embodiments of a compound of Formula (If), $R^4$ is $C_1$-$C_6$alkyl. In some embodiments of a compound of Formula (If), $R^4$ is $C_1$-$C_3$alkyl. In some embodiments of a compound of Formula (If), $R^4$ is methyl. In some embodiments of a compound of Formula (If), $R^2$ is $C_1$-$C_3$alkyl. In some embodiments of a compound of Formula (If), $R^2$ is methyl. In some embodiments of a compound of Formula (If), U is N. In some embodiments of a compound of Formula (If), U is CH. In some embodiments of a compound of Formula (If), each $R^{1a}$ and $R^{1b}$ are independently —CN, —O-heterocycloalkyl, —O—$C_1$-$C_6$haloalkyl, —O—$C_1$-$C_6$hydroxylalkyl, or —O—$C_1$-$C_6$aminoalkyl. In some embodiments of a compound of Formula (If), each $R^{1a}$ and $R^{1b}$ are independently —CN or —O-heterocycloalkyl. In some embodiments of a compound of Formula (If), each $R^{1a}$ and $R^{1b}$ are independently —CN or —O—$C_1$-$C_6$haloalkyl. In some embodiments of a compound of Formula (If), each $R^{1a}$ and $R^{1b}$ are independently —CN or —O—$C_1$-$C_6$hydroxylalkyl. In some embodiments of a compound of Formula (If), each $R^{1a}$ and $R^{1b}$ are independently —CN or —O—$C_1$-$C_6$aminoalkyl. In some embodiments of a compound of Formula (If), $R^{1a}$ is —O—$C_1$-$C_6$hydroxylalkyl, $R^{1b}$ is CN. In some embodiments of a compound of Formula (If), $R^{1a}$ is —O—$C_1$-$C_3$hydroxylalkyl, $R^{1b}$ is CN. In some embodiments of a compound of Formula (If), $R^{1a}$ is —O—$CH_2CH_2OH$, $R^{1b}$ is CN.

In some embodiments of a compound of Formula (Ig), each $R^{1a}$ and $R^{1b}$ are independently —CN, —O-heterocycloalkyl, —O—$C_1$-$C_6$alkyl, —O—$C_1$-$C_6$haloalkyl, —O—$C_1$-$C_6$hydroxylalkyl, or —O—$C_1$-$C_6$aminoalkyl; $R^2$ is $C_1$-$C_6$alkyl; T is CH; U is N or CH; and $R^4$ is halogen or $C_1$-$C_6$alkyl. In some embodiments of a compound of Formula (Ig), $R^4$ is halogen such as F. In some embodiments of a compound of Formula (Ig), $R^4$ is $C_1$-$C_6$alkyl. In some embodiments of a compound of Formula (Ig), $R^4$ is $C_1$-$C_3$alkyl. In some embodiments of a compound of Formula (Ig), $R^4$ is methyl. In some embodiments of a compound of Formula (Ig), $R^2$ is $C_1$-$C_3$alkyl. In some embodiments of a compound of Formula (Ig), $R^2$ is methyl. In some embodiments of a compound of Formula (Ig), U is N. In some embodiments of a compound of Formula (Ig), U is CH. In some embodiments of a compound of Formula (Ig), each $R^{1a}$ and $R^{1b}$ are independently —CN, —O-heterocycloalkyl, —O—$C_1$-$C_6$haloalkyl, —O—$C_1$-$C_6$hydroxylalkyl, or —O—$C_1$-$C_6$aminoalkyl. In some embodiments of a compound of Formula (Ig), each $R^{1a}$ and $R^{1b}$ are independently —CN or —O-heterocycloalkyl. In some embodiments of a compound of Formula (Ig), each $R^{1a}$ and $R^{1b}$ are independently —CN or —O—$C_1$-$C_6$haloalkyl. In some embodiments of a compound of Formula (Ig), each $R^{1a}$ and $R^{1b}$ are independently —CN or —O—$C_1$-$C_6$hydroxylalkyl. In some embodiments of a compound of Formula (Ig), each $R^{1a}$ and $R^{1b}$ are independently —CN or —O—$C_1$-$C_6$aminoalkyl. In some embodiments of a compound of Formula (Ig), $R^{1a}$ is —O—$C_1$-$C_6$hydroxylalkyl, and $R^{1b}$ is CN. In some embodiments of a compound of Formula (Ig), $R^h$ is —O—$C_1$-$C_3$hydroxylalkyl, and $R^{1b}$ is CN. In some embodiments of a compound of Formula (Ig), $R^{1a}$ is —O—$CH_2CH_2OH$, and $R^{1b}$ is CN.

In some embodiments of a compound of Formula (If) or (Ig), $R^{1a}$ is halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (If) or (Ig), $R^{1a}$ is halogen, —CN, —OH, —$OR^a$, —$NR^cR^d$, $C_1$-$C_6$alkyl, or $C_1$-$C_6$haloalkyl. In some embodiments of a compound of Formula (If) or (Ig), $R^{1a}$ is halogen, —CN, $C_1$-$C_6$alkyl, or $C_1$-$C_6$haloalkyl. In some embodiments of a compound of Formula (If) or (Ig), $R^{1a}$ is halogen or —CN. In some embodiments of a compound of Formula (If) or (Ig), $R^{1a}$ is halogen. In some embodiments of a compound of Formula (If) or (Ig), $R^{1a}$ is fluoro or chloro. In some embodiments of a compound of Formula (If) or (Ig), $R^{1a}$ is —CN. In some embodiments of a compound of Formula (If) or (Ig), $R^{1a}$ is independently halogen, —CN, —$OR^a$, or —$NR^cR^d$. In some embodiments of a compound of Formula (If) or (Ig), $R^{1a}$ is —CN or —$OR^a$. In some embodiments of a compound of Formula (If) or (Ig), Ria is —CN, —O-heterocycloalkyl, —O—$C_1$-$C_6$alkyl, —O—$C_1$-$C_6$haloalkyl, —O—$C_1$-$C_6$hydroxylalkyl, or —O—$C_1$-$C_6$aminoalkyl. In some embodiments of a compound of Formula (If) or (Ig), $R^{1a}$ is —CN, —O— heterocycloalkyl, —O—$C_1$-$C_3$alkyl, —O—$C_1$-$C_3$haloalkyl, —O—$C_1$-$C_3$hydroxylalkyl, or —O—$C_1$-$C_3$aminoalkyl. In some embodiments of a compound of Formula (If) or (Ig), $R^{1a}$ is independently —CN or —$NR^cR^d$. In some embodiments of a compound of Formula (If) or (Ig), —$OR^a$ is —O-heterocycloalkyl, —O—$C_1$-$C_6$alkyl, —O—$C_1$-$C_6$haloalkyl, —O—$C_1$-$C_6$hydroxylalkyl, or —O—$C_1$-$C_6$aminoalkyl. In some embodiments of a compound of Formula (If) or (Ig), —$OR^a$ is —O-heterocycloalkyl, wherein the heterocycloalkyl is a 5 or 6 membered ring. In some embodiments of a compound of Formula (If) or (Ig), —$OR^a$ is

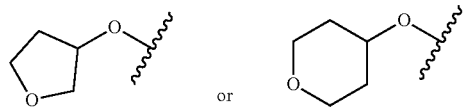

In some embodiments of a compound of Formula (If) or (Ig), —$OR^a$ is —O—$C_1$-$C_6$alkyl. In some embodiments of a compound of Formula (If) or (Ig), —$OR^a$ is —O—$C_1$-$C_6$haloalkyl. In some embodiments of a compound of Formula (If) or (Ig), —$OR^a$ is —O—$C_1$-$C_6$hydroxylalkyl. In some embodiments of a compound of Formula (If) or (Ig), —$OR^a$ is —O—$C_1$-$C_6$aminoalkyl.

In some embodiments of a compound of Formula (If) or (Ig), $R^{1b}$ is halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (If) or (Ig), $R^{1b}$ is halogen, —CN, —OH, —$OR^a$, —$NR^cR^d$, $C_1$-$C_6$alkyl, or $C_1$-$C_6$haloalkyl. In some embodiments of a compound of Formula (If) or (Ig), $R^{1b}$ is halogen, —CN, $C_1$-$C_6$alkyl, or $C_1$-$C_6$haloalkyl. In some embodiments of a compound of Formula (If) or (Ig), $R^{1b}$ is halogen or —CN. In some embodiments of a compound of Formula (If) or (Ig), $R^{1b}$ is halogen. In some embodiments of a compound of Formula (If) or (Ig), $R^{1b}$ is fluoro or chloro. In some embodiments of a compound of Formula (If) or (Ig), $R^{1b}$ is —CN. In some embodiments of a compound of Formula (If) or (Ig), $R^{1b}$ is independently halogen, —CN, —$OR^a$, or —$NR^cR^d$. In some embodiments of a compound of Formula (If) or (Ig), $R^{1b}$ is —CN or —$OR^a$. In some embodiments of a compound of Formula (If) or (Ig), $R^{1b}$ is —CN, —O-heterocycloalkyl, —O—$C_1$-$C_6$alkyl, —O—$C_1$-$C_6$haloalkyl, —O—$C_1$-$C_6$hydroxylalkyl, or —O—$C_1$-$C_6$aminoalkyl. In some embodiments of a compound of Formula (If) or (Ig), $R^{1b}$ is —CN, —O— heterocycloalkyl, —O—C$_1$-C$_3$alkyl, —O—C$_1$-C$_3$haloalkyl, —O—C$_1$-C$_3$hydroxylalkyl, or —O—C$_1$-C$_3$aminoalkyl. In some embodiments of a compound of Formula (If) or (Ig), R$^{1b}$ is independently —CN or —NR$^c$R$^d$. In some embodiments of a compound of Formula (If) or (Ig), —OR$^a$ is —O-heterocycloalkyl, —O—C$_1$-C$_6$alkyl, —O—C$_1$-C$_6$haloalkyl, —O—C$_1$-C$_6$hydroxylalkyl, or —O—C$_1$-C$_6$aminoalkyl. In some embodiments of a compound of Formula (If) or (Ig), —OR$^a$ is —O-heterocycloalkyl, wherein the heterocycloalkyl is a 5 or 6 membered ring. In some embodiments of a compound of Formula (If) or (Ig), —OR$^a$ is

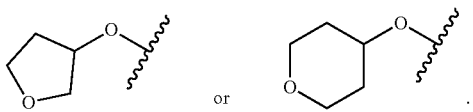 [SMILES: *OC1CCOC1 ; *OC1CCOCC1]

In some embodiments of a compound of Formula (If) or (Ig), —OR$^a$ is —O—C$_1$-C$_6$alkyl. In some embodiments of a compound of Formula (If) or (Ig), —OR$^a$ is —O—C$_1$-C$_6$haloalkyl. In some embodiments of a compound of Formula (If) or (Ig), —OR$^a$ is —O—C$_1$-C$_6$hydroxylalkyl. In some embodiments of a compound of Formula (If) or (Ig), —OR$^a$ is —O—C$_1$-C$_6$aminoalkyl.

In some embodiments of a compound of Formula (I) or (Ia), wherein n is 0, 1, 2, 3, or 4. In some embodiments of a compound of Formula (I) or (Ia), wherein n is 0-2. In some embodiments of a compound of Formula (I) or (Ia), n is 0 or 1. In some embodiments of a compound of Formula (I) or (Ia), n is 2. In some embodiments of a compound of Formula (I) or (Ia), n is 1. In some embodiments of a compound of Formula (I) or (Ia), n is 0.

In some embodiments of a compound of Formula (Ib)-(Ie), n' is 0, 1, 2, or 3. In some embodiments of a compound of Formula (Ib)-(Ie), n' is 0-2. In some embodiments of a compound of Formula (Ib)-(Ie), n' is 0 or 1. In some embodiments of a compound of Formula (Ib)-(Ie), n' is 2. In some embodiments of a compound of Formula (Ib)-(Ie), n' is 1. In some embodiments of a compound of Formula (Ib)-(Ie), n' is 0.

In some embodiments of a compound of Formula (I) or (Ia)-(Ig), each R$^1$ is independently halogen, —CN, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl. In some embodiments of a compound of Formula (I) or (Ia)-(Ig), each R$^1$ is independently halogen, —CN, —OH, —OR$^a$, —NR$^c$R$^d$, C$_1$-C$_6$alkyl, or C$_1$-C$_6$haloalkyl. In some embodiments of a compound of Formula (I) or (Ia)-(Ig), each R$^1$ is independently halogen, —CN, C$_1$-C$_6$alkyl, or C$_1$-C$_6$haloalkyl. In some embodiments of a compound of Formula (I) or (Ia)-(Ig), each R$^1$ is independently halogen or —CN. In some embodiments of a compound of Formula (I) or (Ia)-(Ig), each R$^1$ is independently halogen. In some embodiments of a compound of Formula (I) or (Ia)-(Ig), each R$^1$ is fluoro or chloro. In some embodiments of a compound of Formula (I) or (Ia)-(Ig), each R$^1$ is —CN. In some embodiments of a compound of Formula (I) or (Ia)-(Ig), each R$^1$ is independently halogen, —CN, —OR$^a$, or —NR$^c$R$^d$. In some embodiments of a compound of Formula (I) or (Ia)-(Ig), each R$^1$ is independently —CN or —OR$^a$. In some embodiments of a compound of Formula (I) or (Ia)-(Ig), each R$^1$ is independently —CN, —O-heterocycloalkyl, —O—C$_1$-C$_6$alkyl, —O—C$_1$-C$_6$haloalkyl, —O—C$_1$-C$_6$hydroxylalkyl, or —O—C$_1$-C$_6$aminoalkyl. In some embodiments of a compound of Formula (I) or (Ia)-(Ig), each R$^1$ is independently —CN, —O-heterocycloalkyl, —O—C$_1$-C$_3$alkyl, —O—C$_1$-C$_3$haloalkyl, —O—C$_1$-C$_3$hydroxylalkyl, or —O—C$_1$-C$_3$aminoalkyl. In some embodiments of a compound of Formula (I) or (Ia)-(Ig), each R$^1$ is independently —CN or —NR$^c$R$^d$. In some embodiments of a compound of Formula (I) or (Ia)-(Ig), —OR$^a$ is —O-heterocycloalkyl, —O—C$_1$-C$_6$alkyl, —O—C$_1$-C$_6$haloalkyl, —O—C$_1$-C$_6$hydroxylalkyl, or —O—C$_1$-C$_6$aminoalkyl. In some embodiments of a compound of Formula (I) or (Ia)-(Ig), —OR$^a$ is —O-heterocycloalkyl, wherein the heterocycloalkyl is a 5 or 6 membered ring. In some embodiments of a compound of Formula (I) or (Ia)-(Ig), —OR$^a$ is

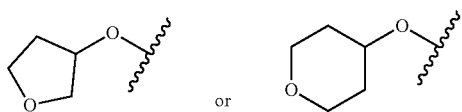

In some embodiments of a compound of Formula (I) or (Ia)-(Ig), —OR$^a$ is —O—C$_1$-C$_6$alkyl. In some embodiments of a compound of Formula (I) or (Ia)-(Ig), —OR$^a$ is —O—C$_1$-C$_6$haloalkyl. In some embodiments of a compound of Formula (I) or (Ia)-(Ig), —OR$^a$ is —O—C$_1$-C$_6$hydroxylalkyl. In some embodiments of a compound of Formula (I) or (Ia)-(Ig), —OR$^a$ is —O—C$_1$-C$_6$aminoalkyl. In some embodiments, each R$^1$ is independently —CN, —O-heterocycloalkyl, —O—C$_1$-C$_6$haloalkyl, —O—C$_1$-C$_6$hydroxylalkyl, or —O—C$_1$-C$_6$aminoalkyl. In some embodiments, each R$^1$ is independently —CN or —O-heterocycloalkyl. In some embodiments, each R$^1$ is independently —CN or —O—C$_1$-C$_6$haloalkyl. In some embodiments, each R$^1$ is independently —CN or —O—C$_1$-C$_6$hydroxylalkyl. In some embodiments, each R$^1$ is independently —CN or —O—C$_1$-C$_3$hydroxylalkyl. In some embodiments, each R$^1$ is independently —CN or —O—CH$_2$CH$_2$OH. In some embodiments, each R$^1$ is independently —CN or —O—C$_1$-C$_6$aminoalkyl. In some embodiments, at least one R$^1$ is —CN.

In some embodiments of a compound of Formula (I) or (Ia)-(Ig), R$^2$ is hydrogen or C$_1$-C$_6$alkyl. In some embodiments of a compound of Formula (I) or (Ia)-(Ig), R$^2$ is C$_1$-C$_6$alkyl. In some embodiments of a compound of Formula (I) or (Ia)-(Ig), R$^2$ is C$_1$-C$_3$alkyl. In some embodiments of a compound of Formula (I) or (Ia)-(Ig), R$^2$ is methyl.

In some embodiments of a compound of Formula (I) or (Ia)-(Ig), U is N. In some embodiments of a compound of Formula (I) or (Ia)-(Ig), U is CR$^U$.

In some embodiments of a compound of Formula (I) or (Ia)-(Ig), R$^U$ is hydrogen, halogen, —OH, —OR$^a$, —NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl. In some embodiments of a compound of Formula (I) or (Ia)-(Ig), R$^U$ is hydrogen, halogen, C$_1$-C$_6$alkyl, or C$_1$-C$_6$haloalkyl. In some embodiments of a compound of Formula (I) or (Ia)-(Ig), R$^U$ is hydrogen.

In some embodiments of a compound of Formula (I),
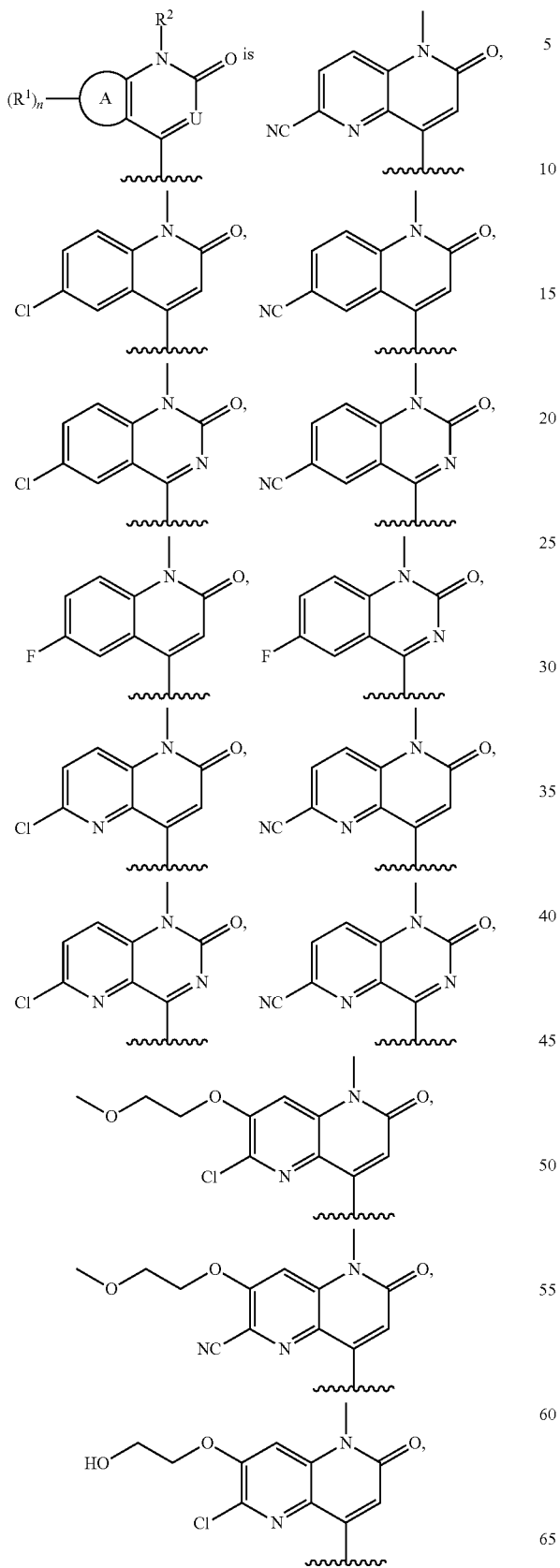
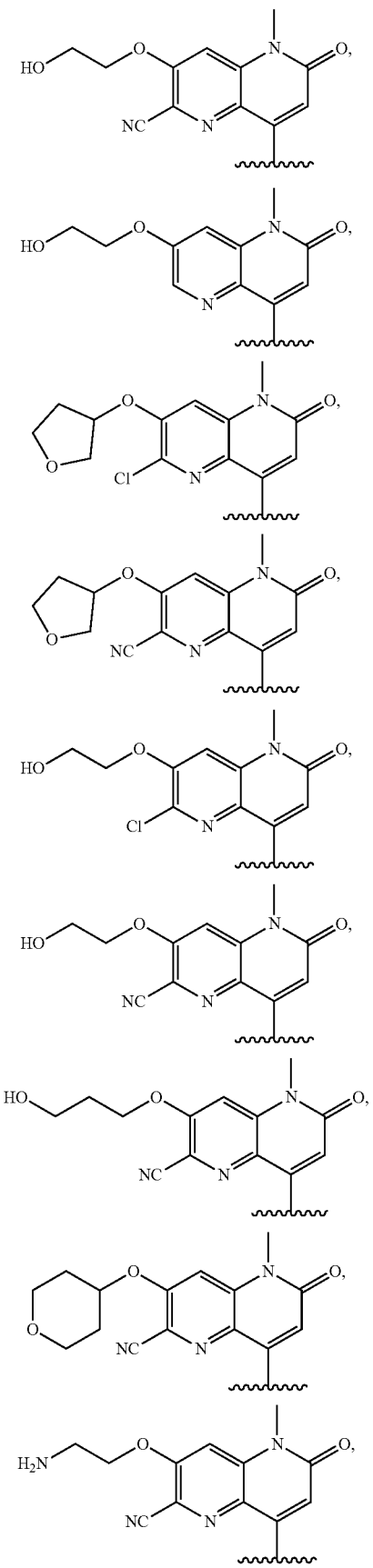

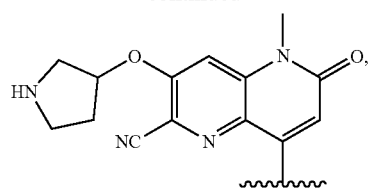
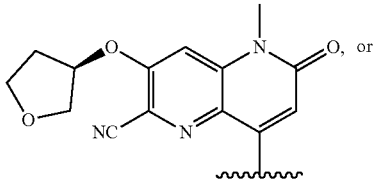, or
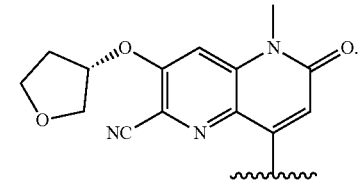
In some embodiments of a compound of Formula (I),
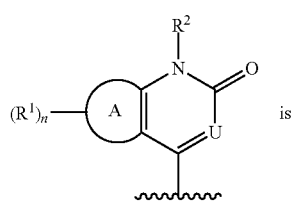 is
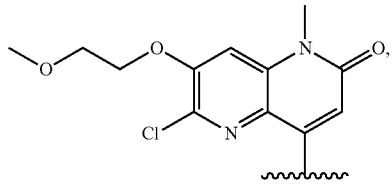
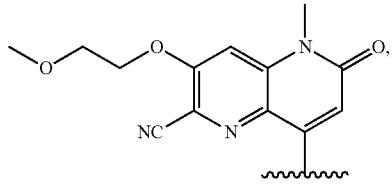
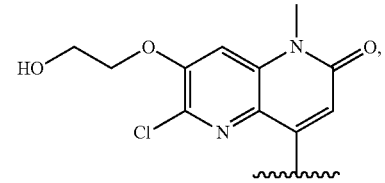
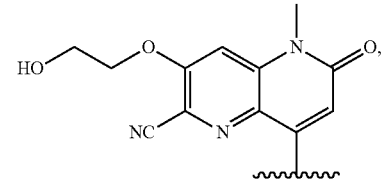
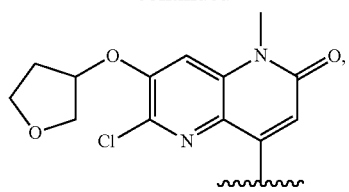
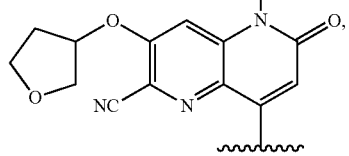
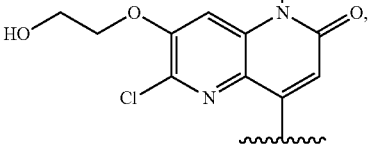
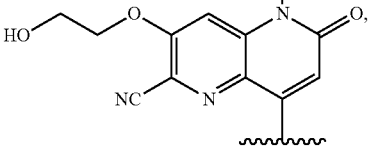
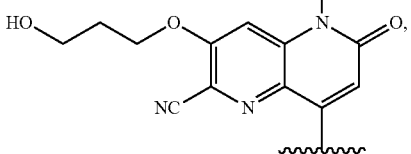
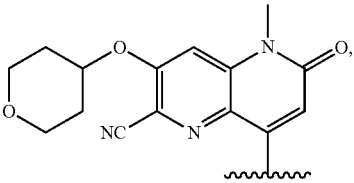
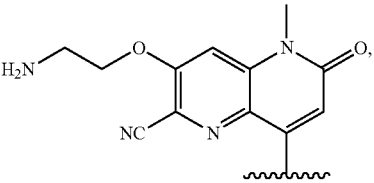
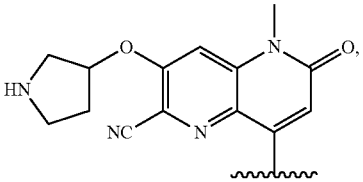
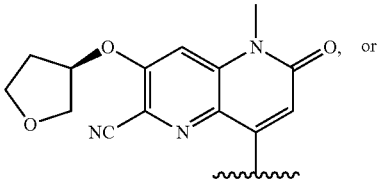, or In some embodiments of a compound of Formula (I), is

[chemical structures]

In some embodiments of a compound of Formula (I), is

[chemical structures]

In some embodiments of a compound of Formula (I), is

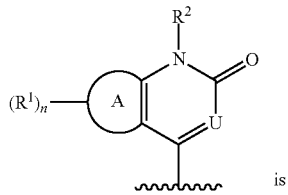

is

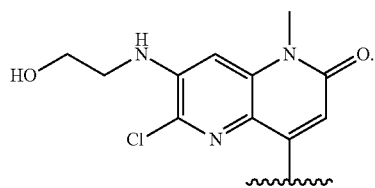

In some embodiments of a compound of Formula (I),

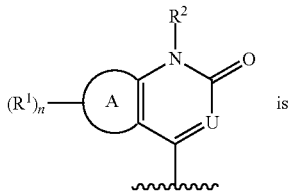

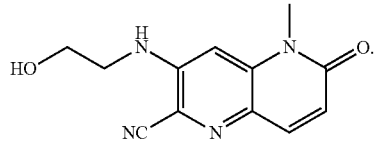

In some embodiments of a compound of Formula (I),

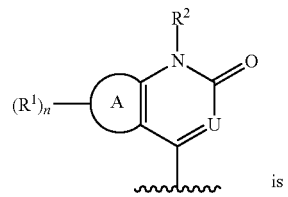

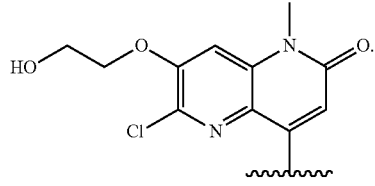

In some embodiments of a compound of Formula (I),

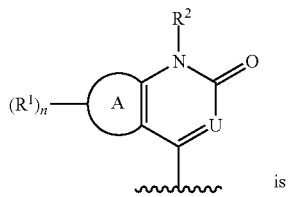

is

-continued

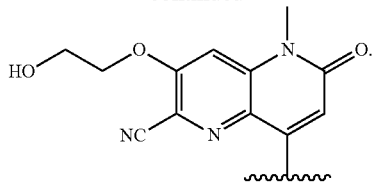

In some embodiments of a compound of Formula (I),

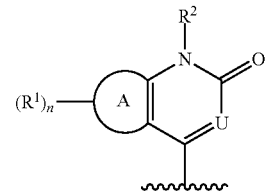

is

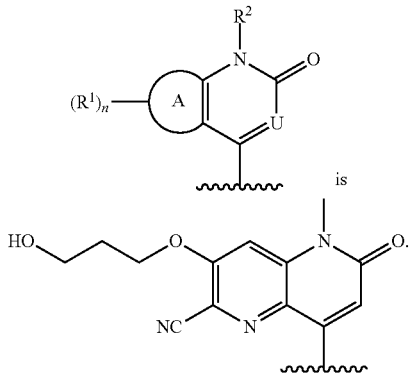

In some embodiments of a compound of Formula (I) or (Ia)-(Ie), each $R^3$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I) or (Ia)-(Ie), each $R^3$ is independently $C_1$-$C_6$alkyl or $C_1$-$C_6$haloalkyl. In some embodiments of a compound of Formula (I) or (Ia)-(Ie), each $R^3$ is independently $C_1$-$C_6$alkyl. In some embodiments of a compound of Formula (I) or (Ia)-(Ie), two $R^3$ on the same or different carbons are taken together to form a cycloalkyl or heterocycloalkyl, each optionally substituted with one or more R. In some embodiments of a compound of Formula (I) or (Ia)-(Ie), two $R^3$ on different carbons are taken together to form a cycloalkyl optionally substituted with one or more R.

In some embodiments of a compound of Formula (I) or (Ia)-(Ie), m is 0-4. In some embodiments of a compound of Formula (I) or (Ia)-(Ie), m is 0-3. In some embodiments of a compound of Formula (I) or (Ia)-(Ie), m is 0-2. In some embodiments of a compound of Formula (I) or (Ia)-(Ie), m is 0. In some embodiments of a compound of Formula (I) or (Ia)-(Ie), m is 1. In some embodiments of a compound of Formula (I) or (Ia)-(Ie), m is 2. In some embodiments of a compound of Formula (I) or (Ia)-(Ie), m is 3. In some embodiments of a compound of Formula (I) or (Ia)-(Ie), m is 4. In some embodiments of a compound of Formula (I) or (Ia)-(Ie), m is 3. In some embodiments of a compound of Formula (I) or (Ia)-(Ie), m is 5-8.

In some embodiments of a compound of Formula (I) or (Ia)-(Ig), T is N. In some embodiments of a compound of Formula (I) or (Ia)-(Ig), T is CR$^T$.

In some embodiments of a compound of Formula (I) or (Ia)-(Ig), R$^T$ is hydrogen or $C_1$-$C_6$alkyl. In some embodiments of a compound of Formula (I) or (Ia)-(Ig), R$^T$ is hydrogen.

In some embodiments of a compound of Formula (I) or (Ia)-(Ie),

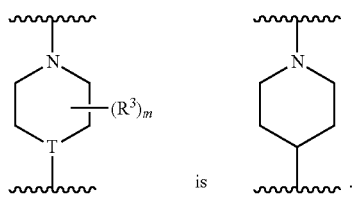

is

In some embodiments of a compound of Formula (I) or (Ia)-(Ig), each $R^4$ is independently halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I) or (Ia)-(Ig), each $R^4$ is independently halogen, —CN, —OH, —$OR^a$, —$NR^cR^d$, $C_1$-$C_6$alkyl, or $C_1$-$C_6$haloalkyl. In some embodiments of a compound of Formula (I) or (Ia)-(Ig), each $R^4$ is independently halogen, $C_1$-$C_6$alkyl, or $C_1$-$C_6$haloalkyl. In some embodiments of a compound of Formula (I) or (Ia)-(Ig), each $R^4$ is independently halogen or $C_1$-$C_6$alkyl. In some embodiments of a compound of Formula (I) or (Ia)-(Ig), each $R^4$ is independently $C_1$-$C_6$alkyl. In some embodiments of a compound of Formula (I) or (Ia)-(Ig), each $R^4$ is methyl. In some embodiments of a compound of Formula (I) or (Ia)-(Ig), $R^4$ is F.

In some embodiments of a compound of Formula (I) or (Ia)-(If), p is 0-2. In some embodiments of a compound of Formula (I) or (Ia)-(If), p is 1 or 2. In some embodiments of a compound of Formula (I) or (Ia)-(If), p is 0. In some embodiments of a compound of Formula (I) or (Ia)-(If), p is 1. In some embodiments of a compound of Formula (I) or (Ia)-(If), p is 2.

In some embodiments of a compound of Formula (I) or (Ia)-(If),

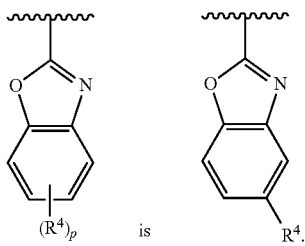

is

Disclosed herein is a compound of Formula (II), or a pharmaceutically acceptable salt thereof:

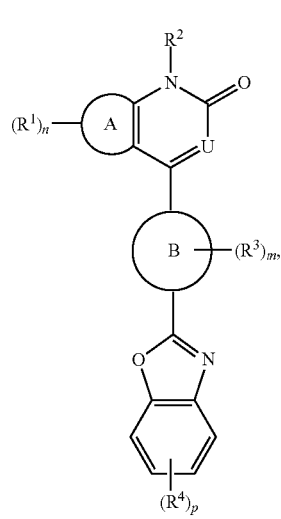

Formula (II)

wherein:
Ring A is phenyl or 6-membered heteroaryl;
each $R^1$ is independently halogen, —CN, —NO$_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;
n is 0-4;
$R^2$ is hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl;
U is N or $CR^U$;
$R^U$ is hydrogen, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;
Ring B is a bicyclic ring;
each $R^3$ is independently halogen, —CN, —NO$_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(=O)$_2NR^cR^d$, —$NR^cR^d$, —$NR^bC$(=O)$NR^cR^d$, —$NR^bC$(=O)$R^a$, —$NR^bC$(=O)$OR^b$, —$NR^bS$(=O)$_2R^a$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;
or two $R^3$ on the same atom are taken together to form an oxo;

m is 0-8;

each $R^4$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is optionally and independently substituted with one or more R;

p is 0-4;

each $R^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or two $R^a$ are taken together with the atom to which they are attached to form a heterocycloalkyl optionally substituted with one or more R;

each $R^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or two $R^b$ are taken together with the atom to which they are attached to form a heterocycloalkyl optionally substituted with one or more R;

$R^c$ and $R^d$ are each independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl), wherein each alkyl, alkylene, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl optionally substituted with one or more R; and each R is independently halogen, —CN, —OH, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$alkoxy, C$_1$-C$_6$haloalkyl, C$_1$-C$_6$hydroxyalkyl, C$_1$-C$_6$aminoalkyl, C$_1$-C$_6$heteroalkyl, or C$_3$-C$_6$cycloalkyl;

or two R on the same atom form an oxo.

In some embodiments of a compound of Formula (II), Ring A is phenyl. In some embodiments of a compound of Formula (II), Ring A is 6-membered heteroaryl. In some embodiments of a compound of Formula (II), Ring A is pyridinyl.

In some embodiments of a compound of Formula (II), the compound is of Formula (IIa):

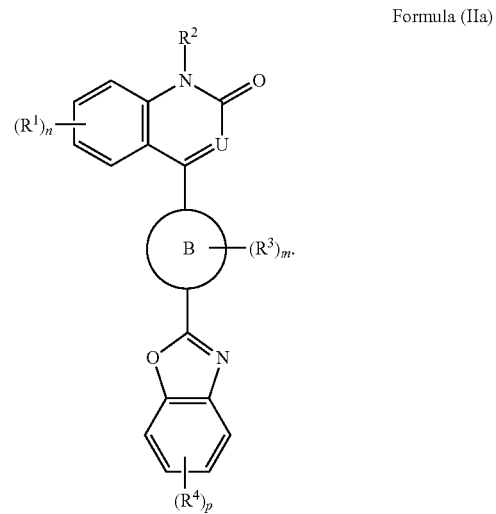

Formula (IIa)

In some embodiments of a compound of Formula (II), the compound is of Formula (IIb):

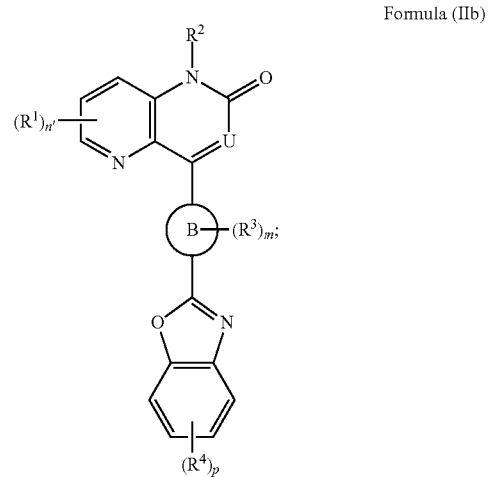

Formula (IIb)

wherein n' is 0-3

In some embodiments of a compound of Formula (II), the compound is of Formula (IIc):

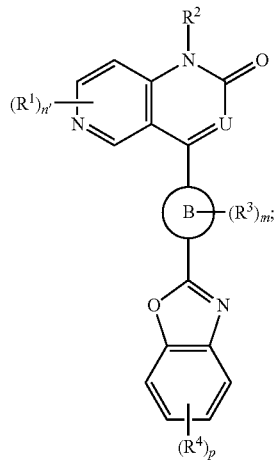

Formula (IIc)

wherein n' is 0-3

In some embodiments of a compound of Formula (II), the compound is of Formula (IId):

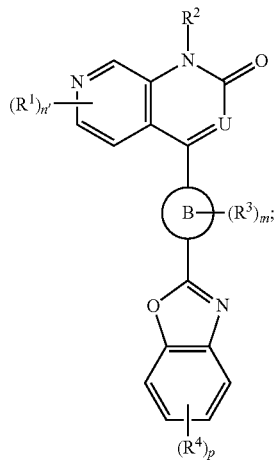

Formula (IId)

wherein n' is 0-3

In some embodiments of a compound of Formula (II), the compound is of Formula (IIe):

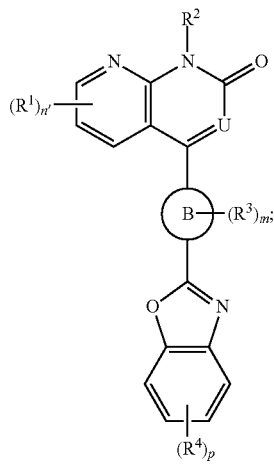

Formula (IIe)

wherein n' is 0-3

In some embodiments of a compound of Formula (II), the compound is of Formula (IIf):

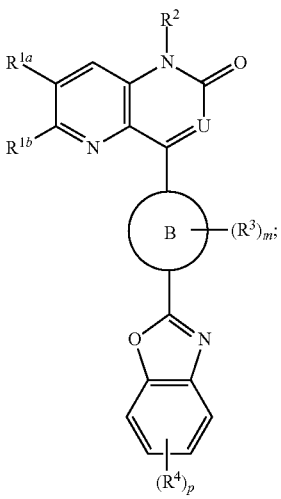

Formula (IIf)

wherein each $R^{1a}$ and $R^{1b}$ are independently selected from $R^1$.

In some embodiments of a compound of Formula (II) or (IIa), wherein n is 0, 1, 2, 3, or 4. In some embodiments of a compound of Formula (II) or (IIa), n is 0-2. In some embodiments of a compound of Formula (II) or (IIa), n is 0 or 1. In some embodiments of a compound of Formula (II) or (IIa), n is 2. In some embodiments of a compound of Formula (II) or (IIa), n is 1. In some embodiments of a compound of Formula (II) or (IIa), n is 0. In some embodiments of a compound of Formula (IIb)-(IIe), n' is 0-2. In some embodiments of a compound of Formula (IIb)-(IIe), n' is 0 or 1. In some embodiments of a compound of Formula (IIb)-(IIe), n' is 2. In some embodiments of a compound of Formula (IIb)-(IIe), n' is 1. In some embodiments of a compound of Formula (IIb)-(IIe), n' is 0.

In some embodiments of a compound of Formula (II) or (IIa)-(IIf), each $R^1$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (II) or (IIa)-(IIf), each $R^1$ is independently halogen, —CN, —OH, —OR$^a$, —NR$^c$R$^d$, $C_1$-$C_6$alkyl, or $C_1$-$C_6$haloalkyl. In some embodiments of a compound of Formula (II) or (IIa)-(IIf), each $R^1$ is independently halogen, —CN, $C_1$-$C_6$alkyl, or $C_1$-$C_6$haloalkyl. In some embodiments of a compound of Formula (II) or (IIa)-(IIf), each $R^1$ is independently halogen or —CN. In some embodiments of a compound of Formula (II) or (IIa)-(IIf), each $R^1$ is independently halogen. In some embodiments of a compound of Formula (II) or (IIa)-(IIf), each $R^1$ is fluoro or chloro. In some embodiments of a compound of Formula (II) or (IIa)-(IIf), each $R^1$ is —CN. In some embodiments of a compound of Formula (II) or (IIa)-(IIf), each $R^1$ is independently halogen, —CN, —OR$^a$, or —NR$^c$R$^d$. In some embodiments of a compound of Formula (II) or (IIa)-(IIf), each $R^1$ is independently —CN or —OR$^a$. In some embodiments of a compound of Formula (II) or (IIa)-(IIf), each $R^1$ is independently —CN or —NR$^c$R$^d$. In some embodiments of a compound of Formula (II) or (IIa)-(IIf), —OR$^a$ is —O-heterocycloalkyl, —O—$C_1$-$C_6$alkyl, —O—$C_1$-$C_6$haloalkyl, —O—$C_1$-$C_6$hydroxylalkyl, —O—$C_1$-$C_6$aminoalkyl. In some embodiments of a compound of Formula (II) or (IIa)-(IIf), —OR$^a$ is —O-heterocycloalkyl, wherein the heterocycloalkyl is a 5 or 6 membered ring. In some embodiments of a compound of Formula (II) or (IIa)-(IIf), —OR$^a$ is

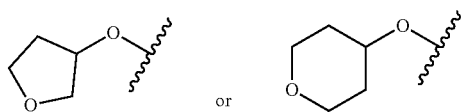

In some embodiments of a compound of Formula (II) or (IIa)-(IIf), —OR$^a$ is —O—$C_1$-$C_6$alkyl. In some embodiments of a compound of Formula (II) or (IIa)-(IIf), —OR$^a$ is —O—$C_1$-$C_6$haloalkyl. In some embodiments of a compound of Formula (II) or (IIa)-(IIf), —OR$^a$ is —O—$C_1$-$C_6$hydroxylalkyl. In some embodiments of a compound of Formula (II) or (IIa)-(IIf), —OR$^a$ is —O—$C_1$-$C_6$aminoalkyl. In some embodiments, each $R^1$ is independently —CN, —O-heterocycloalkyl, —O—$C_1$-$C_6$haloalkyl, —O—$C_1$-$C_6$hydroxylalkyl, or —O—$C_1$-$C_6$aminoalkyl. In some embodiments, each $R^1$ is independently —CN or —O— heterocycloalkyl. In some embodiments, each $R^1$ is independently —CN or —O—$C_1$-$C_6$haloalkyl. In some embodiments, each $R^1$ is independently —CN or —O—$C_1$-$C_6$hydroxylalkyl. In some embodiments, each $R^1$ is independently —CN or —O—$C_1$-$C_6$aminoalkyl. In some embodiments, at least one $R^1$ is —CN.

In some embodiments of a compound of Formula (II) or (IIa)-(IIf), $R^2$ is hydrogen or $C_1$-$C_6$alkyl. In some embodiments of a compound of Formula (II) or (IIa)-(IIf), $R^2$ is $C_1$-$C_6$alkyl.

In some embodiments of a compound of Formula (II) or (IIa)-(IIf), U is N. In some embodiments of a compound of Formula (II) or (IIa)-(IIf), U is CR$^U$.

In some embodiments of a compound of Formula (II) or (IIa)-(IIf), R$^U$ is hydrogen, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (II) or (IIa)-(IIf), R$^U$ is hydrogen, halogen, —CN, —C(=O)NR$^c$R$^d$, $C_1$-$C_6$alkyl, or $C_1$-$C_6$haloalkyl. In some embodiments of a compound of Formula (II) or (IIa)-(IIf), R$^U$ is hydrogen, —CN, or —C(=O)NR$^c$R$^d$. In some embodiments of a compound of Formula (II) or (IIa)-(IIf), R$^U$ is hydrogen or —CN. In some embodiments of a compound of Formula (II) or (IIa)-(IIf), R$^U$ is —CN.

In some embodiments of a compound of Formula (II),

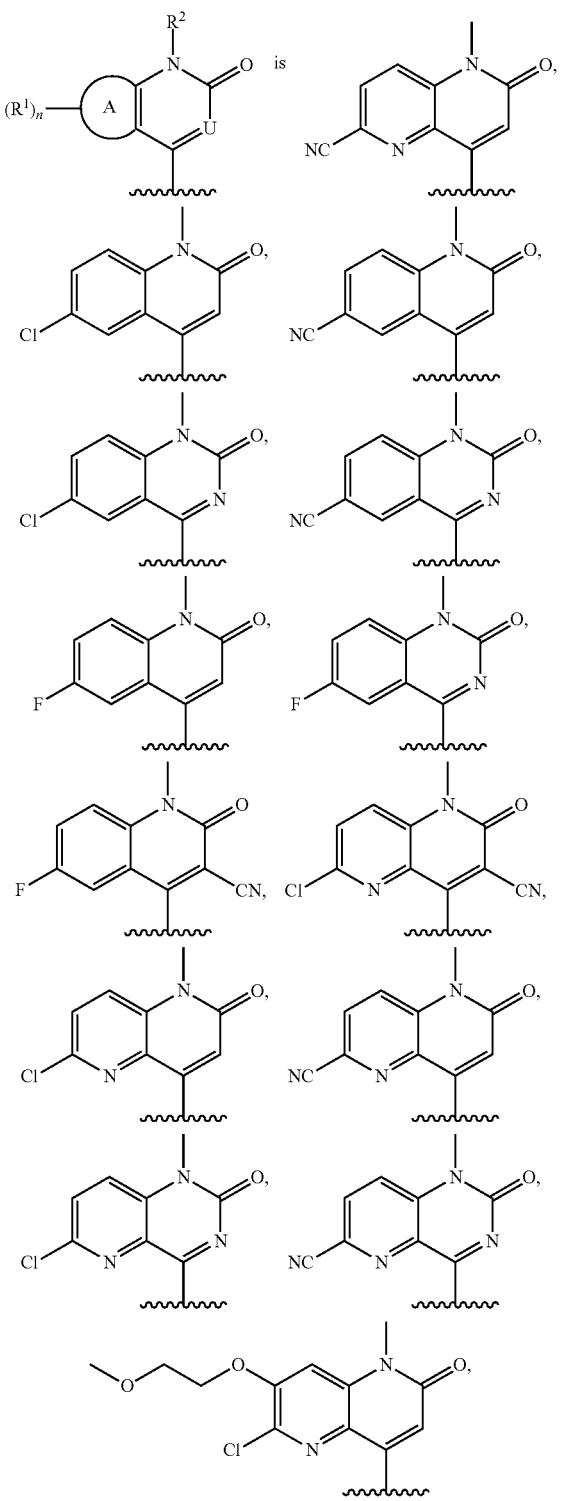

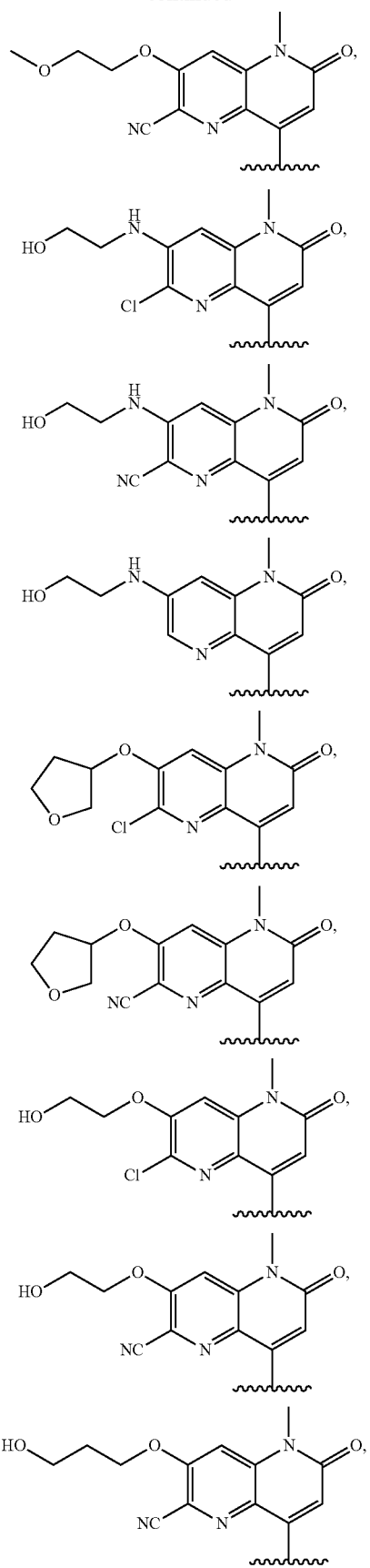
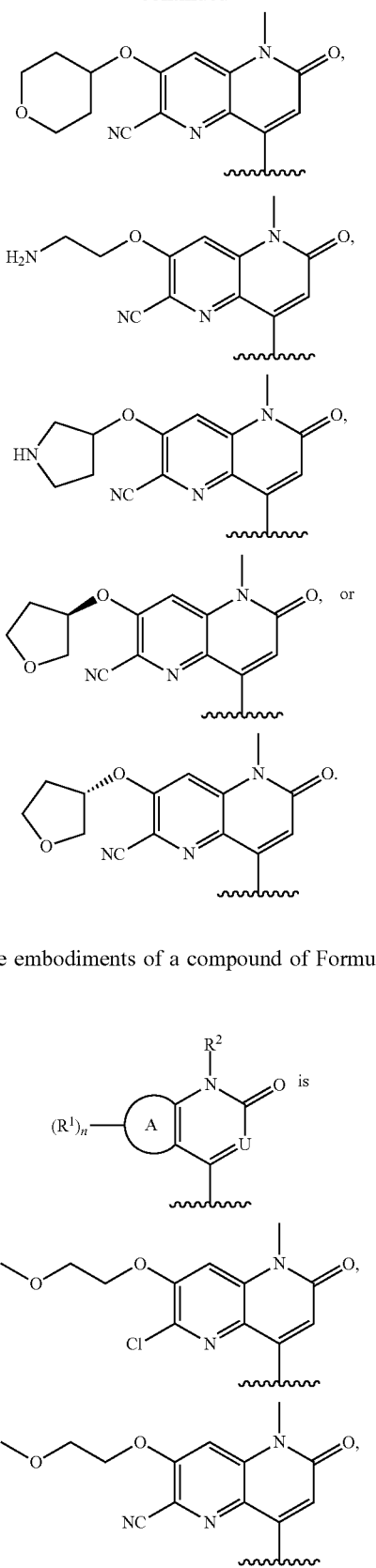
In some embodiments of a compound of Formula (II),
$$\text{is}$$

-continued
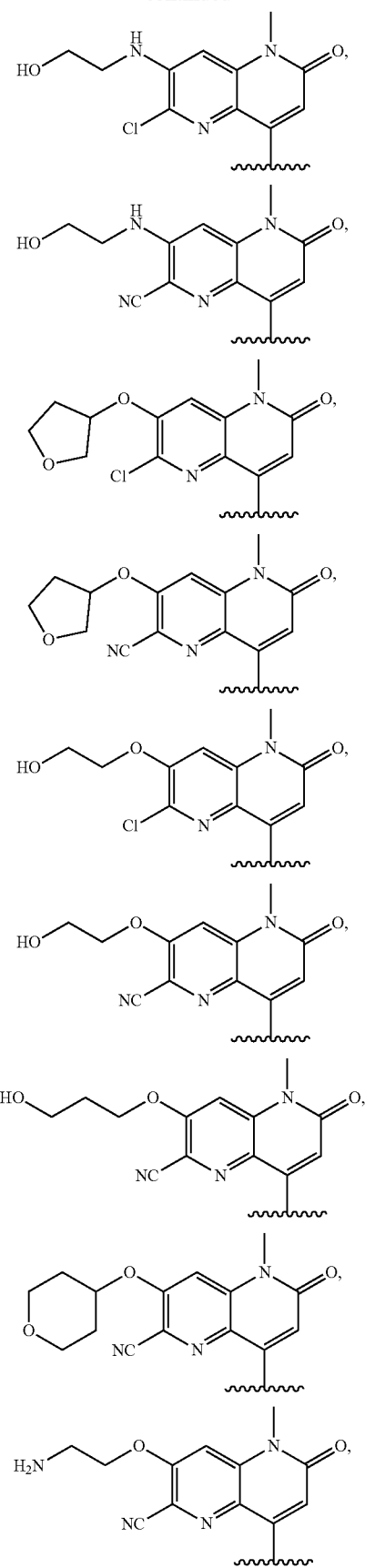
-continued
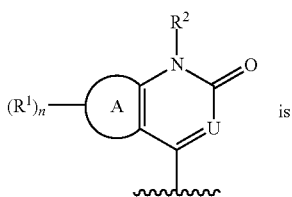
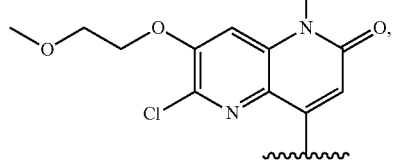
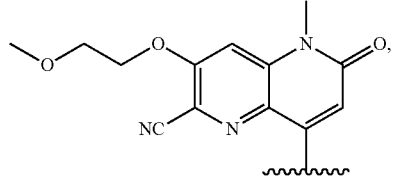
In some embodiments of a compound of Formula (II),
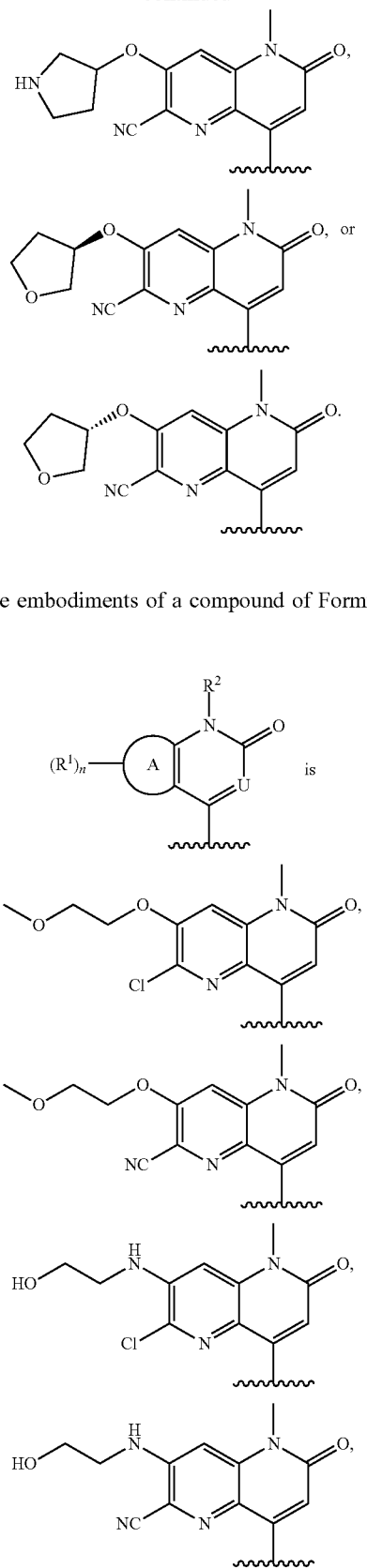

-continued
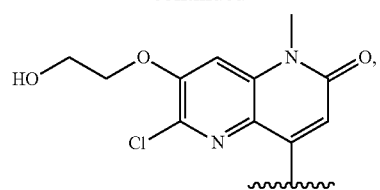
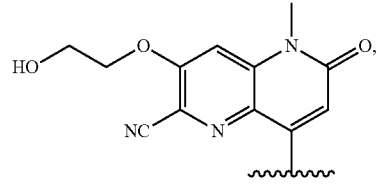
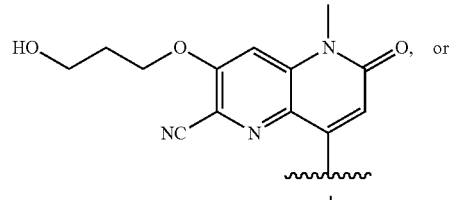
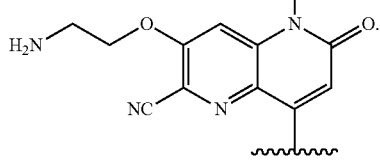
In some embodiments of a compound of Formula (II),
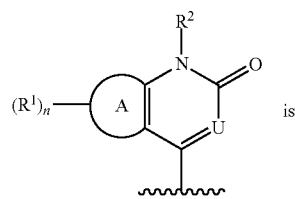 is
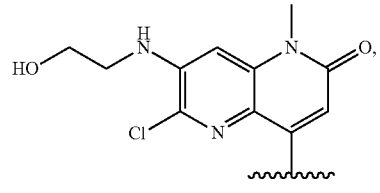
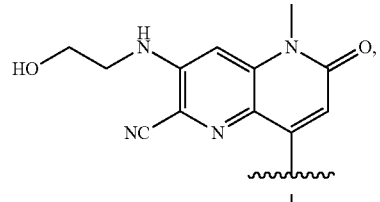
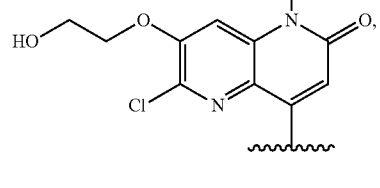
-continued
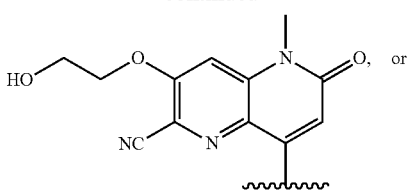
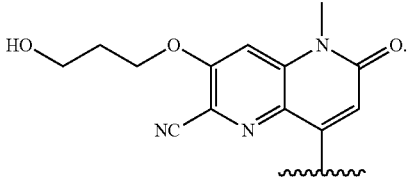
In some embodiments of a compound of Formula (II),
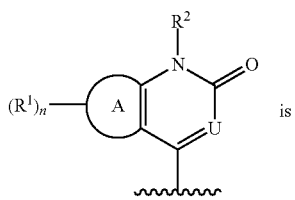 is
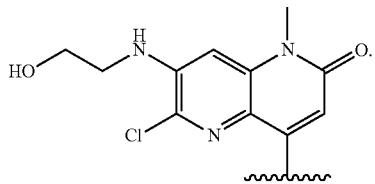
In some embodiments of a compound of Formula (II),
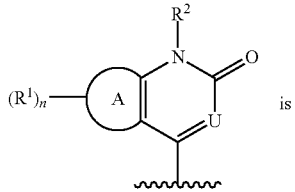 is
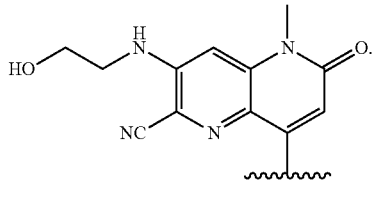
In some embodiments of a compound of Formula (II),
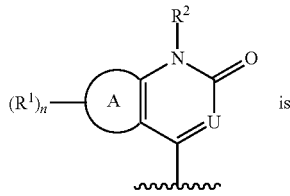 is -continued

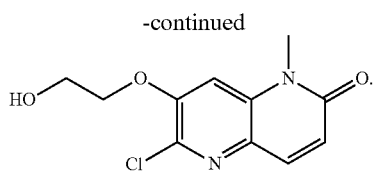

In some embodiments of a compound of Formula (II),

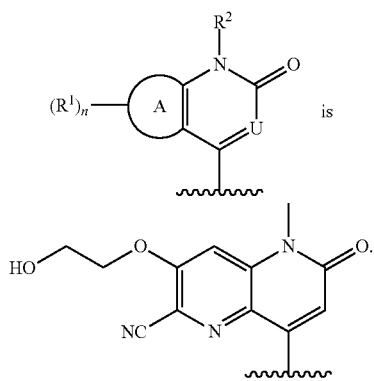

In some embodiments of a compound of Formula (II),

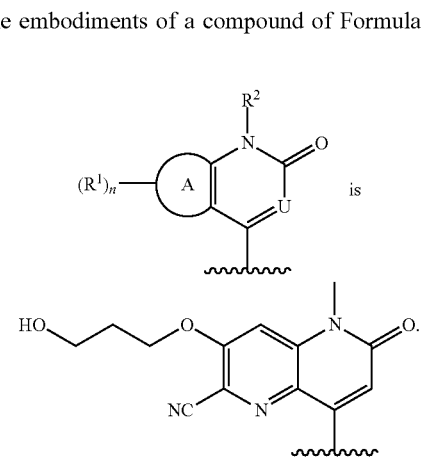

In some embodiments of a compound of Formula (II) or (IIa)-(IIf), Ring B is a bicyclic heterocycloalkyl. In some embodiments of a compound of Formula (II) or (IIa)-(IIf), Ring B is a bicyclic 6- to 10-membered heterocycloalkyl. In some embodiments of a compound of Formula (II) or (IIa)-(IIf), Ring B is a bicyclic 6- to 10-membered heterocycloalkyl comprising 1 to 3 heteroatoms selected from the group consisting of N, O, and S. In some embodiments of a compound of Formula (II) or (IIa)-(IIf), Ring B is a bicyclic 6- to 10-membered heterocycloalkyl comprising 1 to 3 heteroatoms selected from the group consisting of N and O. In some embodiments of a compound of Formula (II) or (IIa)-(IIf), Ring B is a bridged bicyclic ring. In some embodiments of a compound of Formula (II) or (IIa)-(IIf), Ring B is 3,8-diazabicyclo[3.2.1]octane or 2,5-diazabicyclo[2.2.2]octane. In some embodiments of a compound of Formula (II) or (IIa)-(IIf), Ring B is

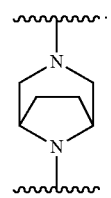

In some embodiments of a compound of Formula (II) or (IIa)-(IIf), each $R^3$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (II) or (IIa)-(IIf), each $R^3$ is independently $C_1$-$C_6$alkyl or $C_1$-$C_6$haloalkyl. In some embodiments of a compound of Formula (II) or (IIa)-(IIf), each $R^3$ is independently $C_1$-$C_6$alkyl. In some embodiments of a compound of Formula (II) or (IIa)-(IIf), each $R^3$ is independently methyl or ethyl.

In some embodiments of a compound of Formula (II) or (IIa)-(IIf), m is 0-4. In some embodiments of a compound of Formula (II) or (IIa)-(IIf), m is 0-3. In some embodiments of a compound of Formula (II) or (IIa)-(IIf), m is 0-2. In some embodiments of a compound of Formula (II) or (IIa)-(IIf), m is 2. In some embodiments of a compound of Formula (II) or (IIa)-(IIf), m is 1. In some embodiments of a compound of Formula (II) or (IIa)-(IIf), m is 2. In some embodiments of a compound of Formula (II) or (IIa)-(IIf), m is 3. In some embodiments of a compound of Formula (II) or (IIa)-(IIf), m is 4. In some embodiments of a compound of Formula (II) or (IIa)-(IIf), m is 5-8

In some embodiments of a compound of Formula (II) or (IIa)-(IIf), each $R^4$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (II) or (IIa)-(IIf), each $R^4$ is independently halogen, —CN, —OH, —OR$^a$, —NR$^c$R$^d$, $C_1$-$C_6$alkyl, or $C_1$-$C_6$haloalkyl. In some embodiments of a compound of Formula (II) or (IIa)-(IIf), each $R^4$ is independently halogen, $C_1$-$C_6$alkyl, or $C_1$-$C_6$haloalkyl. In some embodiments of a compound of Formula (II) or (IIa)-(IIf), each $R^4$ is independently halogen or $C_1$-$C_6$alkyl. In some embodiments of a compound of Formula (II) or (IIa)-(IIf), each $R^4$ is independently $C_1$-$C_6$alkyl. In some embodiments of a compound of Formula (II) or (IIa)-(IIf), each $R^4$ is methyl. In some embodiments of a compound of Formula (II) or (IIa)-(IIf), $R^4$ is F.

In some embodiments of a compound of Formula (II) or (IIa)-(IIf), p is 0-2. In some embodiments of a compound of Formula (II) or (IIa)-(IIf), p is 1 or 2. In some embodiments of a compound of Formula (II) or (IIa)-(IIf), p is 2. In some embodiments of a compound of Formula (II) or (IIa)-(IIf), p is 1. In some embodiments of a compound of Formula (II) or (IIa)-(IIf), p is 0.

In some embodiments of a compound of Formula (II) or (IIa)-(IIf),

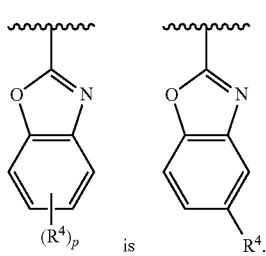

In some embodiments of a compound disclosed herein, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more R. In some embodiments of a compound disclosed herein, each $R^a$ is independently $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, each $R^a$ is independently $C_1$-$C_6$alkyl, $C_1$-$C_6$haloalkyl, or cycloalkyl, heterocycloalkyl. In some embodiments of a compound disclosed herein, each $R^a$ is independently $C_1$-$C_6$alkyl or $C_1$-$C_6$haloalkyl. In some embodiments of a compound disclosed herein, each $R^a$ is independently $C_1$-$C_6$alkyl.

In some embodiments of a compound disclosed herein, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more R. In some embodiments of a compound disclosed herein, each $R^b$ is independently hydrogen, $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, each $R^b$ is independently hydrogen, $C_1$-$C_6$alkyl, $C_1$-$C_6$haloalkyl, or cycloalkyl, heterocycloalkyl. In some embodiments of a compound disclosed herein, each $R^b$ is independently hydrogen, $C_1$-$C_6$alkyl or $C_1$-$C_6$haloalkyl. In some embodiments of a compound disclosed herein, each $R^b$ is independently hydrogen or $C_1$-$C_6$alkyl. In some embodiments of a compound disclosed herein, each $R^b$ is hydrogen. In some embodiments of a compound disclosed herein, each $R^b$ is independently $C_1$-$C_6$alkyl.

In some embodiments of a compound disclosed herein, each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more R. In some embodiments of a compound disclosed herein, each $R^c$ and $R^d$ are independently hydrogen, $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, each $R^c$ and $R^d$ are independently hydrogen, $C_1$-$C_6$alkyl, $C_1$-$C_6$haloalkyl, or cycloalkyl, heterocycloalkyl. In some embodiments of a compound disclosed herein, each $R^c$ and $R^d$ are independently hydrogen, $C_1$-$C_6$alkyl or $C_1$-$C_6$haloalkyl. In some embodiments of a compound disclosed herein, each R and $R^a$ are independently hydrogen or $C_1$-$C_6$alkyl. In some embodiments of a compound disclosed herein, each $R^c$ and $R^d$ are hydrogen. In some embodiments of a compound disclosed herein, each $R^c$ and $R^d$ are independently $C_1$-$C_6$alkyl.

In some embodiments of a compound disclosed herein, $R^c$ and $R^d$ are taken together with the atom to which they are attached to form a heterocycloalkyl optionally substituted with one or more R.

In some embodiments of a compound disclosed herein, each R is independently halogen, —CN, —OH, —$NH_2$, —$NHCH_3$, —$N(CH_3)_2$, —C(=O)$CH_3$, —C(=O)OH, —C(=O)O$CH_3$, $C_1$-$C_6$alkyl, $C_1$-$C_6$alkoxy, $C_1$-$C_6$haloalkyl, $C_1$-$C_6$hydroxyalkyl, $C_1$-$C_6$aminoalkyl, $C_1$-$C_6$heteroalkyl, or $C_3$-$C_6$cycloalkyl; or two R on the same atom form an oxo. In some embodiments of a compound disclosed herein, each R is independently halogen, —CN, —OH, —$NH_2$, —$NHCH_3$, —$N(CH_3)_2$, $C_1$-$C_6$alkyl, $C_1$-$C_6$alkoxy, $C_1$-$C_6$haloalkyl, $C_1$-$C_6$hydroxyalkyl, $C_1$-$C_6$aminoalkyl, $C_1$-$C_6$heteroalkyl, or $C_3$-$C_6$cycloalkyl; or two R on the same atom form an oxo. In some embodiments of a compound disclosed herein, each R is independently halogen, —CN, —OH, $C_1$-$C_6$alkyl, $C_1$-$C_6$alkoxy, or $C_1$-$C_6$haloalkyl; or two R on the same atom form an oxo. In some embodiments of a compound disclosed herein, each R is independently halogen, —CN, —OH, or $C_1$-$C_6$alkyl; or two R on the same atom form an oxo. In some embodiments of a compound disclosed herein, each R is independently halogen, —OH, or $C_1$-$C_6$alkyl. In some embodiments of a compound disclosed herein, each R is independently halogen or $C_1$-$C_6$alkyl. In some embodiments of a compound disclosed herein, each R is independently halogen.

In some embodiments of a compound disclosed herein, one or more of R, $R^1$, $R^2$, $R^3$, $R^4$, $R^U$, $R^T$, $R^a$, $R^b$, $R^c$, and $R^d$ groups comprise deuterium at a percentage higher than the natural abundance of deuterium.

In some embodiments of a compound disclosed herein, one or more $^1H$ are replaced with one or more deuteriums in one or more of the following groups R, $R^1$, $R^2$, $R^3$, $R^4$, $R^U$, $R^T$, $R^a$, $R^b$, $R^c$, and $R^d$.

In some embodiments of a compound disclosed herein, the abundance of deuterium in each of R, $R^1$, $R^2$, $R^3$, $R^4$, $R^U$, $R^T$, $R^a$, $R^b$, $R^c$, and $R^d$ is independently at least 1%, at least 10%, at least 20%, at least 30%, at least 40%, at least 50%, at least 60%, at least 70%, at least 80%, at least 90%, or 100% by molar.

In some embodiments of a compound disclosed herein, one or more $^1H$ of Ring A or Ring B are replaced with one or more deuteriums.

Any combination of the groups described above for the various variables is contemplated herein. Throughout the specification, groups and substituents thereof are chosen by one skilled in the field to provide stable moieties and compounds.

In some embodiments the compound disclosed herein, or a pharmaceutically acceptable salt thereof, is one of the compounds in Table 1.

TABLE 1

| Example | Structures |
|---|---|
| 1 | 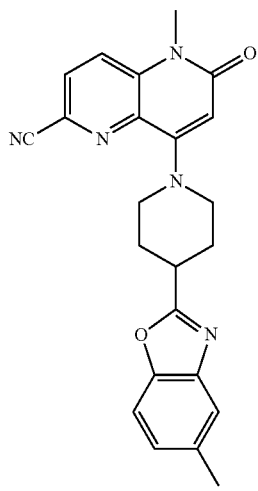 [SMILES: Cc1ccc2oc(C3CCN(c4cc(=O)n(C)c5ccc(C#N)nc45)CC3)nc2c1] |
| 2 | 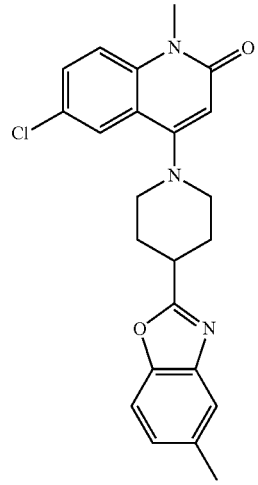 [SMILES: Cc1ccc2oc(C3CCN(c4cc(=O)n(C)c5ccc(Cl)cc45)CC3)nc2c1] |

TABLE 1-continued

| Example | Structures |
|---|---|
| 3 | 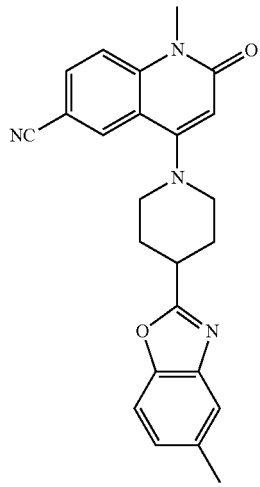 |
| 4 | 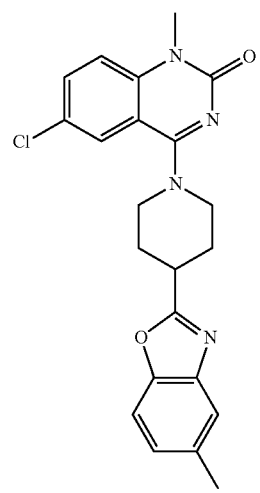 [SMILES: Cc1ccc2oc(C3CCN(c4nc(=O)n(C)c5ccc(Cl)cc45)CC3)nc2c1] |
| 5 | 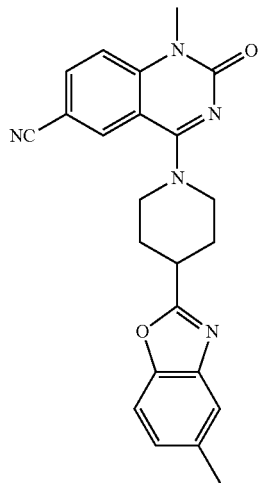 |

TABLE 1-continued
| Example | Structures |
|---|---|
| 6 | 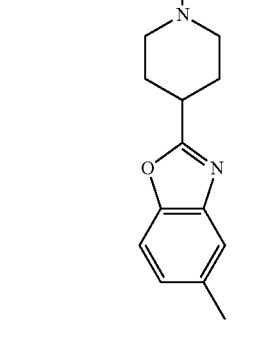 |
| 7 | 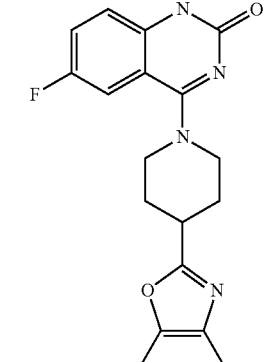 |
| 8 | 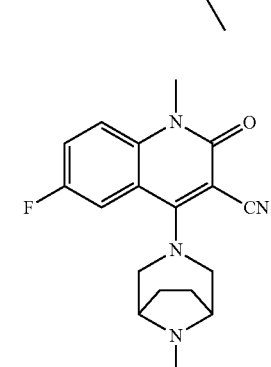 |
| 9 | 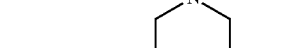 |
| 10 |  |
| 11 |  |

TABLE 1-continued

| Example | Structures |
|---|---|
| 12 | (structure) |
| 13 | (structure) |
| 14 | (structure) |
| 15 | (structure) |
| 16 | (structure) |
| 17 | (structure) |

TABLE 1-continued
| Example | Structures |
|---|---|
| 18 | 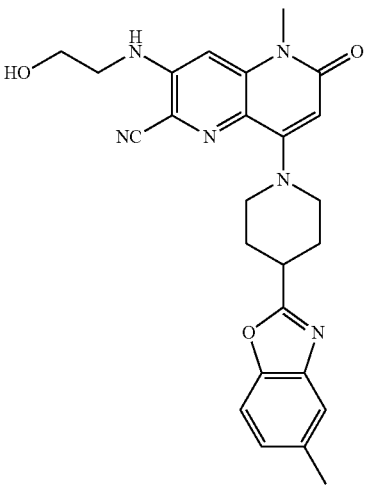 [SMILES: Cc1ccc2oc(C3CCN(c4cc(=O)n(C)c5cc(NCCO)c(C#N)nc45)CC3)nc2c1] |
| 19 | 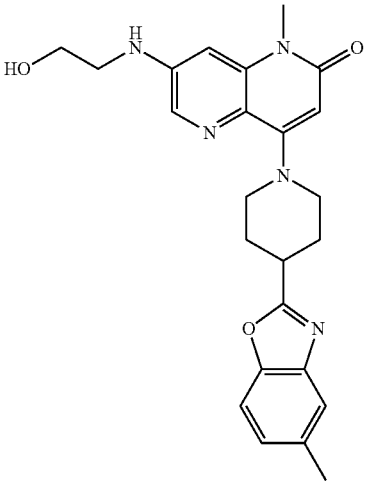 [SMILES: Cc1ccc2oc(C3CCN(c4cc(=O)n(C)c5cc(NCCO)cnc45)CC3)nc2c1] |
| 20 | 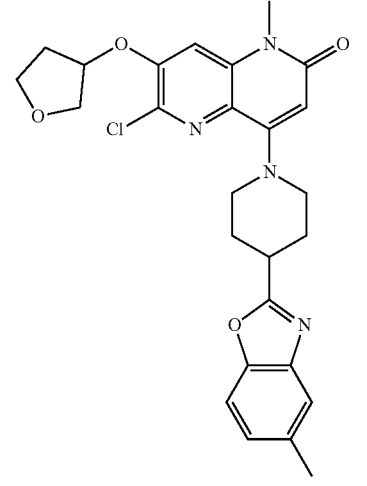 [SMILES: Cc1ccc2oc(C3CCN(c4cc(=O)n(C)c5cc(OC6CCOC6)c(Cl)nc45)CC3)nc2c1] |
| 21 | 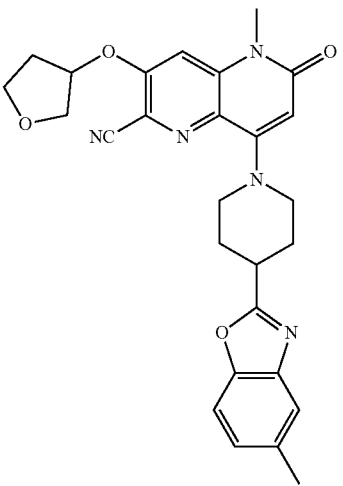 [SMILES: Cc1ccc2oc(C3CCN(c4cc(=O)n(C)c5cc(OC6CCOC6)c(C#N)nc45)CC3)nc2c1] |
| 22 | 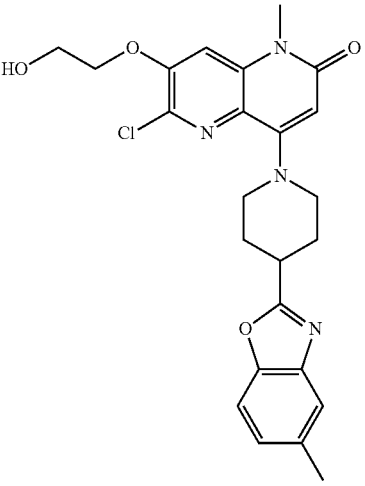 [SMILES: Cc1ccc2oc(C3CCN(c4cc(=O)n(C)c5cc(OCCO)c(Cl)nc45)CC3)nc2c1] |
| 23 | 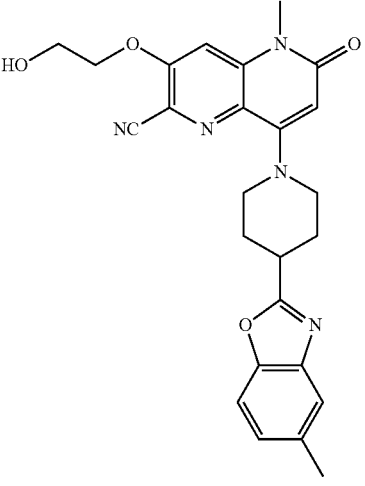 [SMILES: Cc1ccc2oc(C3CCN(c4cc(=O)n(C)c5cc(OCCO)c(C#N)nc45)CC3)nc2c1] |

TABLE 1-continued
| Example | Structures |
|---|---|
| 24 | 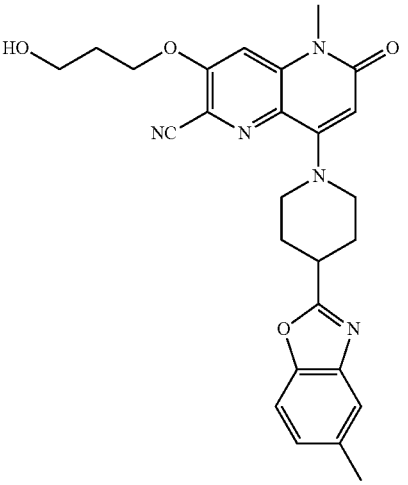 [SMILES: Cc1ccc2oc(C3CCN(c4cc(=O)n(C)c5cc(OCCCO)c(C#N)nc45)CC3)nc2c1] |
| 25 | 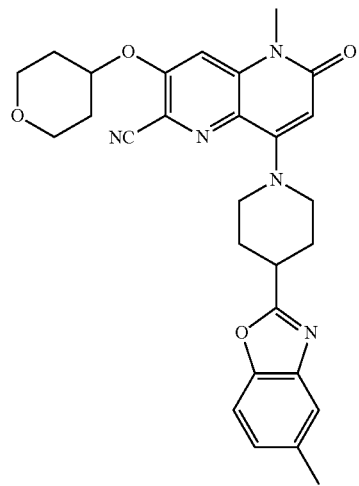 [SMILES: Cc1ccc2oc(C3CCN(c4cc(=O)n(C)c5cc(OC6CCOCC6)c(C#N)nc45)CC3)nc2c1] |
| 26 | 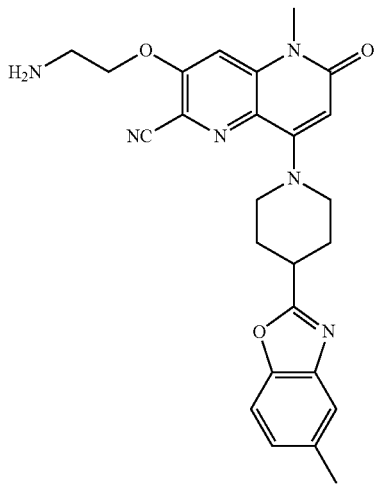 [SMILES: Cc1ccc2oc(C3CCN(c4cc(=O)n(C)c5cc(OCCN)c(C#N)nc45)CC3)nc2c1] |
| 27 | 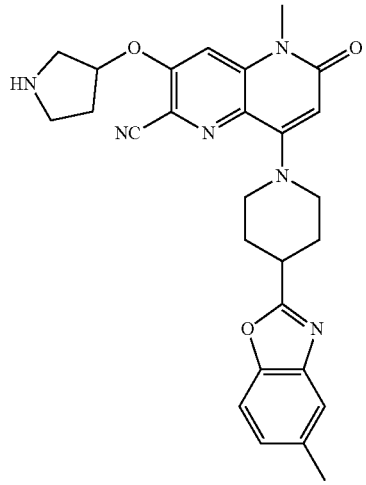 [SMILES: Cc1ccc2oc(C3CCN(c4cc(=O)n(C)c5cc(OC6CCNC6)c(C#N)nc45)CC3)nc2c1] |
| 28 | 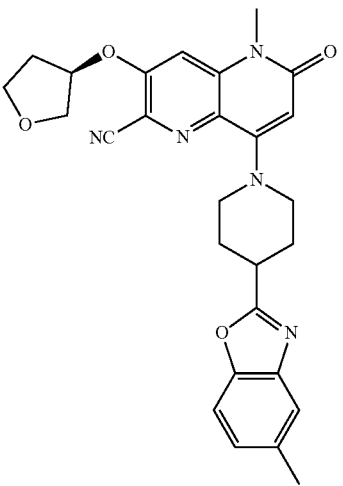 [SMILES: Cc1ccc2oc(C3CCN(c4cc(=O)n(C)c5cc(O[C@@H]6CCOC6)c(C#N)nc45)CC3)nc2c1] |
| 29 | |

TABLE 1-continued

| Example | Structures |
|---------|------------|
| 30 | (structure: 1,5-naphthyridin-2(1H)-one with N-methyl, 7-(2-hydroxyethoxy), 6-cyano, 4-substituted with tetrahydropyridine linked to 5-methylbenzoxazole) |

In some embodiments the compound disclosed herein, or a pharmaceutically acceptable salt thereof, is one of the compounds in Table 2.

TABLE 2

| Structure |
|-----------|
| (structure: 1,5-naphthyridin-2(1H)-one with N-methyl, 6-chloro, 4-substituted with 2,6-diazaspiro-containing piperidine linked to 5-methylbenzoxazole) |

Further Forms of Compounds Disclosed Herein
Isomers Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Isotopically Enriched Compounds

Unless otherwise stated, compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1H$ (protium), $^2H$ (deuterium), and $^3H$ (tritium). Protium is the most abundant isotope of hydrogen in nature. Enriching for deuterium may afford some therapeutic advantages, such as increased in vivo half-life and/or exposure, or may provide a compound useful for investigating in vivo routes of drug elimination and metabolism.

For example, the compounds described herein may be artificially enriched in one or more particular isotopes. In some embodiments, the compounds described herein may be artificially enriched in one or more isotopes that are not predominantly found in nature. In some embodiments, the compounds described herein may be artificially enriched in one or more isotopes selected from deuterium ($^2H$), tritium ($^3H$), iodine-125 ($^{125}I$) or carbon-14 ($^{14}C$). In some embodiments, the compounds described herein are artificially enriched in one or more isotopes selected from $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{131}I$, and $^{125}I$. In some embodiments, the abundance of the enriched isotopes is independently at least 1%, at least 10%, at least 20%, at least 30%, at least 40%, at least 50%, at least 60%, at least 70%, at least 80%, at least 90%, or 100% by molar.

In some embodiments, the compound is deuterated in at least one position. In some embodiments, the compounds disclosed herein have some or all of the $^1H$ atoms replaced with $^2H$ atoms.

The methods of synthesis for deuterium-containing compounds are known in the art and include, by way of non-limiting example only, the procedure described in U.S. Pat. Nos. 5,846,514 and 6,334,997, and the following synthetic methods. For example, deuterium substituted compounds may be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6 (10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64 (1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate, undecanoate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Disclosed herein are methods of treating a disease modulated by DGK in a subject in need thereof, comprising administering to the subject a therapeutically affective amount of a compound, or a pharmaceutically acceptable salt thereof, disclosed herein. Disclosed herein are methods of treating a disease in a subject in need thereof, comprising administering to the subject a therapeutically affective amount of a compound, or a pharmaceutically acceptable salt thereof, disclosed herein. In some embodiments, the disease is cancer.

Disclosed herein are methods of treating a disease modulated by DGKalpha in a subject in need thereof, comprising administering to the subject a therapeutically affective amount of a compound, or a pharmaceutically acceptable salt thereof, disclosed herein. In some embodiments, the disease is cancer or a viral infection.

In some embodiments, the cancer is a solid tumor. In some embodiments, the cancer is a hematological cancer. In some embodiments, the cancer is breast cancer, cervical cancer, colon cancer, head and neck cancer, leukemia, liver cancer, lung cancer, lymphoma, melanoma, ovarian cancer, pancreatic cancer, prostate cancer, renal cancer, thyroid cancer, or urinary track cancer.

In some embodiments, the viral infection is an HIV infection, an hepatitis B virus infection, an hepatitis C virus infection, a human papilloma virus infection, a cytomegalovirus infection, herpes simplex virus infection, Epstein-Barr virus infection, or a varicella zoster virus infection.

Disclosed herein is a method of inhibiting the activity of at least one of diacylglycerol kinase comprising administering to the subject a therapeutically affective amount of a compound, or a pharmaceutically acceptable salt thereof, disclosed herein. In some embodiments, the diacylglycerol kinase is diacylglycerol kinase alpha (DGKalpha). In some embodiments, the diacylglycerol kinase is diacylglycerol kinase zeta (DGKzeta). Disclosed herein is a method of modulating the activity of at least one of diacylglycerol kinase selected from diacylglycerol kinase alpha (DGKalpha) and diacylglycerol kinase zeta (DGKzeta), in a subject in need thereof, the method comprising administering to the subject a compound, or a pharmaceutically acceptable salt thereof, disclosed herein. Disclosed herein is a method of modulating the activity of diacylglycerol kinase alpha (DGKalpha), in a subject in need thereof, the method comprising administering to the subject a compound, or a pharmaceutically acceptable salt thereof, disclosed herein. In some embodiments, the subject has a disease described herein. In some embodiments, the subject has cancer.

Dosing

In certain embodiments, the compositions containing the compound(s) described herein are administered for therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage, or the frequency of administration, or both, is reduced, as a function of the symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In some embodiments, doses employed for adult human treatment are typically in the range of 0.01 mg-5000 mg per day. In some embodiments, the daily dosages appropriate for the compound described herein, or a pharmaceutically acceptable salt thereof, are from about 0.01 to about 50 mg/kg per body weight. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In some embodiments, the compounds described herein are administered to animals.

In another aspect, provided herein are pharmaceutical compositions comprising a compound described herein, or a pharmaceutically acceptable salt thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Combination

Disclosed herein are methods of treating a disease or disorder associated with DGKalpha using a compound disclosed herein, or a pharmaceutically acceptable salt thereof, in combination with an additional therapeutic agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

In some embodiments, the additional therapeutic agent is an anti-cancer agent. In some embodiments, the anti-cancer agent is an immune checkpoint inhibitor. In some embodiments, the immune checkpoint inhibitor is an anti-CTLA-4 (Cytotoxic T lymphocyte antigen 4) antibody, an anti-PD-1 (Programmed death receptor 1) antibody, or an anti-PD-L1 (Programmed death ligand 1) antibody.

In some embodiments, the additional therapeutic agent is an anti-viral agent.

EXAMPLES

Example 1: 5-methyl-8-(4-(5-methylbenzo[d]oxazol-2-yl)piperidin-1-yl)-6-oxo-5,6-dihydro-1,5-naphthyridine-2-carbonitrile

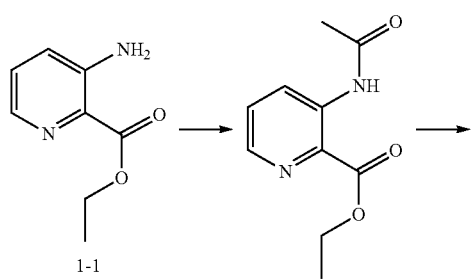

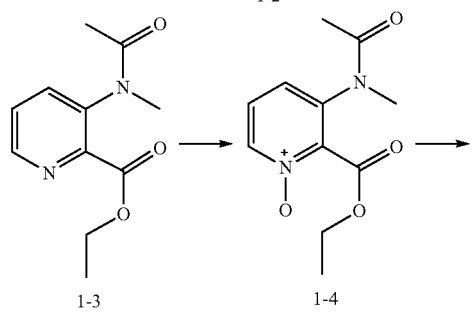

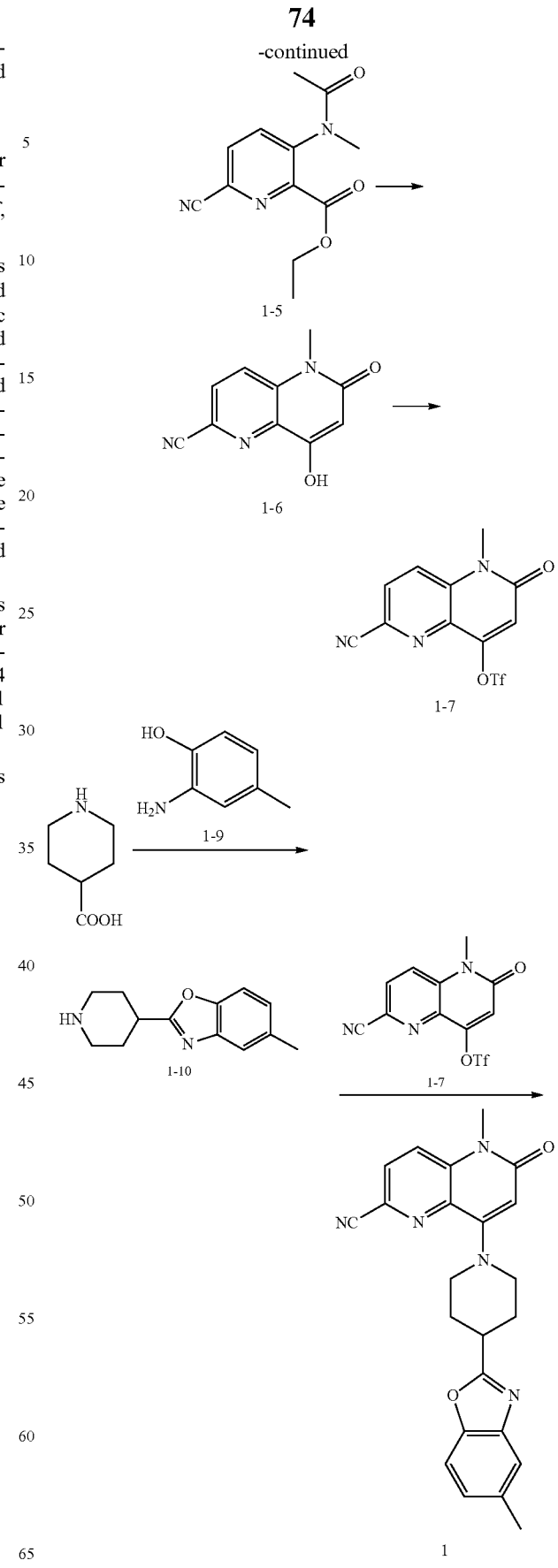

To a mixture of compound 1-1 (10 g, 60.18 mmol) in THF (100 mL) was added Ac₂O (55.29 g, 541.58 mmol) at room temperature. The reaction mixture was stirred at 60° C. under N₂ for 18 h. After cooling to room temperature, the mixture was concentrated under reduced pressure. To the resulting residue was added petroleum ether (500 mL) and the suspension was stirred for 30 min at 20° C. The mixture was filtered and the filter cake was rinsed with petroleum ether (500 mL). The filter cake was collected and dried under vacuum to give compound 1-2. MS (ESI) m/z (M+H)⁺=209.0

To a mixture of compound 1-2 (10.7 g, 51.39 mmol) and cesium carbonate (25.11 g, 77.08 mmol) in DMF (200 mL) was added methyl iodide (10.94 g, 77.08 mmol) at 20° C. The mixture was stirred at room temperature for 18 h. The reaction mixture was diluted with water (500 mL) and extracted with DCM (3×200 mL). The combined organic layers were washed with brine (2×100 mL), dried over Na₂SO₄, filtered, and concentrated under reduced pressure. To the resulting residue was added petroleum ether (500 mL) and the suspension was stirred for 30 min at 20° C. The mixture was filtered and the filter cake was rinsed with petroleum ether (500 mL). The filter cake was collected and dried under reduced pressure to give compound 1-3. MS (ESI) m/z (M+H)⁺=223.1.

To a mixture of compound 1-3 (4 g, 18.00 mmol) in DCM (200 mL) at 0-5° C. was added urea hydrogen peroxide (2.54 g, 27.0 mmol), followed by trifluoroacetic anhydride (5.67 g, 27.00 mmol) slowly over 40 min. The reaction mixture solidified during the trifluoroacetic anhydride addition. After completion of the addition, the reaction mixture was stirred at 20° C. for 18 h. The reaction mixture was quenched with 10% NaHCO₃ solution (100 mL) and extracted with DCM (3×100 mL). The combined organic layers were washed with brine (2×100 mL), dried over Na₂SO₄, and concentrated under reduced pressure to give compound 1-4, which was used in the next step without further purification. MS (ESI) m/z (M+H)⁺=239.1.

To a mixture of compound 1-4 (1.8 g, 7.56 mmol) in DCM (150 mL) at 20° C. was added trimethylsilyl cyanide (1.23 g, 11.33 mmol). The reaction mixture was stirred for 10 min and cooled to −10° C. Next, benzoyl chloride (1.59 g, 11.33 mmol) was added through a 10 mL addition funnel over 15 min followed by TEA (1.15 g, 11.33 mmol) through a 10 mL addition funnel slowly over 20 min. The reaction mixture was stirred at room temperature for 18 h. The reaction mixture was quenched with 10% NaHCO₃ solution (100 mL) and extracted with DCM (3×100 mL). The combined organic layers were washed with brine (2×100 mL), dried over Na₂SO₄, filtered, and concentrated under reduced pressure. The resulting residue was purified by column chromatography on silica gel to give compound 1-5. MS (ESI) m/z (M+H)⁺=248.1.

To a mixture of compound 1-5 (1.6 g, 6.47 mmol) in tetrahydrofuran (100 mL) was added KHMDS (7.76 mL, 7.76 mmol, 1 M) at −78° C. over 10 min under N₂. The reaction mixture was stirred for 15 min. The reaction mixture was slowly warmed to 20° C. over 30 min and then stirred for another 18 h. The reaction mixture was cooled to 0° C. The reaction was quenched with saturated sodium bicarbonate solution (70 mL). The mixture was washed with ethyl acetate (2×100 mL). The aqueous layer was collected and acidified with 1.5 N HCl to adjust pH to ~3.0. The mixture was stirred for 15 min and the precipitate formed. The precipitate was collected by filtration to give compound 1-6. MS (ESI) m/z (M+H)⁺=202.1.

To a solution of compound 1-6 (920 mg, 4.57 mmol) in DMF (50 mL) was added Et₃N (1388 mg, 5.49 mmol) and 1,1,1-trifluoro-N-phenyl-N-((trifluoromethyl)sulfonyl) methanesulfonamide (1.96 g, 5.49 mmol). The mixture was stirred at 20° C. for 18 h under N₂. The mixture was poured into water (100 mL) and extracted with DCM (30 mL×3), dried over Na₂SO₄, filtered, and concentrated under reduced pressure. The residue was purified by flash column chromatography to give compound 1-7. MS (ESI) m/z (M+H)⁺=334.2.

To the mixture of compound 1-8 (5 g, 38.71 mmol) and compound 1-9 (5.01 g, 40.65 mmol) were added PPA (25 g, 73.98 mmol), and the mixture was stirred at 180° C. for 2 hours. After cooling to 20° C., the reaction was quenched with water. The mixture was adjusted to pH=12 with 50% potassium hydroxide aqueous solution and then extracted with methylene chloride (2×200 mL). The organic layer was washed with saturated brine and dried over Na₂SO₄, and evaporated under reduced pressure to afford compound 1-10. MS (ESI) m/z (M+H)⁺=217.0.

To a solution of compound 1-7 (80 mg, 0.230 mmol) in DMSO (10 mL) was added compound 1-10 (59.56 mg, 0.275 mmol) and ethyldiisopropylamine (0.190 mL, 1.148 mmol). The reaction mixture was stirred at 130° C. for 3 h. The mixture was concentrated under reduced pressure. The residue was purified by preparative HPLC to give example 1. MS (ESI) m/z (M+H)⁺=400.2. ¹H NMR (400 MHz, DMSO) δ 8.17 (d, J=8.8 Hz, 1H), 8.08 (d, J=8.9 Hz, 1H), 7.55 (d, J=8.3 Hz, 1H), 7.50 (s, 1H), 7.17 (d, J=8.3 Hz, 1H), 6.16 (s, 1H), 4.05 (d, J=12.7 Hz, 2H), 3.54 (s, 3H), 3.40-3.35 (m, 1H), 3.15 (t, J=11.1 Hz, 2H), 2.41 (s, 3H), 2.27-2.17 (m, 2H), 2.10-1.98 (m, 2H).

Example 2: 6-chloro-1-methyl-4-(4-(5-methylbenzo[d]oxazol-2-yl)piperidin-1-yl)quinolin-2(1H)-one

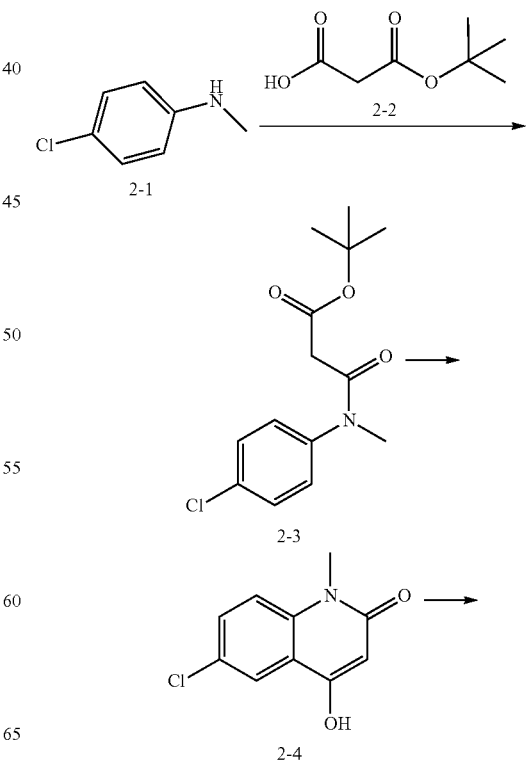

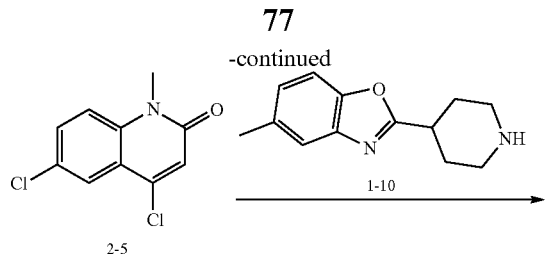

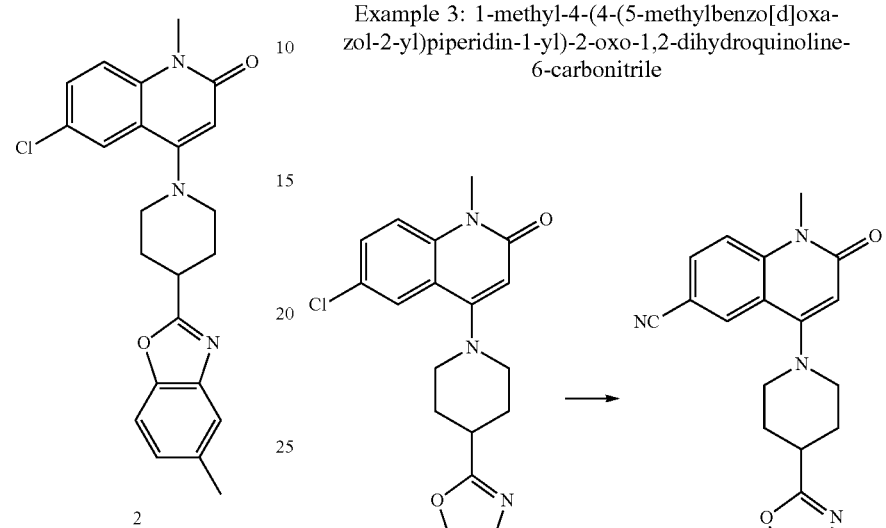

To a solution of compound 2-1 (5 g, 35.31 mmol) in DCM (200 mL) was added compound 2-2 (5.77 g, 36.02 mmol) at 0° C., then EDCI (6.90 g, 36.02 mmol) was added in several batches. The reaction mixture was stirred at 0° C. for 1 h. The mixture was washed with 1 M NaOH (50 mL×3), then washed with 1 M HCl (50 mL×3). The organic layer was dried over $Na_2SO_4$, filtered, and concentrated under reduced pressure to give compound 2-3, which was used in the next step without further purification. MS (ESI) m/z $(M-56+H)^+=228.1$.

To a solution of compound 2-3 (10 g, 32.72 mmol) in methanesulfonic acid (50 mL) was added phosphorus pentoxide (6.97 g, 49.08 mmol). The reaction mixture was stirred at 60° C. for 0.5 h and then at 110° C. for another 0.5 h. The mixture was cooled to 20° C. and poured into ice-water (150 mL). The mixture was stirred for 0.5 h and then filtered. The filter cake was dried under reduced pressure to give compound 2-4, which was used in the next step without further purification. MS (ESI) m/z $(M+CH_3CN+H)^+=251.1$.

A mixture of compound 2-4 (2 g, 9.14 mmol) in $POCl_3$ (30 mL) was stirred at 100° C. for 3 h. The mixture was evaporated and poured into ice-water (20 mL). The mixture was adjusted to pH=8.0 with saturated sodium bicarbonate solution and extracted with DCM (100 mL×3). The combined organic layers were dried over $Na_2SO_4$, filtered, and concentrated under reduced pressure to give compound 2-5, which was used in the next step without further purification. MS (ESI) m/z $(M+H)^+=228.1$ To a mixture of compound 2-5 (100 mg, 0.438 mmol) and compound 1-10 (142.25 mg, 0.658 mmol) in DMSO (4 mL) was added DIEA (0.362 mL, 2.192 mmol). The mixture was stirred at 130° C. for 5 h under $N_2$. The mixture was quenched with $H_2O$ (15 mL) and extracted with EtOAc (2×15 mL). The combined organic layers were washed with brine (3×30 mL), dried over $Na_2SO_4$, filtered, and concentrated under reduced pressure to give crude product. The residue was purified by prep-HPLC to give example 2. MS (ESI) m/z $(M+H)^+=408.1$. $^1H$ NMR (400 MHz, DMSO) δ 7.71-7.62 (m, 2H), 7.60-7.48 (m, 3H), 7.19 (d, J=8.3 Hz, 1H), 6.13 (s, 1H), 3.56 (s, 3H), 3.46-3.38 (m, 2H), 3.31-3.22 (m, 1H), 3.01-2.87 (m, 2H), 2.43 (s, 3H), 2.32-2.24 (m, 2H), 2.18-2.06 (m, 2H).

Example 3: 1-methyl-4-(4-(5-methylbenzo[d]oxazol-2-yl)piperidin-1-yl)-2-oxo-1,2-dihydroquinoline-6-carbonitrile

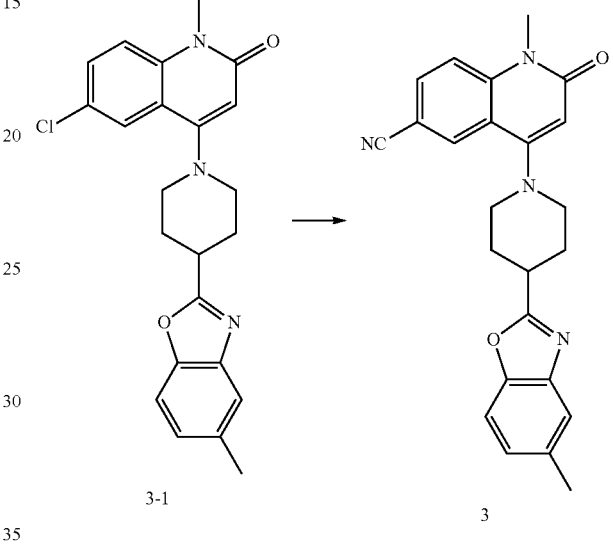

To a mixture of compound 3-1 (example 2) (30 mg, 0.057 mmol) in DMA (1 mL) was added $Zn(CN)_2$ (13.44 mg, 0.114 mmol), Zn (3.74 mg, 0.057 mmol), $Pd_2(dba)_3$ (10.48 mg, 0.011 mmol), $Zn(OAc)_2$ (2.10 mg, 0.011 mmol) and DPPF (6.35 mg, 0.011 mmol). The reaction mixture was stirred at 150° C. for 1 h under microwave in a sealed tube. The mixture was diluted with DCM (50 mL) and filtered, then the filtrate was concentrated under reduced pressure. The residue was purified by prep-HPLC to give example 3. MS (ESI) m/z $(M+H)^+=399.3$. $^1H$ NMR (400 MHz, DMSO) δ 8.14 (d, J=1.6 Hz, 1H), 8.00 (dd, J=8.8, 1.7 Hz, 1H), 7.68 (d, J=8.9 Hz, 1H), 7.57 (d, J=8.3 Hz, 1H), 7.52 (s, 1H), 7.19 (d, J=8.3 Hz, 1H), 6.16 (s, 1H), 3.58 (s, 3H), 3.44 (d, J=12.3 Hz, 2H), 2.95 (t, J=10.8 Hz, 2H), 2.42 (s, 3H), 2.37-2.10 (m, 5H).

Example 4: 6-chloro-1-methyl-4-(4-(5-methylbenzo[d]oxazol-2-yl)piperidin-1-yl)quinazolin-2(1H)-one

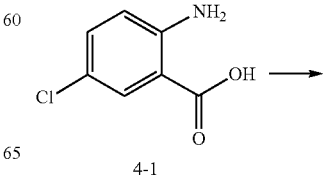

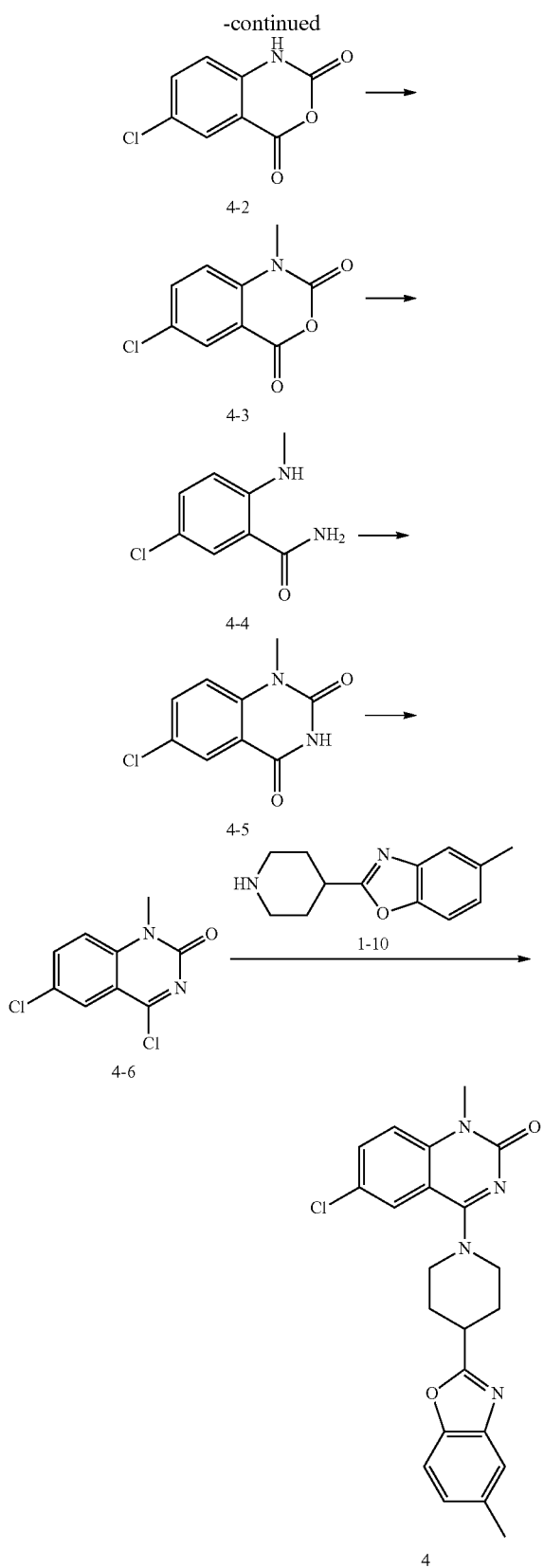

To a mixture of compound 4-1 (10 g, 58.28 mmol) in dioxane (100 mL) was added trichloromethyl chloromethanoate (86.47 g, 437.11 mmol). The reaction mixture was stirred at 110° C. for 4 h. The reaction mixture was filtered and the filter cake was dried under reduced pressure to give compound 4-2, which was used in the next step without further purification. $^1$H NMR (400 MHz, DMSO) δ 11.86 (s, 1H), 7.87 (d, J=0.8 Hz, 1H), 7.78 (dd, J=8.8, 2.3 Hz, 1H), 7.16 (d, J=8.8 Hz, 1H).

To a mixture of compound 4-2 (10 g, 50.62 mmol) in DMF (100 mL) was added Na$_2$CO$_3$ (6.44 g, 60.74 mmol) and CH$_3$I (5 mL, 75.91 mmol). The reaction mixture was stirred at 20° C. for 12 h under N$_2$. The mixture was quenched with water (300 mL). The reaction mixture was filtered and the filter cake was dried under reduced pressure to give compound 4-3, which was used in the next step without further purification. $^1$H NMR (400 MHz, DMSO) δ 7.96 (d, J=1.6 Hz, 1H), 7.93-7.87 (m, 1H), 7.48 (d, J=8.8 Hz, 1H), 3.46 (s, 3H).

To a mixture of compound 4-3 (1500 mg, 7.09 mmol) in THF (10 mL) was added ammonium hydroxide (0.546 mL, 14.178 mmol). The mixture was stirred at 60° C. for 2 h. The reaction mixture was diluted with EA (30 ml). The organic layer was washed with water (30 mL) and saturated brine (2×30 mL), dried over Na$_2$SO$_4$, filtered, and concentrated under reduced pressure to give compound 4-4, which was used in the next step without further purification. MS (ESI) m/z (M+H)$^+$=185.2. $^1$H NMR (400 MHz, DMSO) δ 7.92 (s, 1H), 7.65 (d, J=2.4 Hz, 1H), 7.30 (dd, J=8.9, 2.4 Hz, 1H), 6.64 (d, J=9.2 Hz, 1H), 2.77 (s, 3H).

To a mixture of compound 4-4 (1000 mg, 5.417 mmol) in DMF (15 mL) was added NaH (1083.31 mg, 27.08 mmol, 60% in mineral oil) at 0° C. under N$_2$. The reaction mixture was stirred at 0° C.-20° C. for 1 h under N$_2$. CDI (1317.44 mg, 8.125 mmol) was added to the mixture. The mixture was stirred at 70° C. for 2 h under N$_2$. The mixture was diluted with DCM (15 ml), adjusted to pH=4-5 with 1 M HCl, and precipitate formed. The mixture was filtered and the filter cake was washed with H$_2$O (20 mL) and dried under reduced pressure to give compound 4-5, which was used in the next step without further purification. $^1$H NMR (400 MHz, DMSO) δ 11.70 (s, 1H), 7.92 (t, J=7.6 Hz, 1H), 7.80 (dd, J=8.8, 2.4 Hz, 1H), 7.46 (d, J=9.2 Hz, 1H), 3.43 (s, 3H).

To a mixture of compound 4-5 (100 mg, 0.475 mmol) in toluene (5 mL) was added POCl$_3$ (0.221 mL, 2.374 mmol) and DIEA (0.392 mL, 2.374 mmol). The reaction mixture was stirred at 110° C. for 3 h. The mixture was concentrated under reduced pressure to give compound 4-6, which was used for the next step without further purification. MS (ESI) m/z (M+H)$^+$=228.9.

To a mixture of compound 4-6 (100 mg, 0.437 mmol) and compound 1-10 in dioxane (5 mL) was added DIEA (0.072 mL, 0.437 mmol). The mixture was stirred at 90° C. for 2 h under N$_2$. The reaction mixture was concentrated under reduced pressure. The residue was purified by preparative HPLC to give example 4. MS (ESI) m/z (M+H)$^+$=409.1. $^1$H NMR (400 MHz, DMSO) δ 7.80-7.73 (m, 2H), 7.56 (d, J=8.4 Hz, 1H), 7.53-7.42 (m, 2H), 7.18 (d, J=8.4 Hz, 1H), 4.21 (d, J=13.2 Hz, 2H), 3.46 (s, 3H), 3.44-3.37 (m, 3H), 2.41 (s, 3H), 2.28-2.16 (m, 2H), 2.08-1.92 (m, 2H).

Example 5: 1-methyl-4-(4-(5-methylbenzo[d]oxazol-2-yl)piperidin-1-yl)-2-oxo-1,2-dihydroquinazoline-6-carbonitrile

Example 6: 6-fluoro-1-methyl-4-(4-(5-methylbenzo[d]oxazol-2-yl)piperidin-1-yl)quinolin-2(1H)-one

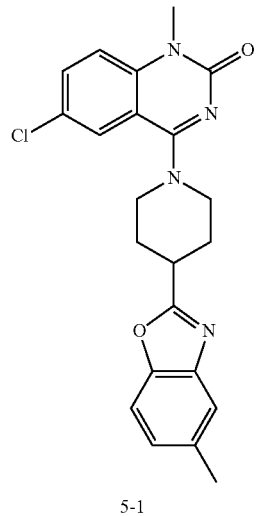

5-1

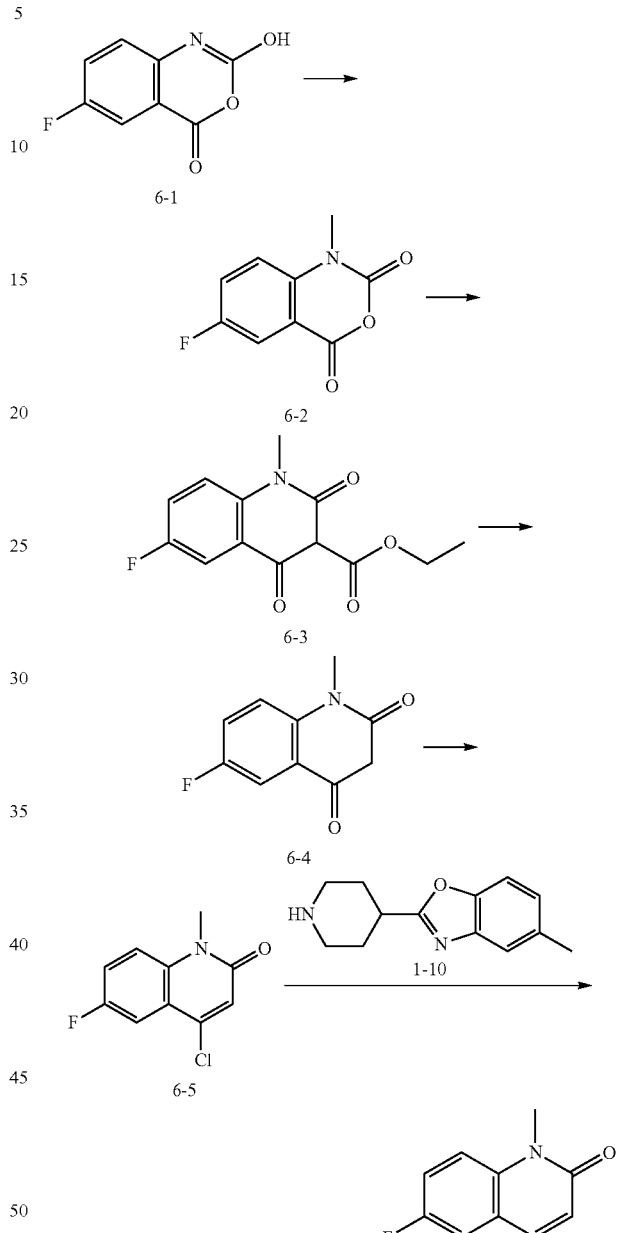

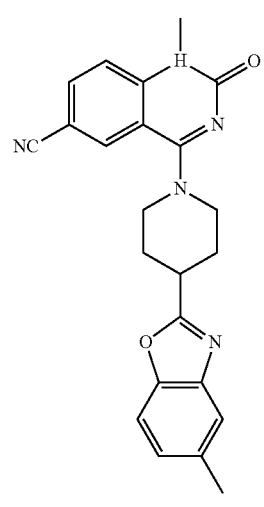

5

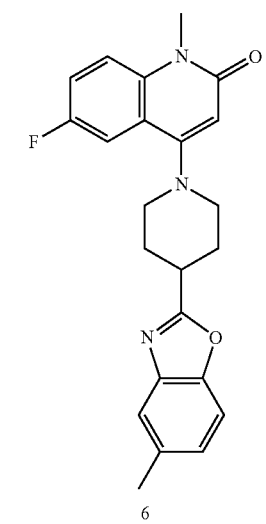

6

To a mixture of compound 5-1 (example 4) (100 mg, 0.245 mmol) and Zn (15.99 mg, 0.245 mmol) in DMF (5 mL) was added zinc bis(acetate) (4.49 mg, 0.024 mmol), Zn(CN)$_2$ (57.43 mg, 0.489 mmol), DPPF (40.82 mg, 0.049 mmol) and Pd$_2$(dba)$_3$ (22.40 mg, 0.024 mmol). The mixture was stirred at 120° C. for 1 h under Microwave in a sealed tube. The reaction mixture was filtered and the filtrate was concentrated under reduced pressure. The residue was purified by preparative HPLC (Flow rate 20 ml/min; mobile phase: 0.1% FA solution, acetonitrile; gradient: 43%-53% acetonitrile Column: C18) to give example 5. MS (ESI) m/z (M+H)$^+$=400.2. $^1$H NMR (400 MHz, CDCl$_3$) δ 8.02 (s, 1H), 7.85 (d, J=8.4 Hz, 1H), 7.52 (s, 1H), 7.40 (d, J=8.4 Hz, 1H), 7.34 (d, J=8.4 Hz, 1H), 7.18 (d, J=8.0 Hz, 1H), 4.42 (d, J=12.4 Hz, 2H), 3.63 (s, 3H), 3.54 (s, 2H), 3.45 (s, 1H), 2.48 (s, 3H), 2.37 (s, 2H), 2.27 (s, 2H).

To a mixture of compound 6-1 (3 g, 16.56 mmol) in DMF (20 mL) was added K₂CO₃ (6.867 g, 49.69 mmol) and MeI (3.53 g, 24.85 mmol). The mixture was stirred at 20° C. for 2 h under N₂. The mixture was quenched with H₂O (50 mL) and precipitate formed. The mixture was filtered. The filter cake was washed with H₂O (20 mL) and dried under reduced pressure to give compound 6-2, which was used for the next step without further purification. ¹H NMR (400 MHz, DMSO) δ 7.85-7.68 (m, 2H), 7.58-7.41 (m, 1H), 3.47 (s, 3H).

To a mixture of compound 6-2 (500 mg, 2.562 mmol) in NMP (10 mL) was added diethyl malonate (451.41 mg, 2.818 mmol) and NaH (122.98 mg, 3.075 mmol, 60% in mineral oil). The mixture was stirred at 120° C. for 2 h under N₂. The mixture was diluted with PE/EtOAc (150 mL/30 mL) and washed with brine (3×150 mL). The organic layer was dried over Na₂SO₄, filtered, and concentrated under reduced pressure to give compound 6-3, which was used for the next step without further purification. MS (ESI) m/z (M–H)⁺=264.0

To a mixture of compound 6-3 (286 mg, 1.078 mmol) in dioxane (4 mL) and H₂O (2 mL) was added NaOH (431.31 mg, 10.783 mmol). The mixture was stirred at 120° C. for 16 h under N₂. The mixture was concentrated under reduced pressure. The residue was adjusted to pH=4-5 with aq. HCl solution (1 M) and precipitate formed. The mixture was filtered. The filter cake was rinsed with H₂O (20 mL) and dried under reduced pressure to give compound 6-4, which was used for the next step without further purification. MS (ESI) m/z (M+H)⁺=194.0

A mixture of compound 6-4 (193 mg, 0.999 mmol) in POCl₃ (4 mL) was stirred at 90° C. for 2 h under N₂. The residue was adjusted to pH=7-8 with aq. NaHCO₃ Solution and extracted with DCM (150 mL). The organic layer was washed with brine (3×150 mL), dried over Na₂SO₄, filtered, and concentrated under reduced pressure to give compound 6-5, which was used for the next step without further purification. MS (ESI) m/z (M+H)⁺=211.9

To a mixture of compound 6-5 (146 mg, 0.69 mmol) in IPA (10 mL) was added compound 1-10 (149.23 mg, 0.69 mmol) and DIEA (445.86 mg, 3.45 mmol). The mixture was stirred at 90° C. for 16 h under N₂. The mixture was concentrated under reduced pressure to give crude product. The crude product was purified by prep-HPLC to give example 6. MS (ESI) m/z (M+H)⁺=392.3. ¹H NMR (400 MHz, DMSO) δ 7.67-7.39 (m, 5H), 7.19 (d, J=8.3 Hz, 1H), 6.13 (s, 1H), 3.57 (s, 3H), 3.48-3.38 (m, 2H), 3.29-3.23 (m, 1H), 3.00-2.87 (m, 2H), 2.43 (s, 3H), 2.34-2.05 (m, 4H).

Example 7: 6-fluoro-1-methyl-4-(4-(5-methylbenzo[d]oxazol-2-yl)piperidin-1-yl)quinazolin-2(1H)-one

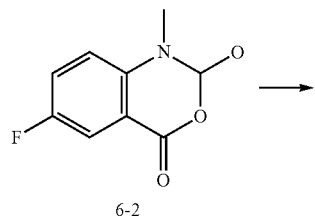

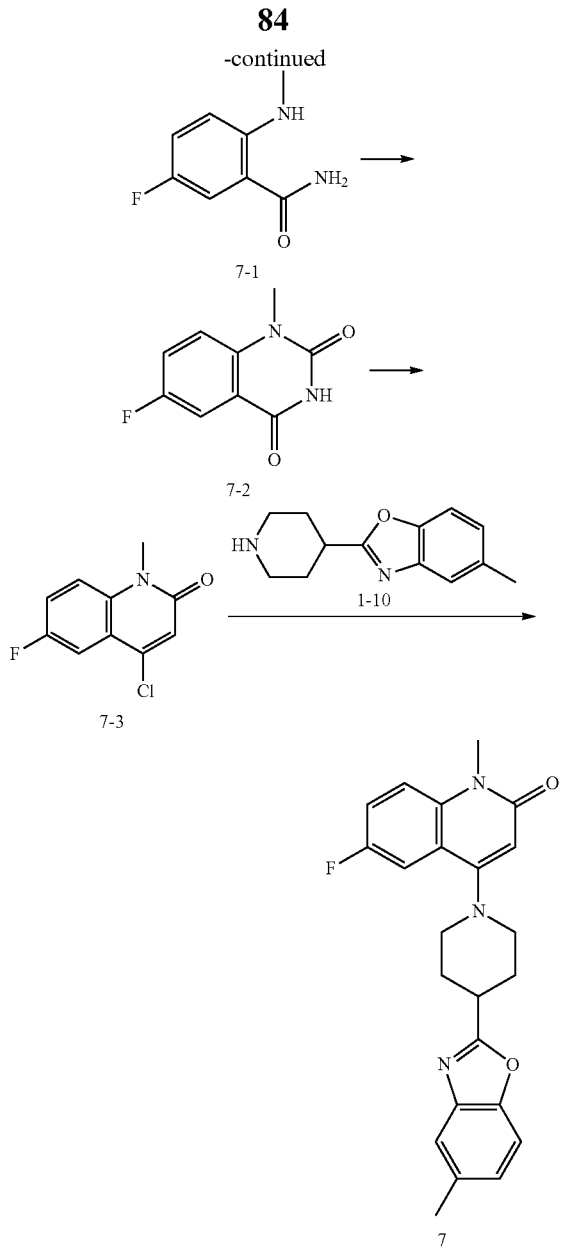

To a mixture of compound 6-2 (600 mg, 3.08 mmol) in THF (7 mL) was added ammonium hydroxide (3.5 mL, 25.44 mmol). The mixture was stirred at 15° C. for 30 min. The mixture was concentrated under reduced pressure. A solution of HCl (4 M) in MeOH was added to the residue and the mixture was stirred at 15° C. for 16 h. The mixture was concentrated under reduced pressure. The residue was adjusted to pH=8-9 with aq. NaHCO₃ solution and extracted with DCM (50 mL). The organic layer was washed with brine (3×50 mL), dried over Na₂SO₄, filtered, and concentrated under reduced pressure to give compound 7-1, which was used for the next step without further purification. MS (ESI) m/z (M+H)⁺=169.0

To a mixture of compound 7-1 (440 mg, 2.62 mmol) in THF (5 mL) was added NaH (313.92 mg, 13.08 mmol, 60% in mineral oil) and CDI (636.28 mg, 3.92 mmol). The mixture was stirred at 15° C. for 3 h under N₂. The mixture was quenched with sat. NH₄Cl solution (30 mL) and the precipitate formed. The mixture was filtered. The filter cake was rinsed with DCM (30 mL) and dried under reduced pressure to give compound 7-2. MS (ESI) m/z (M+H)⁺ =195.0.

To a mixture of compound 7-2 (356 mg, 1.83 mmol) in toluene (5 mL) was added DIEA (1.52 mL, 9.17 mmol) and POCl₃ (0.85 mL, 9.17 mmol). The mixture was stirred at 110° C. for 3 h under N₂. The residue was adjusted to pH=7-8 with aq. NaHCO₃ solution and extracted with DCM (30 mL). The organic layer was washed with brine (3×30 mL), dried over Na₂SO₄, filtered, and concentrated under reduced pressure to give compound 7-3, which was used for the next step without further purification. MS (ESI) m/z (M+H)⁺=212.9.

To a mixture of compound 7-3 (200 mg, 0.94 mmol) in IPA (5 mL) was added compound 1-10 (122.07 mg, 0.56 mmol) and DIEA (607.92 mg, 4.70 mmol). The mixture was stirred at 90° C. for 16 h under N₂. The mixture was concentrated under reduced pressure. The crude product was purified by prep-HPLC to give example 7. MS (ESI) m/z (M+H)⁺=393.0. ¹H NMR (400 MHz, DMSO) δ 7.71-7.53 (m, 3H), 7.52-7.45 (m, 2H), 7.18 (d, J=8.0 Hz, 1H), 4.27-4.14 (m, 2H), 3.47 (s, 3H), 3.43-3.35 (m, 3H), 2.41 (s, 3H), 2.25-2.16 (m, 2H), 2.07-1.95 (m, 2H).

Example 8: 6-fluoro-1-methyl-4-((1R,5S)-8-(5-methylbenzo[d]oxazol-2-yl)-3,8-diazabicyclo[3.2.1]octan-3-yl)-2-oxo-1,2-dihydroquinoline-3-carbonitrile

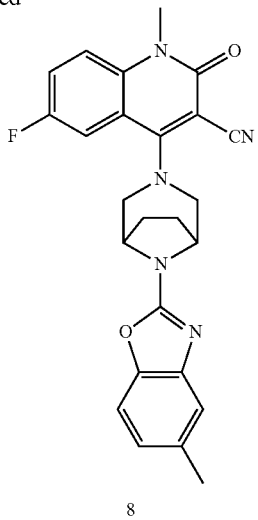

8

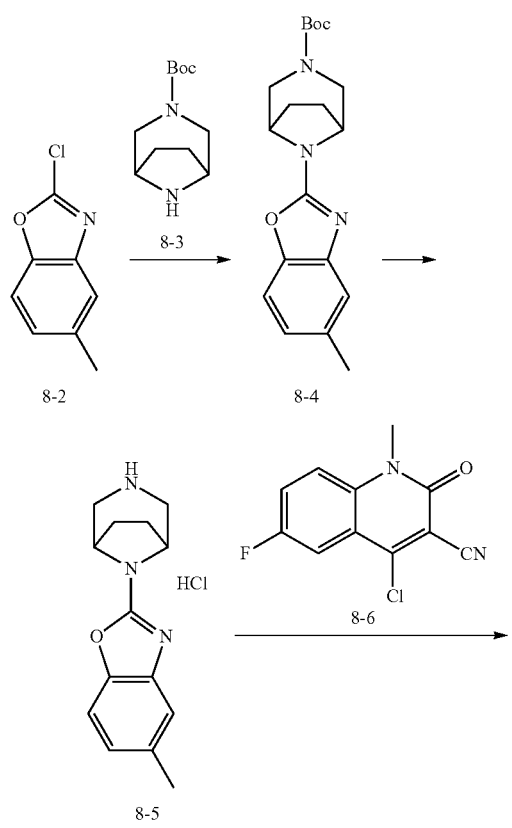

To a mixture of compound 8-2 (500 mg, 2.596 mmol) in DMSO (30 mL) was added DIEA (2.145 mL, 12.97 mmol) and compound 8-3 (551.02 mg, 2.596 mmol). The reaction mixture was stirred at 100° C. for 2 h. The mixture was poured into ice-water (100 mL) and extracted with DCM (3×50 mL). The combined organic layers were dried over Na₂SO₄, filtered, and concentrated under reduced pressure to give the crude, which was purified by flash column chromatography eluting with petroleum ether/Ethyl acetate=1/1 to give compound 8-4. MS (ESI) m/z (M+H)⁺=344.2.

A mixture of compound 8-4 (900 mg, 2.530 mmol) in HCl/dioxane (50 mL, 4 M) was stirred at 25° C. for 2 h. The mixture was concentrated under reduced pressure to give compound 8-5, which was used for the next step without further purification. MS (ESI) m/z (M+H)⁺=244.1.

To a mixture of compound 8-6 (150 mg, 0.628 mmol) in DMSO (20 mL) was added DIEA (1.037 mL, 6.276 mmol) and compound 8-5 (240.15 mg, 0.816 mmol). The reaction mixture was stirred at 130° C. for 2 h. The mixture was poured into ice-water (100 mL) and extracted with DCM (3×50 mL). The combined organic layers were dried over Na₂SO₄, filtered, and concentrated under reduced pressure to give the crude, which was purified by Prep-HPLC to give example 8. MS (ESI) m/z (M+H)⁺=444.4. ¹H NMR (400 MHz, MeOD) δ 7.88 (dd, J=9.6, 2.9 Hz, 1H), 7.69 (dd, J=9.4, 4.6 Hz, 1H), 7.63-7.56 (m, 1H), 7.28 (d, J=8.3 Hz, 1H), 7.19 (s, 1H), 6.98 (d, J=7.2 Hz, 1H), 4.75-4.70 (m, 2H), 3.97 (d, J=11.1 Hz, 2H), 3.71 (s, 3H), 3.53 (d, J=10.0 Hz, 2H), 2.46-2.39 (m, 5H), 2.37-2.25 (m, 2H).

Example 9: 6-chloro-1-methyl-4-(4-(5-methylbenzo[d]oxazol-2-yl)piperidin-1-yl)-2-oxo-1,2-dihydro-1,5-naphthyridine-3-carbonitrile

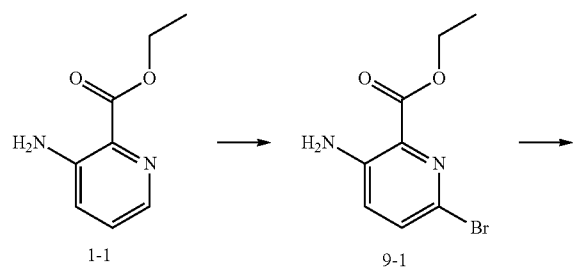

1-1    9-1

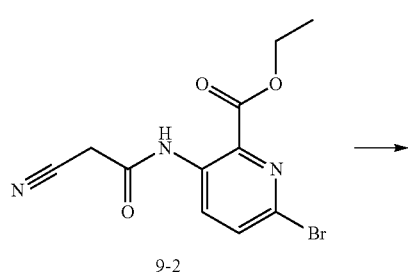

9-2

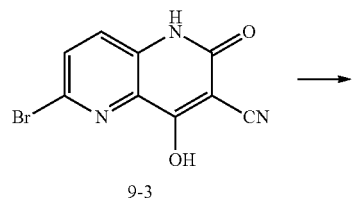

9-3

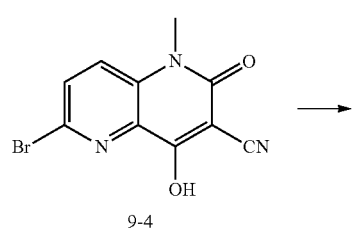

9-4

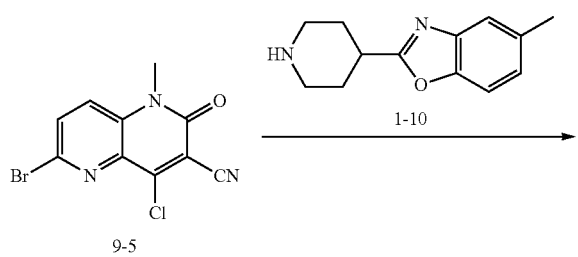

9-5

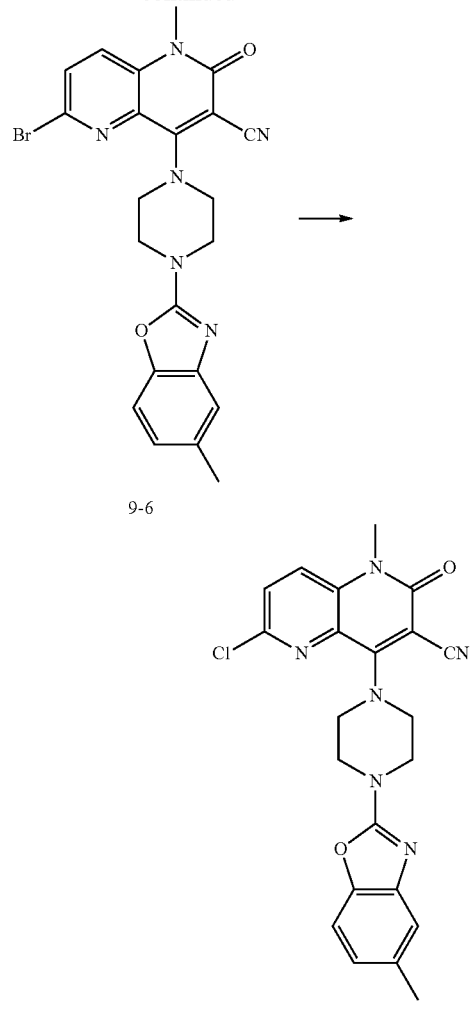

9-6

9

A mixture of compound 1-1 (10 g, 60.18 mmol) and NBS (10.82 g, 60.78 mmol) in ACN (120 mL) was stirred at 20° C. for 1.5 hours. The reaction mixture was diluted with water (100 mL) and extracted with ethyl acetate (3×100 mL). The combined organic layers were dried over $Na_2SO_4$, filtered, and concentrated under reduced pressure to give compound 9-1. MS (ESI) m/z (M+H)$^+$=245.

To a mixture of compound 9-1 (12.065 g, 49.23 mmol) in DMF (100 mL) was added 2-cyanoacetic acid (5.86 g, 68.92 mmol), DIEA (24.476 mL, 148.10 mmol) and $T_3P$ (50% in EA, 62.9 g, 197.69 mmol). The reaction mixture was stirred at 25° C. for 16 h. The reaction mixture was diluted with EtOAc (300 mL) and washed with brine (3×300 mL). The organic layer was dried over $Na_2SO_4$, filtered, and concentrated under reduced pressure to give compound 9-2. MS (ESI) m/z (M+H)$^+$=313.

To a mixture of compound 9-2 (3.8 g, 12.17 mmol) in THF (100 mL) was added KHMDS (14.2 mL, 14.19 mmol, 1 M) at −78° C. under $N_2$. The reaction mixture was allowed to warm to 20° C. and stirred at 20° C. for 1.5 h under $N_2$. The mixture was quenched with sat. $Na_2SO_4$ solution (14 mL). The mixture was filtered and the filtrate was concentrated under reduced pressure to give compound 9-3. $^1$H NMR (400 MHz, DMSO) δ 11.95 (s, 1H), 7.85 (d, J=8.7 Hz, 1H), 7.63 (d, J=8.7 Hz, 1H).

To a mixture of compound 9-3 (1000 mg, 3.76 mmol) in DMF (20 mL) was added NaH (601.39 mg, 15.03 mmol, 60% in mineral oil) at 0° C., then the mixture was stirred at 0° C. for 0.5 h under $N_2$. $CH_3I$ (0.936 mL, 15.03 mmol) was added to the mixture. Then the reaction mixture was stirred at room temperature for 12 h under $N_2$. The mixture was diluted with $H_2O$ (15 mL), adjusted to pH=3 with 1 M HCl solution, and precipitate formed. The mixture was filtered and the filter cake was rinsed with $H_2O$ (20 mL). The filter cake was collected and dried under reduced pressure to give compound 9-4, which was used for the next step without further purification. MS (ESI) m/z (M+H)$^+$=279.9.

To a mixture of compound 9-4 (500 mg, 1.79 mmol) in $POCl_3$ (10 mL) was added DIEA (1.770 mL, 10.71 mmol). The reaction mixture was stirred at 120° C. under $N_2$ for 4 h. The mixture was concentrated under reduced pressure. The residue was purified by column chromatography on silica gel to afford compound 9-4. MS (ESI) m/z (M+H)$^+$=299.9. $^1$H NMR (400 MHz, DMSO) δ 8.22 (dd, J=47.4, 9.0 Hz, 1H), 8.04 (dd, J=37.2, 9.0 Hz, 1H), 3.65 (d, J=4.6 Hz, 3H).

To a mixture of compound 9-5 (100 mg, 0.335 mmol) and compound 1-10 (21.54 mg, 0.087 mmol) in IPA (5 mL) was added DIEA (0.332 mL, 2.010 mmol). The reaction mixture was stirred at 90° C. for 2 h. The mixture was quenched with $H_2O$ and extracted with EtOAc. The organic layer was dried over $Na_2SO_4$, filtered, and concentrated under reduced pressure to give compound 9-6. MS (ESI) m/z (M+H)$^+$=478.2.

A mixture of compound 9-6 (50 mg, 0.108 mmol) in HCl/dioxane (5 mL, 4 M) was stirred at 85° C. for 12 h. The mixture was concentrated under reduced pressure. The residue was purified by preparative HPLC to give example 9. MS (ESI) m/z (M+H)$^+$=434.1. $^1$H NMR: (400 MHz, MeOD) δ 8.54 (s, 1H), 8.03 (d, J=9.0 Hz, 1H), 7.70 (d, J=9.0 Hz, 1H), 7.50-7.45 (m, 2H), 7.21 (d, J=8.3 Hz, 1H), 4.45 (d, J=13.0 Hz, 2H), 3.73 (t, J=10.5 Hz, 2H), 3.65 (s, 3H), 3.47-3.43 (m, 1H), 2.46 (s, 3H), 2.42-2.26 (m, 4H).

Example 10: 6-chloro-1-methyl-4-(4-(5-methyl-benzo[d]oxazol-2-yl)piperidin-1-yl)-1,5-naphthyridin-2(1H)-one

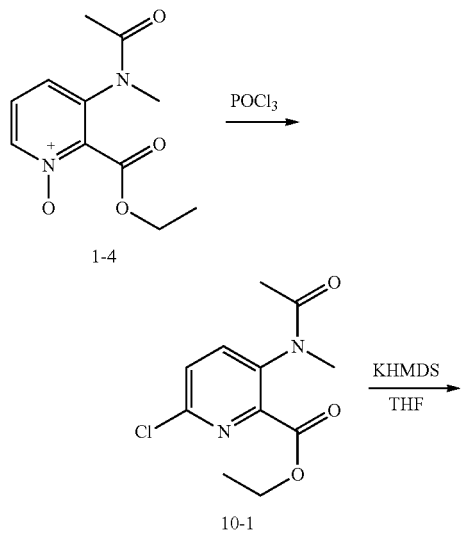

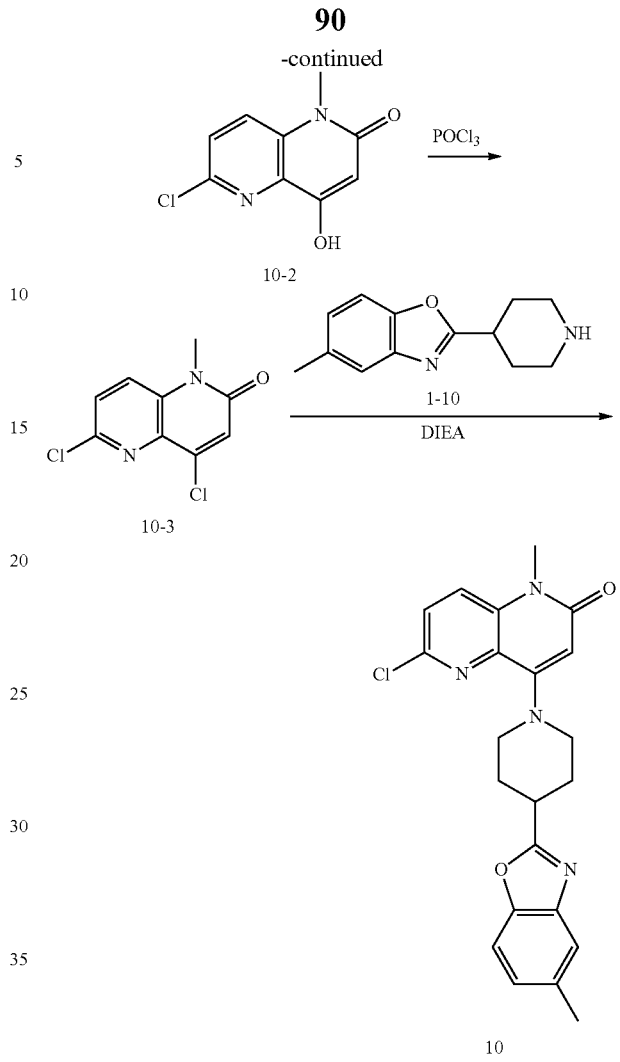

A mixture of 1-4 (2.0 g, 8.40 mmol) in $POCl_3$ (15 mL) was stirred at 65° C. for 2 h. The mixture was concentrated under reduced pressure. The residue was diluted with DCM (50 mL) and adjusted to pH=8.0 with Sat. $NaHCO_3$ solution. The mixture was extracted with DCM (3×50 mL). The combined organic layers were dried over $Na_2SO_4$, filtered, and concentrated under reduced pressure. The resulting residue was purified by flash column chromatography to give 10-1. LCMS: MS m/z (ESI) [M+H]$^+$=257.2.

To a solution of KHMDS (1M in THF) (6.68 mL, 6.68 mmol) in THF (100 mL) at −78° C. was added a solution of 10-1 (1.4 g, 4.45 mmol) in THF (10 mL) dropwise under $N_2$. After addition, the mixture was slowly warmed up to 15° C. and stirred at the temperature for 2 h. The mixture was adjusted to pH=6.0 with 1 N HCl. The mixture was concentrated in vacuo. The resulting residue was purified by flash column chromatography to give 10-2. LCMS: MS m/z (ESI) [M+H]$^+$=211.2.

A mixture of 10-2 (680 mg, 2.50 mmol) in $POCl_3$ (20 mL) was stirred at 100° C. for 2 h. The mixture was concentrated under reduced pressure. The resulting residue was diluted with DCM (50 mL) and adjusted to pH=8.0 with Sat. $NaHCO_3$ solution. The mixture was extracted with DCM (3×50 mL). The combined organic layers were dried over $Na_2SO_4$, filtered, and concentrated under reduced pressure. The resulting residue was purified by flash column chromatography to give 10-3. LCMS: MS m/z (ESI) [M+H]$^+$=229.1.

A mixture of 10-3 (40 mg, 0.18 mmol), 1-10 (41.6 mg, 0.19 mmol) and DIEA (0.14 mL, 0.87 mmol) in isopropyl alcohol (3 mL) was stirred at 90° C. for 18 h. The mixture was concentrated in vacuo and the resulting residue was purified by prep-HPLC separation to give example 10. LCMS: MS m/z (ESI) [M+H]$^+$=409.1. $^1$H NMR (400 MHz, DMSO-d$_6$) δ 8.01 (d, J=9.0 Hz, 1H), 7.69 (d, J=8.9 Hz, 1H), 7.56 (d, J=8.2 Hz, 1H), 7.51 (s, 1H), 7.18 (d, J=8.0 Hz, 1H), 6.10 (s, 1H), 4.06 (d, J=12.3 Hz, 2H), 3.53 (s, 3H), 3.44-3.07 (m, 3H), 2.42 (s, 3H), 2.27-2.18 (m, 2H), 2.08-1.98 (m, 2H).

Example 11: 6-chloro-4-(4-(5-fluorobenzo[d]oxazol-2-yl)piperidin-1-yl)-1-methyl-1,5-naphthyridin-2(1H)-one

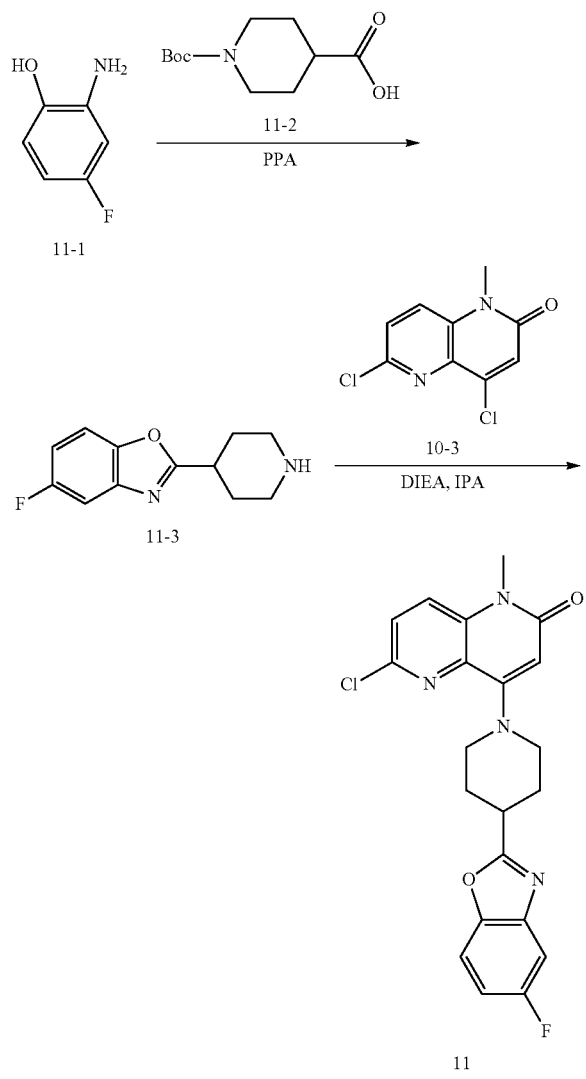

To a mixture of 11-2 (9.0 g, 39.25 mmol) in polyphosphoric acid (100 mL) was added 11-1 (4.99 g, 39.25 mmol). The mixture was stirred at 200° C. for 4 h. The mixture was cooled to room temperature and quenched with ice water (200 mL). The mixture was basified with aqueous NaOH solution (50% w/w) and the precipitate formed. Collected the precipitate by filtration and the filter cake was rinsed with water, dried under reduced pressure to give 11-3. LCMS: MS m/z (ESI) [M+H]$^+$=221.0.

A mixture of 10-3 (50 mg, 0.22 mmol), 11-3 (57.7 mg, 0.26 mmol) and DIEA (0.18 mL, 1.09 mmol) in isopropyl alcohol (3 mL) was stirred at 90° C. for 36 h. The mixture was concentrated in vacuo and the resulting residue was purified by prep-HPLC separation to give example 11. LCMS: MS m/z (ESI) [M+H]$^+$=413.1. $^1$H NMR (400 MHz, DMSO-d$_6$) δ 8.01 (d, J=8.9 Hz, 1H), 7.78-7.68 (m, 2H), 7.63-7.57 (m, 1H), 7.27-7.20 (m, 1H), 6.11 (s, 1H), 4.06 (d, J=12.3 Hz, 2H), 3.53 (s, 3H), 3.36-3.28 (m, 1H), 3.12 (t, J=11.6 Hz, 2H), 2.26-2.20 (m, 2H), 2.09-2.00 (m, 2H).

Example 12: 8-(4-(5-fluorobenzo[d]oxazol-2-yl)piperidin-1-yl)-5-methyl-6-oxo-5,6-dihydro-1,5-naphthyridine-2-carbonitrile

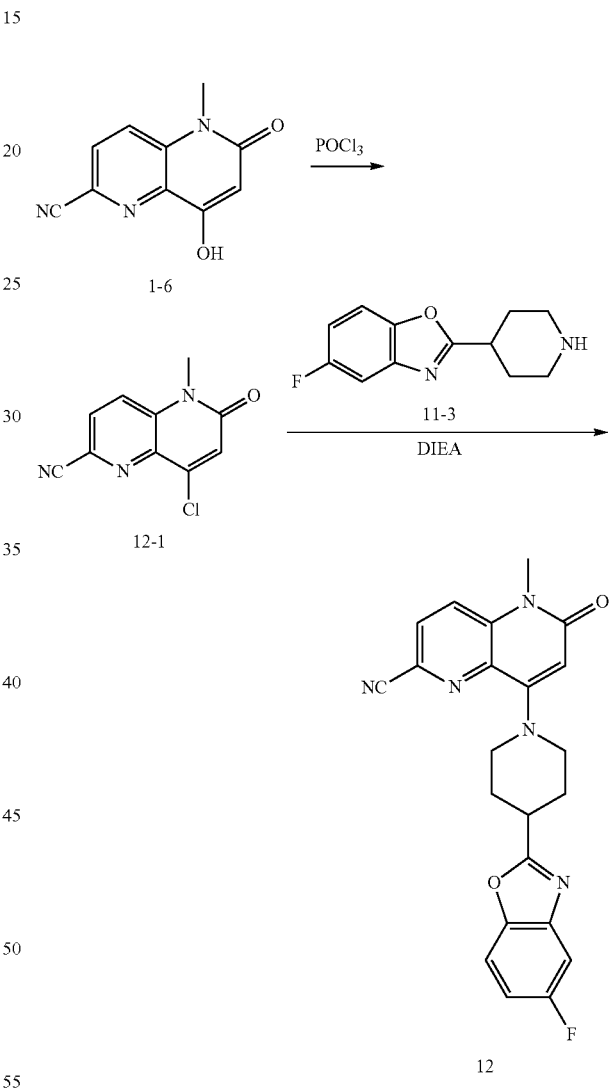

A mixture of 1-6 (900 mg, 4.47 mmol) in POCl$_3$ (10 mL) was stirred at 85° C. for 2 h. The reaction mixture was concentrated under reduced pressure. The residue was quenched with saturated NaHCO$_3$ solution (50 mL) and extracted with DCM (3×100 mL). The combined organic layers were dried over Na$_2$SO$_4$, filtered, and concentrated under reduced pressure to give 12-1. LCMS: MS m/z (ESI) [M+H]$^+$=220.1

To a mixture of 12-1 (100 mg, 0.45 mmol) in DMSO (10 mL) was added 11-3 (239 mg, 0.90 mmol) and DIEA (0.75 mL, 4.51 mmol). The reaction mixture was stirred at 130° C.

for 16 h. The mixture was cooled to room temperature and poured into water (100 mL). The resulting mixture was extracted with DCM (3×50 mL). The combined organic layers dried over Na$_2$SO$_4$, filtered, and concentrated under reduced pressure. To the resulting residue was added MeOH (5 mL) and THF (5 mL). After stirring for 16 h, the mixture was filtered. The filter cake was collected and dried to give example 12. LCMS: MS m/z (ESI) [M+H]$^+$=404.1. $^1$H NMR (400 MHz, DMSO) δ 8.18 (d, J=8.8 Hz, 1H), 8.09 (d, J=8.8 Hz, 1H), 7.74 (dd, J=8.9, 4.4 Hz, 1H), 7.60 (dd, J=8.8, 2.6 Hz, 1H), 7.24 (td, J=9.6, 2.6 Hz, 1H), 6.17 (s, 1H), 4.06 (d, J=12.8 Hz, 2H), 3.55 (s, 3H), 3.43-3.33 (m, 1H), 3.21-3.11 (m, 2H), 2.29-2.20 (m, 2H), 2.11-1.99 (m, 2H).

Example 13: 6-chloro-1-methyl-4-(4-(5-methyl-benzo[d]oxazol-2-yl)piperidin-1-yl)pyrido[3,2-d]pyrimidin-2(1H)-one

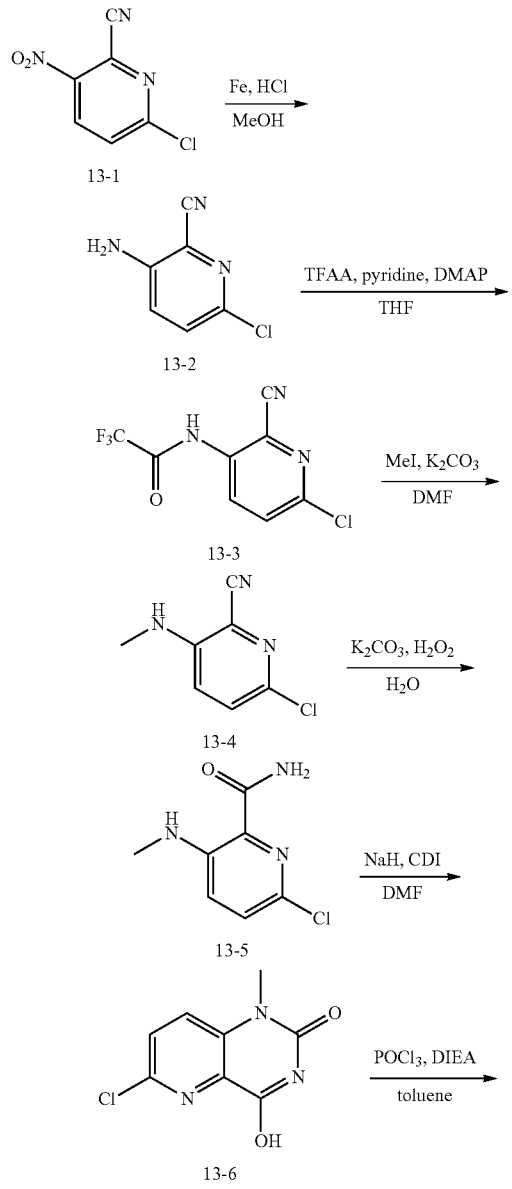

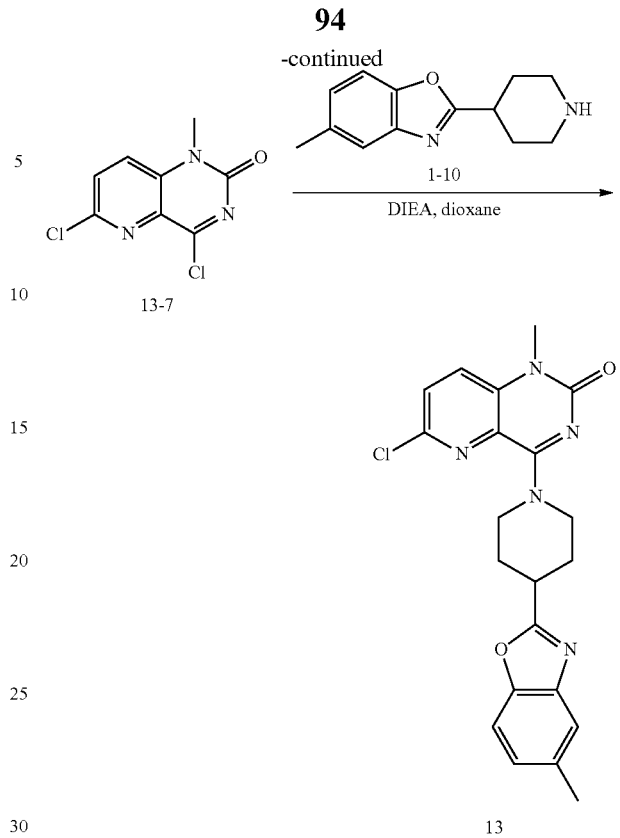

To a mixture of 13-1 (5.0 g, 27.2 mmol) in MeOH (60 mL) and HCl (25 mL, 37% w/w) was added Fe (1.07 g, 19.1 mmol) at 20° C. After stirring at 80° C. for 1 h, the reaction mixture was cooled to room temperature and poured into ice-water (100 mL). The mixture was filtered and the filter cake was washed with DCM (100 mL). The filtrate was extracted with DCM (100 mL×2). The combine organic layers were washed with brine (300 mL), dried over Na$_2$SO$_4$, filtered, and concentrated under reduced pressure to give 13-2, which was directly used in the next step without further purification.

To a suspension of 13-2 (3.3 g, 21.5 mmol) in THF (50 mL) were added DMAP (1.31 g, 10.75 mmol), pyridine (6.84 mL, 86 mmol) and TFAA (5.50 mL, 43 mmol). The mixture was stirred at 25° C. for 2 h. The reaction mixture was filtered and the filtrate was evaporated in reduced pressure. The resulting residue was dissolved in DCM (80 mL) and the mixture was washed with water (80 mL). The organic layer was dried over Na$_2$SO$_4$, filtered, and concentrated under reduced pressure to afford 13-3, which was directly used for the next step without further purification.

To a solution of 13-3 (2.5 g, 10.0 mmol) in DMF (15 mL) was added MeI (2.63 g, 18.5 mmol) and K$_2$CO$_3$ (4.15 g, 30.1 mmol). After stirring at 20° C. for 16 h, the reaction mixture was quenched with water (50 mL) and extracted with ethyl acetate (50 mL×3). The combined organic layers were dried over Na$_2$SO$_4$, filtered, and concentrated under reduced pressure to afford 13-4. LCMS: MS m/z (ESI) [M+H]$^+$=168.2.

To a solution of 13-4 (1.4 g, 8.35 mmol) in DMSO (20 mL) and H$_2$O (5.0 mL) was added K$_2$CO$_3$ (2.31 g, 16.71 mmol) and H$_2$O$_2$ (1.89 g, 16.71 mmol). After stirring at 20° C. for 16 h, the reaction mixture was diluted with water (40 mL) and the precipitate formed. The mixture was filtered and the filter cake was dried under reduced pressure to give 13-5.

To a solution of 13-5 (580 mg, 3.13 mmol) in DMF (5 mL) was added NaH (375 mg, 9.37 mmol, 60% in mineral oil) at 0° C. under $N_2$. After stirring at room temperature for 1 h, a solution of CDI (760.04 mg, 4.687 mmol) in DMF (3 mL) was added to the above solution. The reaction mixture was allowed to warm to 70° C. and stirred for another 2 h. After cooling to room temperature, the precipitate formed and the mixture was filtered. The filter cake was washed with water and dried under reduced pressure to afford 13-6, which was checked by LCMS: MS m/z (ESI) $[M+H]^+$=212.0.

To a suspension of 13-6 (200 mg, 0.95 mmol) in dry toluene (8 mL) were added $POCl_3$ (0.44 mL, 4.73 mmol) and DIEA (0.78 mL, 4.73 mmol) at room temperature. The reaction mixture was heated at 110° C. for 2 h under $N_2$. The reaction mixture was concentrated under reduced pressure to give 13-7, which was directly used for next step without further purification.

To a mixture of 13-7 (100 mg, 0.44 mmol) in $CH_3CN$ (5 mL) was added 1-10 (188 mg, 0.87 mmol) and DIEA (0.72 mL, 4.35 mmol). The mixture was stirred at 90° C. for 2 h. The mixture was concentrated under reduced pressure. The resulting residue was purified by prep-HPLC separation to give example 13. LCMS: MS m/z (ESI) $[M+H]^+$=410.1. $^1$H NMR (400 MHz, DMSO) δ 7.95 (d, J=9.0 Hz, 1H), 7.82 (d, J=9.0 Hz, 1H), 7.54 (d, J=8.3 Hz, 1H), 7.49 (s, 1H), 7.17 (d, J=8.3 Hz, 1H), 3.70-3.25 (m, 8H), 2.41 (s, 3H), 2.28-2.18 (m, 2H), 2.02-1.89 (m, 2H).

Example 14: 1-methyl-4-(4-(5-methylbenzo[d]oxazol-2-yl)piperidin-1-yl)-2-oxo-1,2-dihydropyrido[3,2-d]pyrimidine-6-carbonitrile

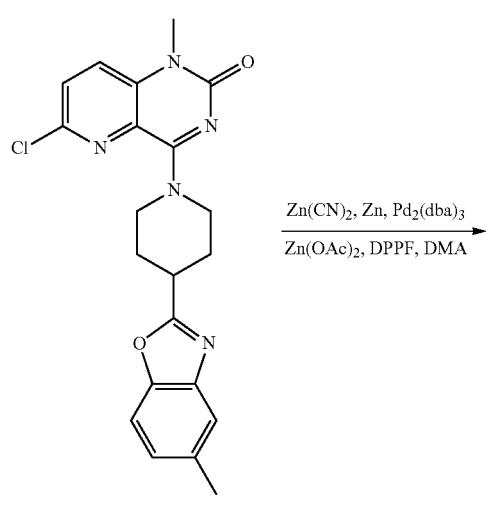

13

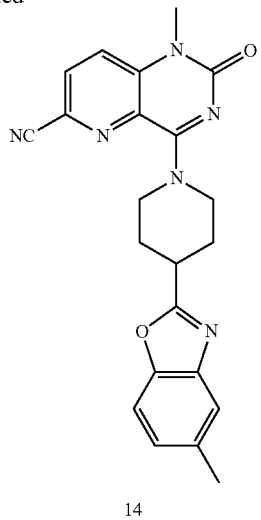

14

To a mixture of compound 13 (50 mg, 0.12 mmol) in DMA (2 mL) was added Zn (8.0 mg, 0.12 mmol), $Zn(OAc)_2$ (2.7 mg, 0.012 mmol), $Zn(CN)_2$ (28.7 mg, 0.24 mmol), DPPF (13.8 mg, 0.024 mmol) and $Pd_2(dba)_3$-$CHCl_3$ (11.2 mg, 0.012 mmol). The mixture was stirred at 150° C. for 1 h under microwave. The mixture was filtered through a celite pad and the filtrate was purified by prep-HPLC separation to give example 14. LCMS: MS m/z (ESI) $[M+H]^+$=401.1. $^1$H NMR (400 MHz, DMSO) δ 8.25 (d, J=8.9 Hz, 1H), 8.00 (d, J=8.9 Hz, 1H), 7.54 (d, J=8.3 Hz, 1H), 7.48 (s, 1H), 7.17 (d, J=8.3 Hz, 1H), 3.75-3.25 (m, 8H), 2.41 (s, 3H), 2.31-2.20 (m, 2H), 2.04-1.90 (m, 2H).

Example 15: 6-chloro-7-(2-methoxyethoxy)-1-methyl-4-(4-(5-methylbenzo[d]oxazol-2-yl)piperidin-1-yl)-1,5-naphthyridin-2(1H)-one

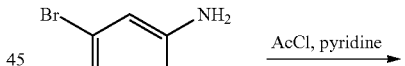

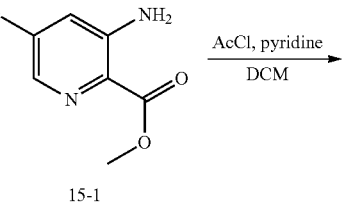

15-1

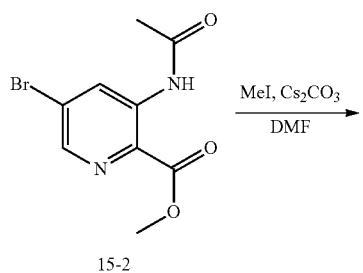

15-2

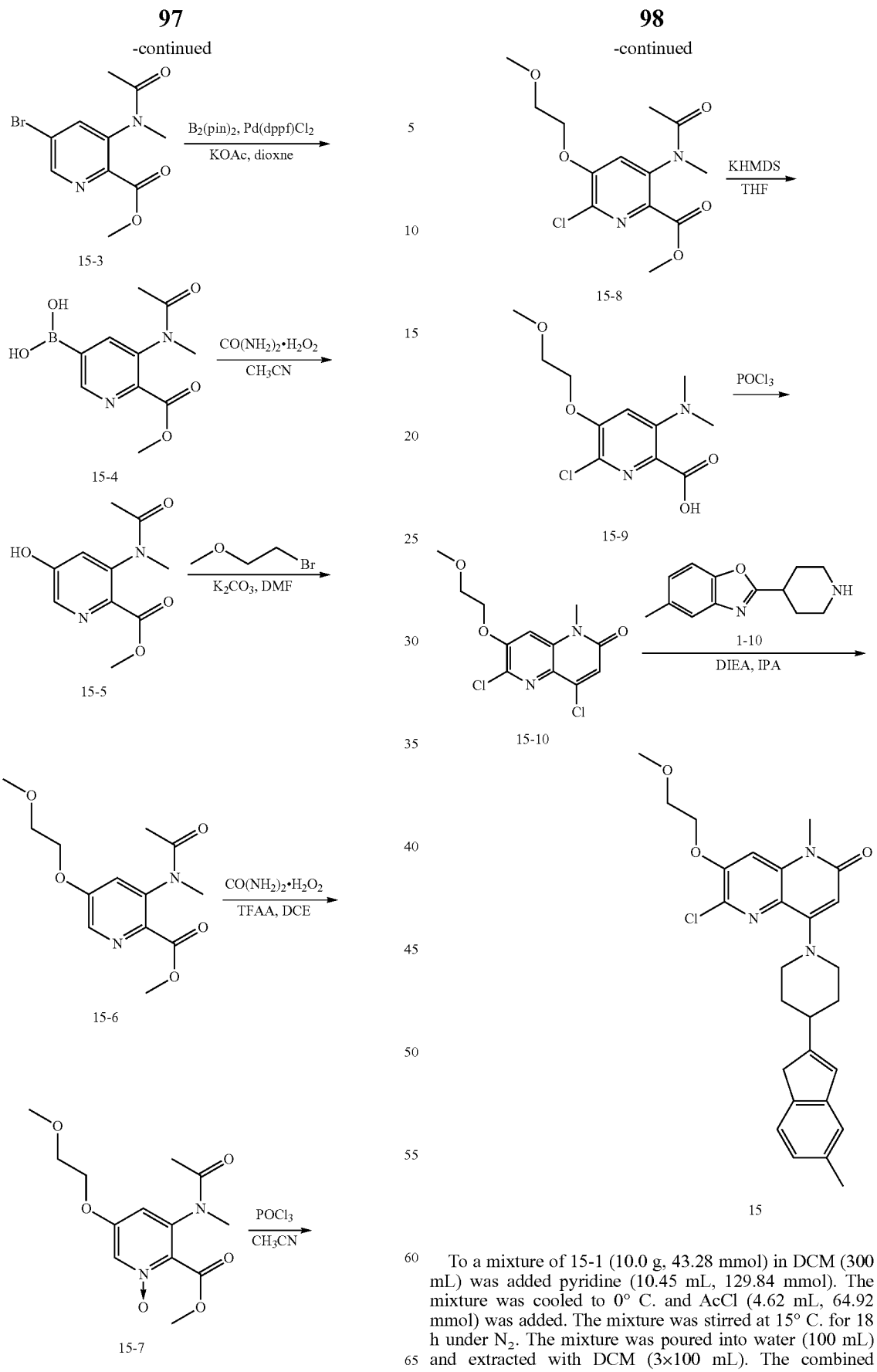
To a mixture of 15-1 (10.0 g, 43.28 mmol) in DCM (300 mL) was added pyridine (10.45 mL, 129.84 mmol). The mixture was cooled to 0° C. and AcCl (4.62 mL, 64.92 mmol) was added. The mixture was stirred at 15° C. for 18 h under $N_2$. The mixture was poured into water (100 mL) and extracted with DCM (3×100 mL). The combined organic layers were dried over $Na_2SO_4$, filtered, and concentrated under reduced pressure. The resulting residue was purified by flash column chromatography to give 15-2. LCMS: MS m/z (ESI) [M+H]+=272.9.

To a mixture of 15-2 (11.0 g, 40.26 mmol) in DMF (150 mL) was added $Cs_2CO_3$ (26.23 g, 80.52 mmol) and MeI (8.57 g, 60.39 mmol). The mixture was stirred at 25° C. for 18 h under $N_2$. The mixture was poured into water (100 mL) and extracted with DCM (3×100 mL). The combined organic layers were dried over $Na_2SO_4$, filtered, and concentrated under reduced pressure. The resulting residue was purified by flash column chromatography to give 15-3. LCMS: MS m/z (ESI) [M+H]+=287.1.

To a mixture of 15-3 (3.2 g, 10.59 mmol) in dioxane (150 mL) was added $B_2(pin)_2$ (4.03 g, 15.88 mmol), $Pd(dppf)Cl_2$ (1.55 g, 2.12 mmol), KOAc (3.12 g, 31.77 mmol). The mixture was stirred at 100° C. for 3 h under $N_2$. The mixture was poured into water (100 mL) and extracted with DCM (3×50 mL). The combined organic layers were dried over $Na_2SO_4$, filtered, and concentrated under reduced pressure to give 15-4. LCMS: MS m/z (ESI) [M+H]+=252.5.

To a mixture of 15-4 (3.0 g, 11.31 mmol) in $CH_3CN$ (300 mL) was added $CO(NH_2)_2 \cdot H_2O_2$ (2.13 g, 22.62 mmol). The mixture was stirred at 25° C. for 18 h under $N_2$. The mixture was concentrated under reduced pressure. The resulting residue was purified by flash column chromatography to give 15-5. LCMS: MS m/z (ESI) [M+H]+=225.0.

To a solution of 15-5 (830 mg, 3.30 mmol) in DMF (20 mL) was added 1-bromo-2-methoxyethane (1.37 g, 9.89 mmol) and $K_2CO_3$ (2.73 g, 19.78 mmol). The mixture was stirred at 60° C. for 18 h under $N_2$. The mixture was poured into water (30 mL) and extracted with DCM (3×30 mL). The combined organic layers dried over $Na_2SO_4$, filtered, and concentrated under reduced pressure. The resulting residue was purified by flash column chromatography to give 15-6. LCMS: MS m/z (ESI) [M+H]+=283.0.

To a solution of 15-6 (500 mg, 1.77 mmol) in DCE (50 mL) was added $CO(NH_2)_2 \cdot H_2O_2$ (1.58 g, 16.83 mmol) and TFAA (3.53 g, 16.8 mmol). The mixture was stirred at 70° C. for 2 h under $N_2$. The mixture was adjusted to pH=8.0 with sat. $NaHCO_3$ solution. The resulting mixture was extracted with DCM (3×50 mL). The combined organic layers were dried over $Na_2SO_4$, filtered, and concentrated under reduced pressure to give 15-7. LCMS: MS m/z (ESI) [M+H]+=299.0.

To a solution of 15-7 (370 mg, 1.18 mmol) in $CH_3CN$ (50 mL) was added $POCl_3$ (1.10 mL, 11.79 mmol). The mixture was stirred at 70° C. for 2 h under $N_2$. The mixture was concentrated under reduced pressure. The residue was adjusted to pH=8.0 with sat. $NaHCO_3$ solution, the resulting mixture was extracted with DCM (3×50 mL). The combined organic layers were dried over $Na_2SO_4$, filtered, and concentrated under reduced pressure. The resulting residue was purified by flash column chromatography to give 15-8. LCMS: MS m/z (ESI) [M+H]+=316.9.

To a solution of 15-8 (300 mg, 0.88 mmol) in THF (50 mL) was added KHMDS (1.32 mL) at −78° C. under $N_2$. The mixture was stirred at −78° C. for 1 h under $N_2$. The mixture was stirred at 25° C. for 3 h under $N_2$. The mixture was adjusted to pH=5.0 and the resulting mixture was concentrated under reduced pressure. The resulting residue was purified by flash column chromatography to give 15-9. LCMS: MS m/z (ESI) [M+H]+=284.9.

A mixture of 15-9 (180 mg, 0.60 mmol) in $POCl_3$ (5 mL) was stirred at 80° C. for 2 h under $N_2$. The mixture was concentrated under reduced pressure. The residue was adjusted to pH=8.0 with sat. $NaHCO_3$ solution. The resulting mixture was extracted with DCM (3×50 mL). The combined organic layers were dried over $Na_2SO_4$, filtered, and concentrated under reduced pressure to give 15-10. LCMS: MS m/z (ESI) [M+H]+=302.9.

To a solution of 15-10 (170 mg, 0.54 mmol) in isopropyl alcohol (3 mL) was added 1-10 (129 mg, 0.60 mmol) and DIEA (0.90 mL, 5.44 mmol). The mixture was stirred at 100° C. for 30 h under $N_2$. The mixture was poured into water (100 mL) and extracted with DCM (3×50 mL). The combined organic layers were dried over $Na_2SO_4$, filtered, and concentrated under reduced pressure. The resulting residue was purified by preparative HPLC separation to give example 15. LCMS: MS m/z (ESI) [M+H]+=483.1. $^1H$ NMR (400 MHz, DMSO) δ 7.56 (d, J=8.3 Hz, 1H), 7.49 (d, J=10.1 Hz, 2H), 7.18 (d, J=7.9 Hz, 1H), 5.95 (s, 1H), 4.47-4.40 (m, 2H), 4.10-4.01 (m, 2H), 3.80-3.74 (m, 2H), 3.56 (s, 3H), 3.36 (s, 3H), 3.10 (t, 2H), 2.49-2.45 (m, 1H), 2.42 (s, 3H), 2.25-2.16 (m, 2H), 2.09-1.95 (m, 2H).

Example 16: 3-(2-methoxyethoxy)-5-methyl-8-(4-(5-methylbenzo[d]oxazol-2-yl)piperidin-1-yl)-6-oxo-5,6-dihydro-1,5-naphthyridine-2-carbonitrile

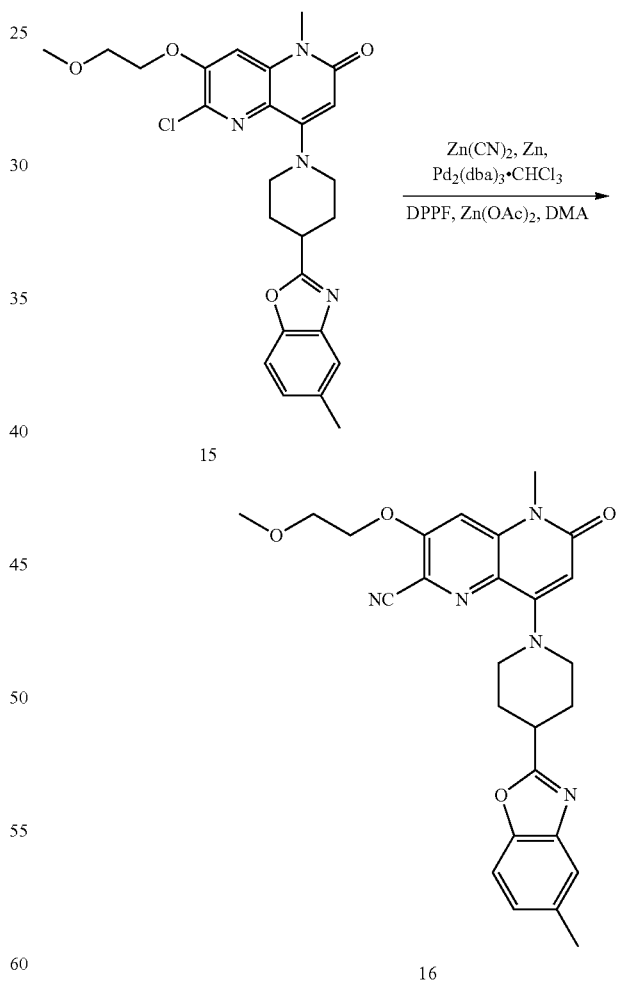

To a mixture of compound 15 (30 mg, 0.062 mmol) in DMA (1 mL) was added $Zn(CN)_2$ (36.5 mg, 0.31 mmol), Zn (4.1 mg, 0.062 mmol), $Zn(OAc)_2$ (11.4 mg, 0.062 mmol), $Pd_2(dba)_3$-$CHCl_3$ (32.2 mg, 0.031 mmol) and DPPF (17.5 mg, 0.031 mmol). The mixture was stirred at 160° C. for 2 h under microwave in a sealed tube. The mixture was poured into water (10 mL) and extracted with DCM (3×10 mL). The combined organic layers were dried over Na$_2$SO$_4$, filtered, and concentrated under reduced pressure. The resulting residue was purified by preparative HPLC separation to give example 16. LCMS: MS m/z (ESI) [M+H]$^+$=474.2. $^1$H NMR (400 MHz, DMSO) δ 7.57-7.53 (m, 2H), 7.50 (s, 1H), 7.17 (d, J=8.3 Hz, 1H), 6.01 (s, 1H), 4.54-4.48 (m, 2H), 4.08-4.00 (m, 2H), 3.80-3.75 (m, 2H), 3.55 (s, 3H), 3.36 (s, 3H), 3.31-3.27 (m, 1H), 3.14 (t, J=11.0 Hz, 2H), 2.41 (s, 3H), 2.25-2.17 (m, 2H), 2.08-1.96 (m, 2H).

Example 17: 6-chloro-7-((2-hydroxyethyl)amino)-1-methyl-4-(4-(5-methylbenzo[d]oxazol-2-yl)piperidin-1-yl)-1,5-naphthyridin-2(1H)-one

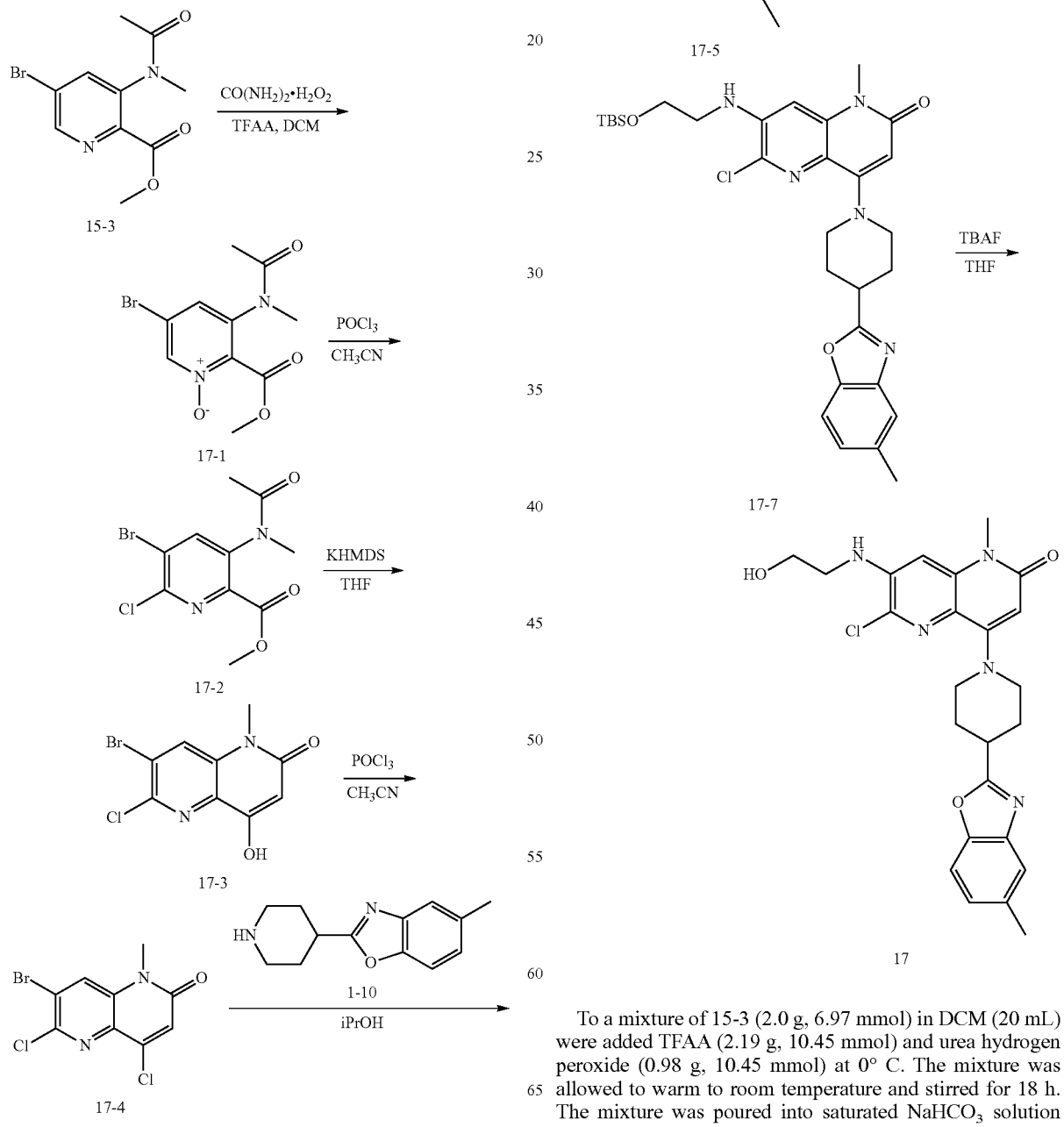

To a mixture of 15-3 (2.0 g, 6.97 mmol) in DCM (20 mL) were added TFAA (2.19 g, 10.45 mmol) and urea hydrogen peroxide (0.98 g, 10.45 mmol) at 0° C. The mixture was allowed to warm to room temperature and stirred for 18 h. The mixture was poured into saturated NaHCO$_3$ solution (150 mL) and extracted with DCM (150 mL×3). The organic layers were dried over Na$_2$SO$_4$, filtered, and concentrated in vacuo to give 17-1. LCMS: MS m/z (ESI) [M+H]$^+$=303.1. To a mixture of 17-1 (1.10 g, 3.63 mmol) in CH$_3$CN (10 mL) was added POCl$_3$ (1 mL, 10.76 mmol). The mixture was stirred at 80° C. for 18 h. The mixture was diluted with DCM (30 mL) and poured into saturated NaHCO$_3$ solution (100 mL). The mixture was extracted with DCM (100 mL×3). The organic layers were dried over Na$_2$SO$_4$, filtered, and concentrated in vacuo to give 17-2. LCMS: MS m/z (ESI) [M+H]$^+$=321.1.

To a mixture of 17-2 (1.00 g, 3.11 mmol) in THF (20 mL) was added KHMDS (3.73 mL, 1 M in THF) at −78° C. under N$_2$. The mixture was stirred at −78° C. for 2 h, then allowed to warm to room temperature and stirred for another 2 h under N$_2$. The mixture was poured into water (100 mL) and acidified with HCl (1 M, aq) to pH~4. The mixture was extracted with EtOAc (100 mL×3). The combined organic layers were dried over Na$_2$SO$_4$, filtered, and concentrated in vacuo to give 17-3. LCMS: MS m/z (ESI) [M+H]$^+$=288.8.

To a mixture of 17-3 (400 mg, 1.38 mmol) in CH$_3$CN (5 mL) was added POCl$_3$ (1 mL, 10.76 mmol). The mixture was stirred at 60° C. for 18 h under N$_2$. The mixture was diluted with DCM (30 mL) and poured into saturated NaHCO$_3$ solution (100 mL). The mixture was extracted with DCM (100 mL×3). The combined organic layers were dried over Na$_2$SO$_4$, filtered, and concentrated in vacuo to give 17-4. LCMS: MS m/z (ESI) [M+MeCN+H]$^+$=347.8.

A mixture of 17-4 (200 mg, 0.65 mmol), 1-10 (182.6 mg, 0.84 mmol) and DIEA (0.54 mL, 3.25 mmol) in isopropyl alcohol (5 mL) was stirred at 90° C. for 18 h. The mixture was concentrated in vacuo. The residue was purified by column chromatography on silica gel to give 17-5. LCMS: MS m/z (ESI) [M+H]$^+$=486.9.

A mixture of 17-5 (180 mg, 0.37 mmol), 17-6 (64.7 mg, 0.37 mmol), Pd$_2$(dba)$_3$ (16.9 mg, 0.018 mmol), Xantphos (21.4 mg, 0.037 mmol) and Cs$_2$CO$_3$ (360.7 mg, 1.11 mmol) in dioxane (3 mL) was stirred under N$_2$ at 80° C. for 18 h. The mixture was filtered through a celite pad and the filtrate was concentrated in vacuo. The resulting residue was purified by prep-TLC to give 17-7. LCMS: MS m/z (ESI) [M+H]$^+$=582.4.

To a mixture of 17-7 (60 mg, 0.10 mmol) in THF (3 mL) was added TBAF solution (0.21 mL, 1 M in THF). The mixture was stirred at room temperature for 4 h. The mixture was diluted with EtOAc (20 mL) and washed with H$_2$O (3×20 mL). The organic layer was dried over Na$_2$SO$_4$, filtered, and concentrated under reduced pressure. The resulting residue was purified by prep-HPLC separation to give example 17. LCMS: MS m/z (ESI) [M+H]$^+$=468.2. $^1$H NMR (400 MHz, DMSO) δ 7.56 (d, J=8.3 Hz, 1H), 7.50 (s, 1H), 7.24-7.10 (m, 1H), 6.89 (s, 1H), 6.05 (t, J=5.6 Hz, 1H), 5.77 (s, 1H), 4.99-4.83 (m, 1H), 4.14-3.96 (m, 2H), 3.70-3.63 (m, 2H), 3.50 (s, 3H), 3.39-3.35 (m, 2H), 3.30-3.25 (m, 1H), 3.14-3.09 (m, 2H), 2.42 (s, 3H), 2.23-2.14 (m, 2H), 2.07-1.94 (m, 2H).

Example 18: 3-((2-hydroxyethyl)amino)-5-methyl-8-(4-(5-methylbenzo[d]oxazol-2-yl)piperidin-1-yl)-6-oxo-5,6-dihydro-1,5-naphthyridine-2-carbonitrile

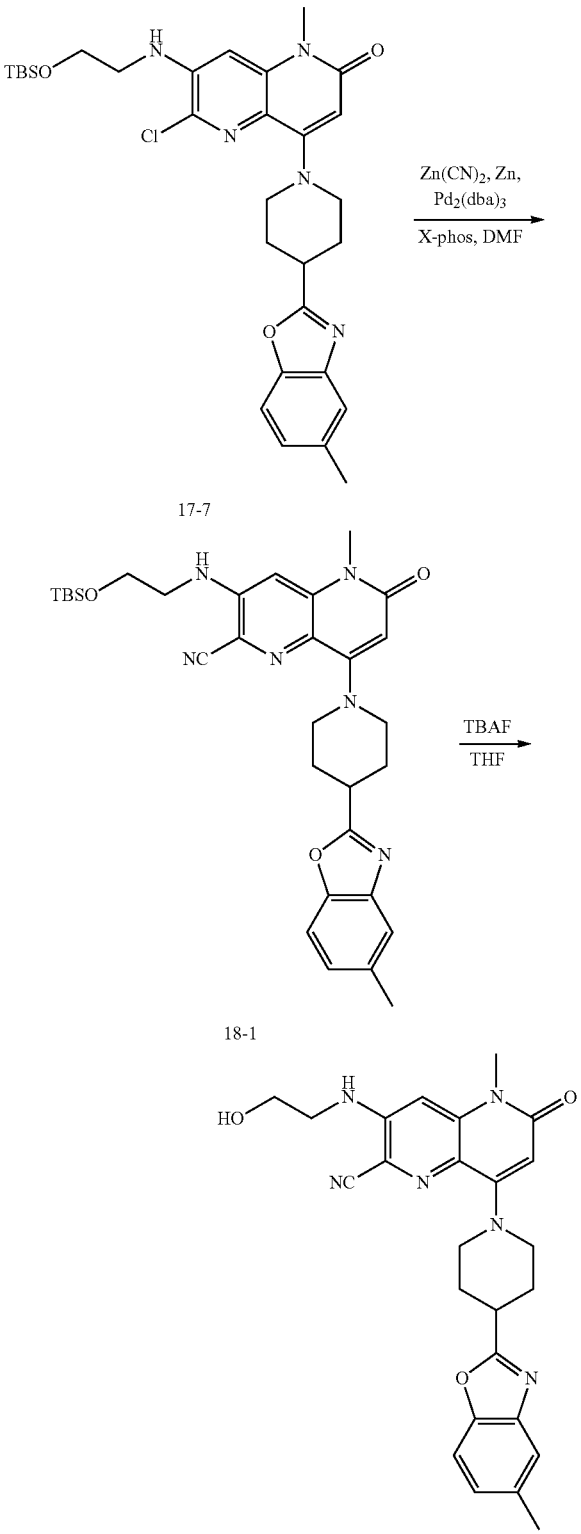

To a mixture of 17-7 (100 mg, 0.17 mmol) in DMF (5 mL) was added X-phos (16.4 mg, 0.034 mmol), Zn(CN)$_2$ (40.3 mg, 0.34 mmol), Zn (11 mg, 0.17 mmol) and Pd$_2$(dba)$_3$ (15.7 mg, 0.017 mmol). The reaction mixture was stirred at 120° C. for 1 h under microwave. The mixture was diluted with EtOAc (15 mL) and washed with H$_2$O (15 mL). The organic layer was dried over Na$_2$SO$_4$, filtered, and concentrated under reduced pressure. The resulting residue was purified by column chromatography on silica gel to give 18-1. LCMS: MS m/z (ESI) [M+H]$^+$=573.3.

To a solution of 18-1 (100 mg, 0.17 mmol) in THF (10 mL) was added TBAF (0.83 mL, 1.0 M in THF). The mixture was stirred at 25° C. for 18 h under N$_2$. The mixture was poured into water (100 mL) and extracted with DCM (3×50 mL). The combined organic layers dried over Na$_2$SO$_4$, filtered, and concentrated under reduced pressure. The resulting residue was purified by preparative HPLC separation to give example 18. LCMS: MS m/z (ESI) [M+H]$^+$=459.3. $^1$H NMR (400 MHz, DMSO) δ 7.55 (d, J=8.3 Hz, 1H), 7.50 (s, 1H), 7.17 (d, J=8.0 Hz, 1H), 6.94 (s, 1H), 6.60 (t, J=5.6 Hz, 1H), 5.82 (s, 1H), 4.90 (t, J=5.5 Hz, 1H), 4.03 (d, J=12.6 Hz, 2H), 3.64 (q, J=5.6 Hz, 2H), 3.47 (s, 3H), 3.40 (q, J=5.6 Hz, 2H), 3.30-3.26 (m, 1H), 3.10 (t, J=11.2 Hz, 2H), 2.41 (s, 3H), 2.19 (m, 2H), 2.00 (m, 2H).

Example 19: 7-((2-hydroxyethyl)amino)-1-methyl-4-(4-(5-methylbenzo[d]oxazol-2-yl)piperidin-1-yl)-1,5-naphthyridin-2(1H)-one

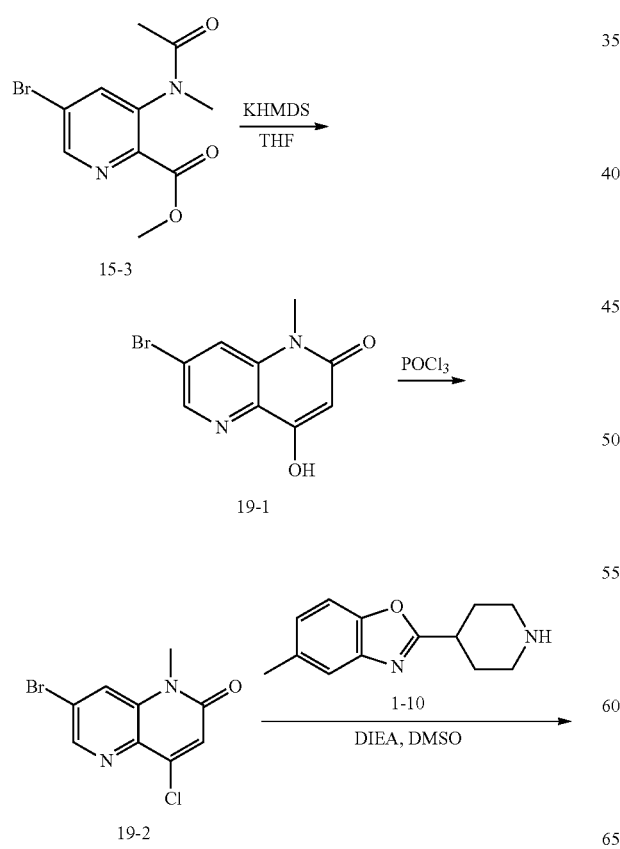

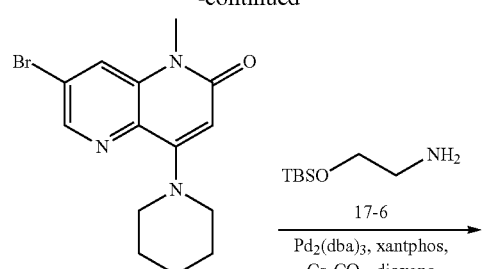

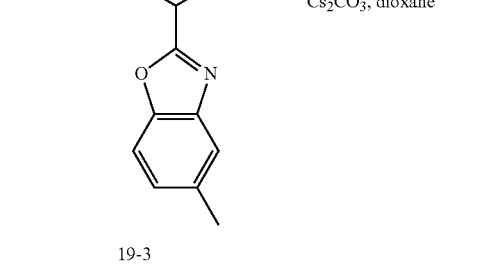

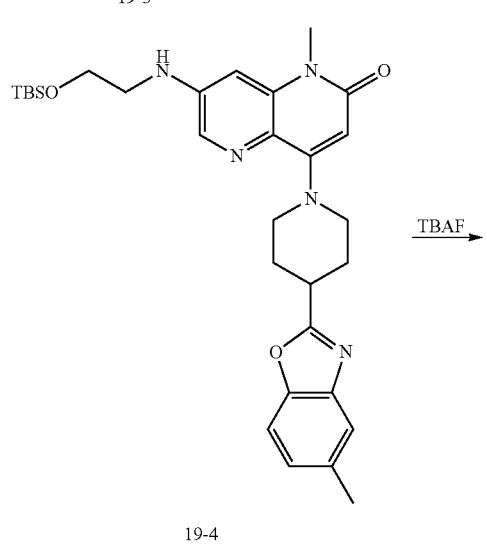

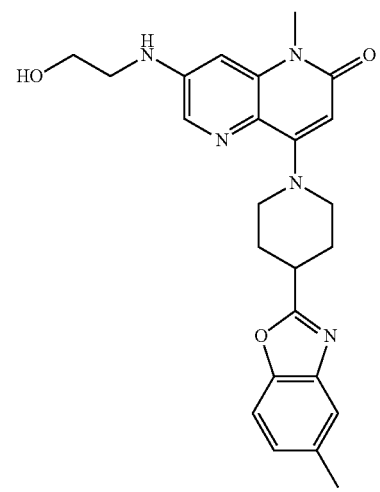

To a mixture of 15-3 (2.0 g, 6.97 mmol) in THF (20 mL) was added KHMDS (8.36 mL, 1 M in THF) at −78° C. The reaction mixture was stirred at room temperature for 3 h. The reaction mixture was quenched with saturated NH₄Cl solution (30 mL) and extracted with EtOAc (40 mL). The organic layer was dried over Na₂SO₄, filtered, and concentrated in vacuo to give 19-1. LCMS: MS m/z (ESI) [M+MeCN+H]⁺=295.9.

A mixture of 19-1 (1.2 g, 4.71 mmol) in POCl₃ (15 mL) was stirred at 85° C. for 2 h under N₂. The mixture was concentrated in vacuo. The residue was adjusted to pH=8-9 with saturated NaHCO₃ solution (30 mL) and extracted with DCM (30 mL). The organic layer was dried over Na₂SO₄, filtered, and concentrated in vacuo to give 19-2. LCMS: MS m/z (ESI) [M+H]⁺=273.0.

To a mixture of 19-2 (500 mg, 1.83 mmol) and 1-10 (474.5 mg, 2.19 mmol) in DMSO (10 mL) was added DIEA (1.81 mL, 10.97 mmol). The reaction mixture was stirred at 130° C. for 2 h. The reaction mixture was diluted with EtOAc (30 mL) and washed with brine (20 mL). The organic layer was dried over Na₂SO₄, filtered, and concentrated in vacuo. The resulting residue was purified by silica gel column chromatography to give 19-3. LCMS: MS m/z (ESI) [M+H]⁺=453.2.

To a mixture of 19-3 (240 mg, 0.53 mmol), 17-6 (185.7 mg, 1.06 mmol) and Cs₂CO₃ (517.5 mg, 1.59 mmol) in dioxane (10 mL) was added xantphos (61.3 mg, 0.11 mmol) and Pd₂(dba)₃ (97.0 mg, 0.11 mmol). The reaction was stirred at 100° C. for 16 h. The reaction mixture was diluted with EtOAc (30 mL) and washed with brine (20 mL). The organic layer was dried over Na₂SO₄, filtered, and concentrated in vacuo. The resulting residue was purified by silica gel column chromatography to give 19-4. LCMS: MS m/z (ESI) [M+H]⁺=548.4.

To a mixture of 19-4 (50 mg, 0.091 mmol) in THF (3 mL) was added TBAF (0.18 mL, 1 M in THF). The mixture was stirred at room temperature for 2 h. The mixture was diluted with EtOAc (20 mL) and washed with water (3×20 mL). The organic layers were dried over Na₂SO₄, filtered, and concentrated in vacuo. The resulting residue was purified by prep-HPLC separation to give example 19. LCMS: MS m/z (ESI) [M+H]⁺=434.2. ¹H NMR (400 MHz, DMSO) δ 8.00 (d, J=2.0 Hz, 1H), 7.55 (d, J=8.4 Hz, 1H), 7.50 (s, 1H), 7.17 (d, J=8.4 Hz, 1H), 6.72 (s, 1H), 6.59 (t, J=5.6 Hz, 1H), 5.71 (s, 1H), 4.80 (t, J=5.6 Hz, 1H), 4.10 (d, J=12.4 Hz, 2H), 3.65-3.58 (m, 2H), 3.45 (s, 3H), 3.30-3.24 (m, 3H), 3.11-2.98 (m, 2H), 2.41 (s, 3H), 2.22-2.12 (m, 2H), 2.09-1.89 (m, 2H).

Example 20: 6-chloro-1-methyl-4-(4-(5-methyl-benzo[d]oxazol-2-yl)piperidin-1-yl)-7-((tetrahydrofuran-3-yl)oxy)-1,5-naphthyridin-2(1H)-one

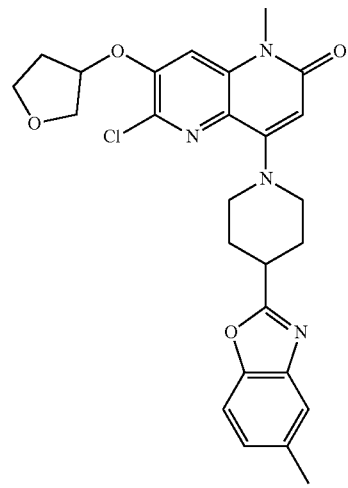

The preparation of example 20 referred to the similar procedure as example 15 with the intermediate 1-bromo-2-methoxyethane replaced by 3-bromotetrahydrofuran. LCMS: MS m/z (ESI) [M+H]⁺=495.1. ¹H NMR (400 MHz, DMSO) δ 7.56 (d, J=8.3 Hz, 1H), 7.50 (s, 1H), 7.42 (s, 1H), 7.17 (d, J=8.8 Hz, 1H), 5.96 (s, 1H), 5.48-5.42 (m, 1H), 4.08-4.00 (m, 2H), 3.98-3.76 (m, 5H), 3.56 (s, 3H), 3.15-3.06 (m, 2H), 2.41 (s, 3H), 2.38-2.28 (m, 1H), 2.25-2.16 (m, 2H), 2.12-1.95 (m, 3H).

Example 21: 5-methyl-8-(4-(5-methylbenzo[d]oxazol-2-yl)piperidin-1-yl)-6-oxo-3-((tetrahydrofuran-3-yl)oxy)-5,6-dihydro-1,5-naphthyridine-2-carbonitrile

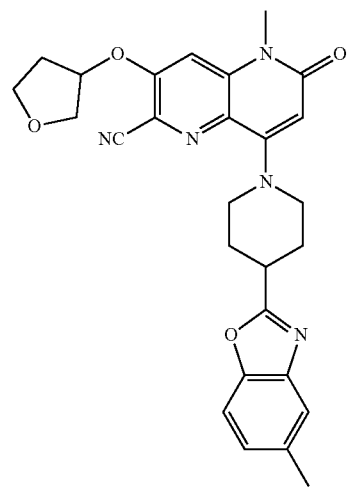 [SMILES: Cc1ccc2oc(C3CCN(c4cc(=O)n(C)c5cc(O[C@H]6CCOC6)c(C#N)nc45)CC3)nc2c1]

The preparation of example 21 referred to the similar procedure as example 16 with the reactant (example 15) replaced by example 20. LCMS: MS m/z (ESI) [M+H]⁺=486.3. ¹H NMR (400 MHz, DMSO) δ 7.55 (d, J=8.3 Hz, 1H), 7.49 (d, J=9.8 Hz, 2H), 7.17 (d, J=8.3 Hz, 1H), 6.01 (s, 1H), 5.58-5.50 (m, 1H), 4.08-4.00 (m, 2H), 3.99-3.88 (m, 3H), 3.86-3.78 (m, 1H), 3.56 (s, 3H), 3.38-3.33 (m, 1H), 3.14 (m, 2H), 2.41 (s, 3H), 2.37-2.29 (m, 1H), 2.25-2.16 (m, 2H), 2.13-1.98 (m, 3H).
Example 22: 6-chloro-7-(2-hydroxyethoxy)-1-methyl-4-(4-(5-methylbenzo[d]oxazol-2-yl)piperidin-1-yl)-1,5-naphthyridin-2(1H)-one
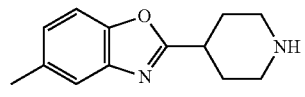
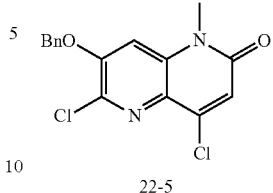
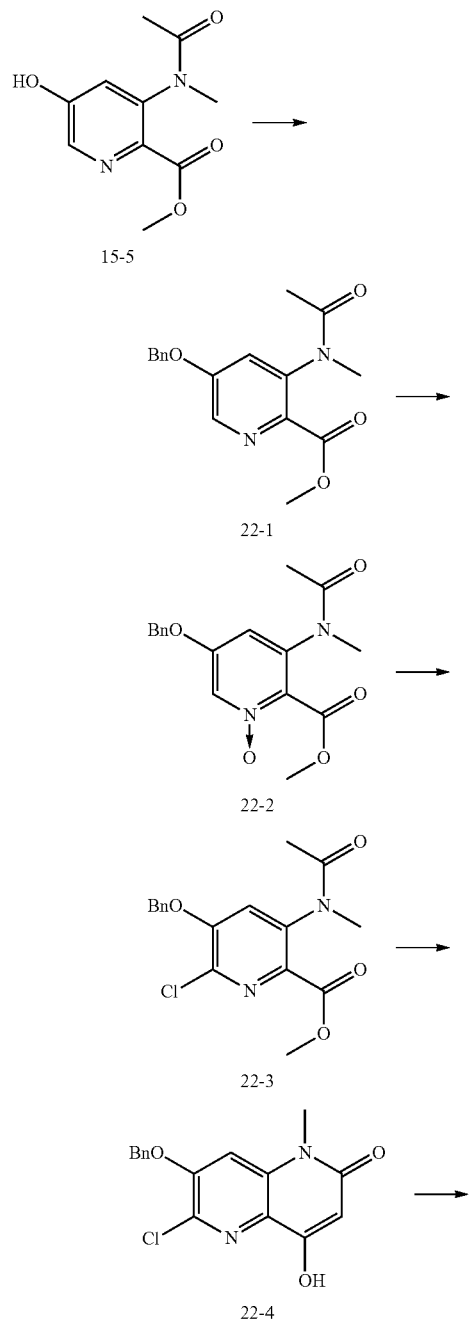
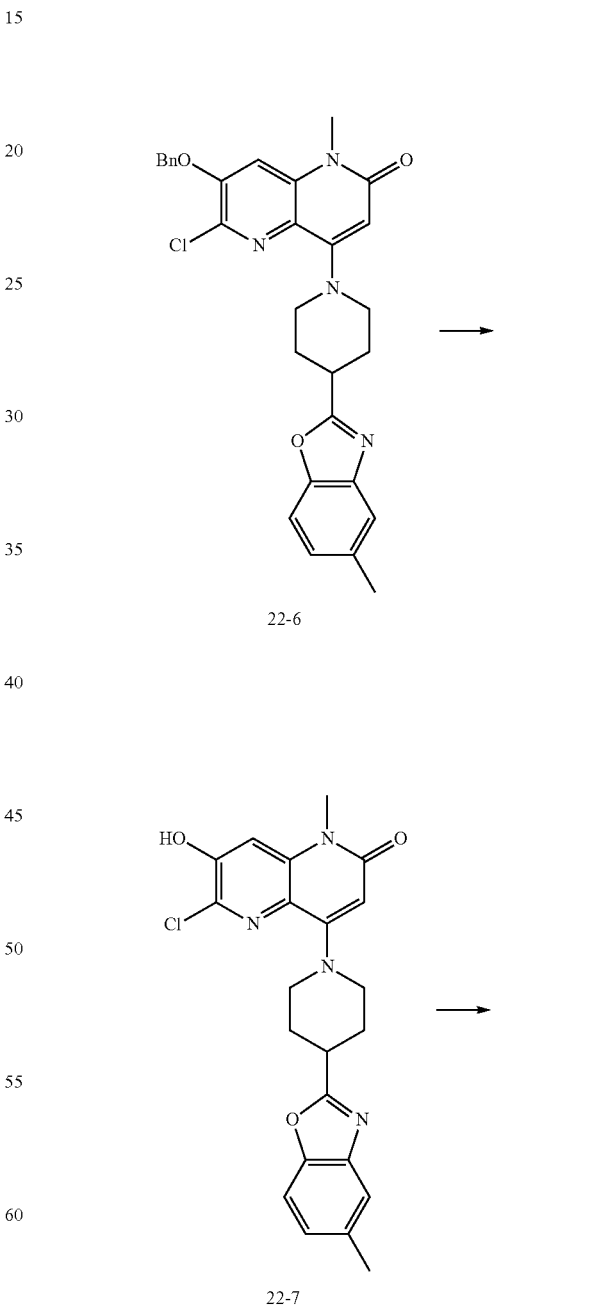

-continued

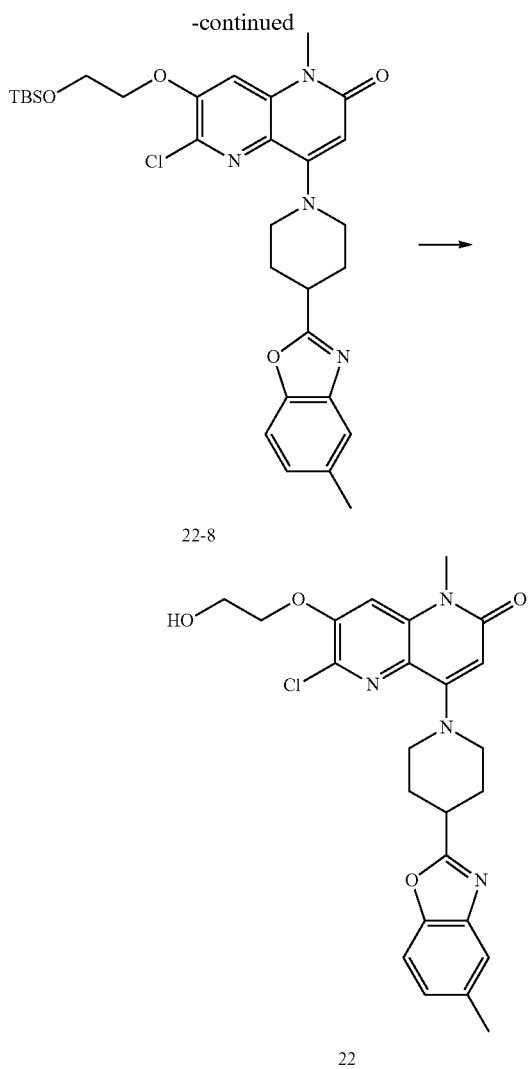

To a solution of 15-5 (7.0 g, 29.34 mmol) in DMF (100 mL) was added benzyl bromide (15.06 g, 88.04 mmol), $K_2CO_3$ (40.56 g, 293.46 mmol). The mixture was stirred at 60° C. for 3 h under $N_2$. The mixture was poured into water (80 mL) and extracted with DCM (3×50 mL). The combined organic layers were dried over $Na_2SO_4$, filtered, and concentrated under reduced pressure. The resulting residue was purified by silica gel column chromatography to give 22-1 (9.0 g, 97.6%). LCMS: MS m/z (ESI) $[M+H]^+=315.2$.

To a solution of 22-1 (9 g, 27.200 mmol) in DCE (200 mL) was added urea hydrogen peroxide (17.91 g, 190.4 mmol), TFAA (39.99 g, 190.4 mmol). The mixture was stirred at 70° C. for 2 h under $N_2$. After cooling to room temperature, the mixture was adjusted to pH=8.0 with sat. $NaHCO_3$(aq) and extracted with DCM (3×100 mL). The combined organic layers were dried over $Na_2SO_4$, filtered, and concentrated under reduced pressure. The resulting residue was purified by silica gel column chromatography to give 22-2 (8.0 g, 84.6%). LCMS: MS m/z (ESI) $[M+H]^+=331.1$.

To a solution of 22-2 (8.0 g, 23.01 mmol) in $CH_3CN$ (100 mL) was added $POCl_3$ (10.69 mL, 115.03 mmol). The mixture was stirred at 60° C. for 3 h under $N_2$. The mixture was concentrated under reduced pressure, adjusted to pH=8.0 with sat. $NaHCO_3$ (aq) and extracted with DCM (3×50 mL). The combined organic layers were dried over $Na_2SO_4$, filtered, and concentrated under reduced pressure to give 22-3 (7.0 g, 78.5%). LCMS: MS m/z (ESI) $[M+H]^+=349.0$.

To a solution of 22-3 (1.1 g, 3.00 mmol) in THF (30 mL) at 80° C. was added KHMDS (0.72 g, 3.60 mmol). The reaction mixture was stirred at 80° C. for 10 min under $N_2$. The mixture was adjusted to pH=6.0 with 1N HCl and concentrated under reduced pressure to give 22-4 (950 mg, 95.1%). LCMS: MS m/z (ESI) $[M+H]^+=317.0$.

A mixture of 22-4 (950 mg, 2.85 mmol) in $POCl_3$ (10 mL) was stirred at 85° C. for 3 h. The mixture was poured into ice-water (100 mL) and adjusted to pH=8.0 with saturated $NaHCO_3$ solution. The resulting mixture was extracted with DCM (50 mL×3). The combined organic layers were dried over $Na_2SO_4$, filtered, and concentrated under reduced pressure to give 22-5 (600 mg, 59.7%). LCMS: MS m/z (ESI) $[M+H]^+=334.8$.

To a solution of 22-5 (600 mg, 1.70 mmol) in i-PrOH (10 mL) was added 1-10 (735.6 mg, 3.40 mmol) and DIPEA (2.81 mL, 17.01 mmol). The mixture was stirred at 110° C. for 32 h under $N_2$. The mixture was poured into water (100 mL) and extracted with DCM (3×50 mL). The combined organic layers were dried over $Na_2SO_4$, filtered, and concentrated under reduced pressure. The resulting residue was purified by silica gel column chromatography to give 22-6 (440 mg, 47.7%). LCMS: MS m/z (ESI) $[M+H]^+=515.0$.

To a solution of 22-6 (550 mg, 1.03 mmol) in DCM (5 mL) at −78° C. was added $BBr_3$ (5.13 mL, 5.13 mmol). After stirring at room temperature for 18 h under $N_2$, the mixture was quenched by MeOH (10 mL) and adjusted to pH=8-9 with $NH_3$—$H_2O$ (0.5 mL). The resulting mixture was concentrated under reduced pressure to give the crude, which was purified by silica gel column chromatography to give compound 22-7 (300 mg, 66.8%). LCMS: MS m/z (ESI) $[M+H]^+=425.0$.

To a mixture of 22-7 (100 mg, 0.24 mmol) in DMF (10 mL) was added (2-bromoethoxy)(tert-butyl)dimethylsilane (169 mg, 0.72 mmol) and $Cs_2CO_3$ (383 mg, 1.18 mmol). After stirring at 100° C. for 3 h, the mixture was quenched with water (20 mL) and extracted with EtOAc (2×15 mL). The combined organic layers were washed with brine (3×30 mL), dried over $Na_2SO_4$, filtered, and concentrated under reduced pressure. The resulting residue was purified by column chromatography on silica gel to give compound 22-8 (50 mg, 36.4%). LCMS: MS m/z (ESI) $[M+H]^+=583.2$.

To a mixture of 22-8 (40 mg, 0.069 mmol) in THF (0.5 mL) was added TBAF (0.34 mL, 0.34 mmol). After stirring at room temperature for 1 h under $N_2$, the mixture was diluted with EtOAc (15 mL) and washed with water (3×20 mL). The organic layer was dried over $Na_2SO_4$, filtered, and concentrated under reduced pressure. The resulting residue was purified by prep-HPLC to give example 22 (2.37 mg). LCMS: MS m/z (ESI) $[M+H]^+=469.1$. $^1H$ NMR (400 MHz, DMSO) δ 7.65-7.40 (m, 3H), 7.23-7.13 (m, 1H), 5.95 (s, 1H), 5.04 (br s, 1H), 4.33 (m, 2H), 4.06 (m, 2H), 3.83 (m, 2H), 3.56 (s, 3H), 3.19-3.02 (m, 3H), 2.42 (s, 3H), 2.25-2.15 (m, 2H), 2.09-1.97 (m, 2H).

Example 23: 3-(2-hydroxyethoxy)-5-methyl-8-(4-(5-methylbenzo[d]oxazol-2-yl)piperidin-1-yl)-6-oxo-5,6-dihydro-1,5-naphthyridine-2-carbonitrile

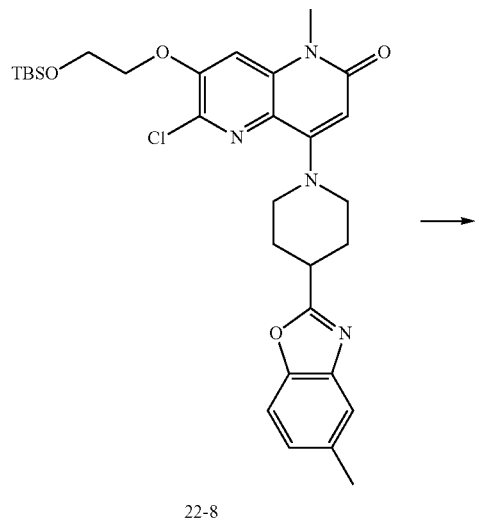

22-8

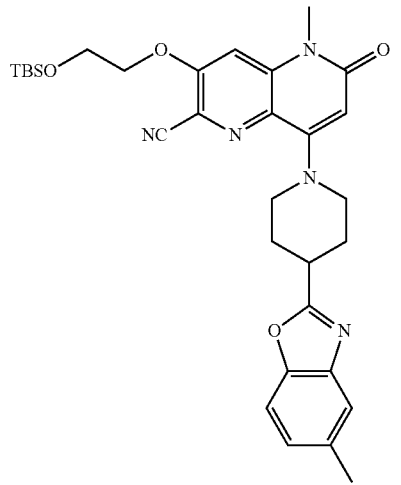

23-1

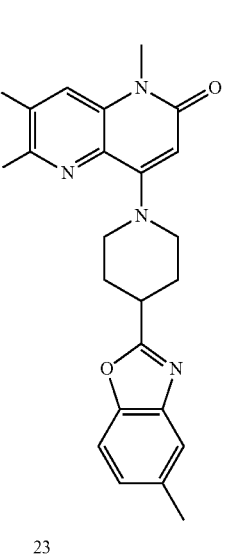

23

To a mixture of 22-8 (50 mg, 0.086 mmol) in DMA (1 mL) was added Zn(CN)$_2$ (50.5 mg, 0.43 mmol), Zn (5.61 mg, 0.086 mmol), zinc bis(acetate) (15.7 mg, 0.086 mmol), dppf (23.8 mg, 0.043 mmol) and Pd(dba)$_3$-CHCl$_3$ (34.8 mg, 0.043 mmol). The mixture was stirred at 160° C. under microwave condition for 1.5 h. The mixture was diluted with ethyl acetate (20 mL) and filtered through a celite pad. The filtrate was washed with brine (3×20 mL), dried over Na$_2$SO$_4$, filtered, and concentrated under reduced pressure. The resulting residue was purified by column chromatography on silica gel to give compound 23-1. LCMS: MS m/z (ESI) [M+H]$^+$=574.0.

To a mixture of 23-1 (100 mg, 0.17 mmol) in THF (4 mL) was added TBAF (0.35 mL, 0.35 mmol). After stirring at room temperature for 1 h, the mixture was diluted with EtOAc (15 mL) and washed with water (3×20 mL). The organic layer was dried over Na$_2$SO$_4$, filtered, and concentrated under reduced pressure. The resulting residue was purified by prep-HPLC to give example 23 (10.6 mg). LCMS: MS m/z (ESI) [M+H]$^+$=460.0. $^1$H NMR (400 MHz, DMSO) δ 7.58-7.52 (m, 2H), 7.50 (s, 1H), 7.17 (d, J=8.3 Hz, 1H), 6.01 (s, 1H), 5.06 (t, J=5.2 Hz, 1H), 4.40 (t, J=4.7 Hz, 2H), 4.08-3.98 (m, 2H), 3.88-3.78 (m, 2H), 3.55 (s, 3H), 3.29-3.24 (m, 1H), 3.18-3.08 (m, 2H), 2.41 (s, 3H), 2.25-2.16 (m, 2H), 2.09-1.94 (m, 2H).

Example 24: 3-(3-hydroxypropoxy)-5-methyl-8-(4-(5-methylbenzo[d]oxazol-2-yl)piperidin-1-yl)-6-oxo-5,6-dihydro-1,5-naphthyridine-2-carbonitrile

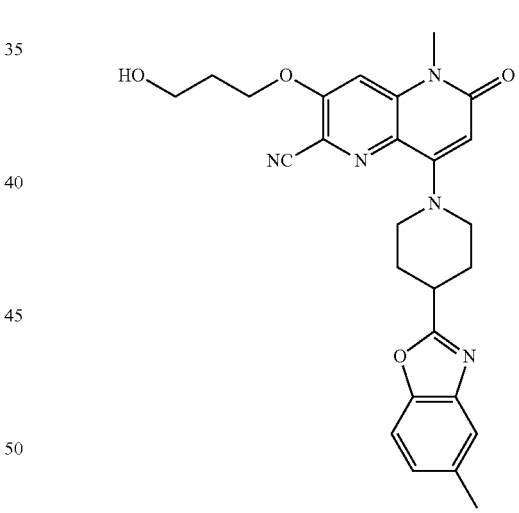

24

The preparation of example 24 referred to the similar procedure as example 23 with the reactant 1-(2-bromoethoxy)(tert-butyl)dimethylsilane replaced by (3-bromopropoxy)(tert-butyl)dimethylsilane. LCMS: MS m/z (ESI) [M+H]$^+$=474.1. $^1$H NMR (400 MHz, DMSO) δ 7.55 (d, J=8.3 Hz, 1H), 7.52 (s, 1H), 7.50 (s, 1H), 7.20-7.15 (m, 1H), 6.01 (s, 1H), 4.67 (t, J=5.1 Hz, 1H), 4.42 (t, J=6.2 Hz, 2H), 4.04 (d, J=12.7 Hz, 2H), 3.62 (m, 2H), 3.56 (s, 3H), 3.34 (m, 1H), 3.14 (t, J=11.0 Hz, 2H), 2.41 (s, 3H), 2.26-2.16 (m, 2H), 2.08-1.92 (m, 4H).

Example 25: 5-methyl-8-(4-(5-methylbenzo[d]oxazol-2-yl)piperidin-1-yl)-6-oxo-3-((tetrahydro-2H-pyran-4-yl)oxy)-5,6-dihydro-1,5-naphthyridine-2-carbonitrile

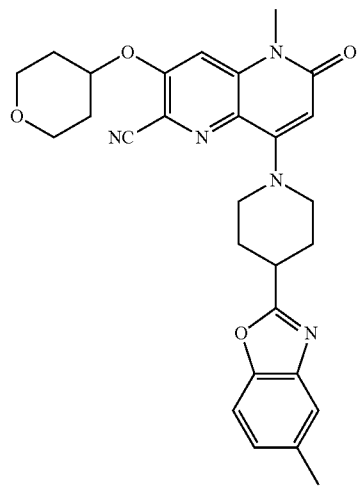

The preparation of example 25 referred to the similar procedure as example 23 with the reactant 1-(2-bromoethoxy)(tert-butyl)dimethylsilane replaced by 4-bromotetrahydro-2H-pyran. LCMS: MS m/z (ESI) [M+H]$^+$=500.4. $^1$H NMR (400 MHz, DMSO) δ 7.59-7.54 (m, 2H), 7.50 (s, 1H), 7.17 (dd, J=8.3, 1.1 Hz, 1H), 6.01 (s, 1H), 5.21-5.12 (m, 1H), 4.04 (d, J=12.7 Hz, 2H), 3.92-3.84 (m, 2H), 3.67-3.56 (m, 2H), 3.55 (s, 3H), 3.31-3.26 (m, 1H), 3.14 (t, J=10.9 Hz, 2H), 2.42 (s, 3H), 2.26-2.17 (m, 2H), 2.11-1.95 (m, 4H), 1.78-1.66 (m, 2H).

Example 26: 3-(2-aminoethoxy)-5-methyl-8-(4-(5-methylbenzo[d]oxazol-2-yl)piperidin-1-yl)-6-oxo-5,6-dihydro-1,5-naphthyridine-2-carbonitrile

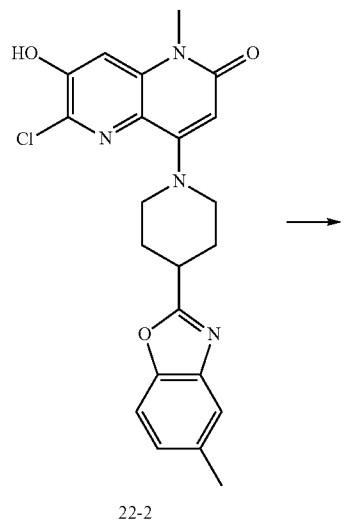

22-2

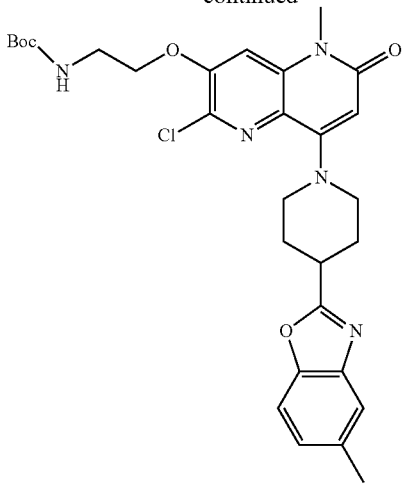

26-1

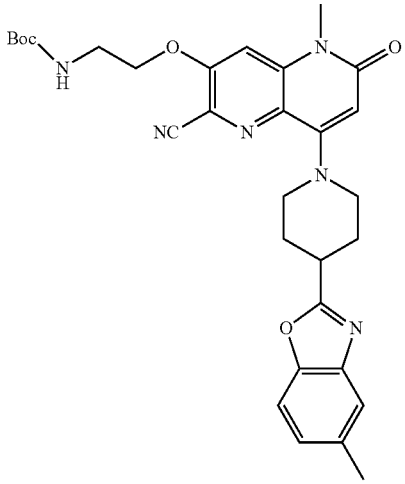

26-2

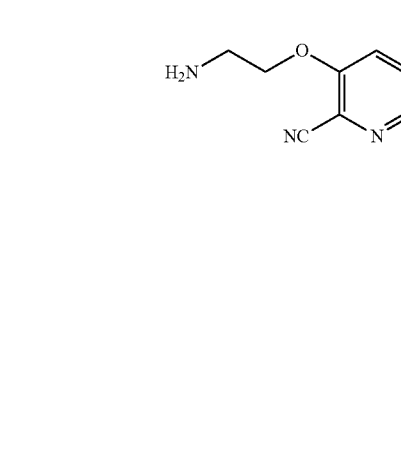

26

To a solution of 22-2 (100 mg, 0.22 mmol) in DMF (15 mL) was added tert-butyl (2-bromoethyl)carbamate (245 mg, 1.09 mmol) and Cs$_2$CO$_3$ (428 mg, 1.31 mmol). After stirring at 100° C. for 2 h under N$_2$, the mixture was diluted with EtOAc (20 mL) and washed with H$_2$O (3×20 mL). The organic layer was dried over Na$_2$SO$_4$, filtered, and concentrated under reduced pressure. The resulting residue was purified by silica gel column chromatography to give 26-1 (80 mg, 62.4%). LCMS: MS m/z (ESI) [M+H]⁺=568.2.

To a mixture of 26-2 (70 mg, 0.12 mmol) in DMA (2 mL) was added Zn(CN)₂ (68.7 mg, 0.59 mmol), Zn (1.53 mg, 0.023 mmol), Pd₂(dba)₃-CHCl₃ (24.23 mg, 0.023 mmol), Zn(OAc)₂ (4.30 mg, 0.023 mmol) and DPPF (13.22 mg, 0.023 mmol). After stirring at 120° C. for 1 h under N₂, the mixture was diluted with EtOAc (20 mL) and washed with H₂O (3×20 mL). The organic layer was dried over Na₂SO₄, filtered, and concentrated under reduced pressure. The resulting residue was purified by silica gel column chromatography to give 26-2 (30 mg, 41.3%). LCMS: MS m/z (ESI) [M+H]⁺=559.3.

To a solution of 26-2 (30 mg, 0.051 mmol) in DCM (1 mL) was added TFA (116 mg). After stirring at 25° C. for 18 h. The mixture was adjusted to pH=8.0 with sat. NaHCO₃ solution and extracted with DCM (3×15 mL). The combined organic layers were dried over Na₂SO₄, filtered, and concentrated under reduced pressure. The resulting residue was purified by prep-HPLC to give example 26 (7.7 mg). LCMS: MS m/z (ESI) [M+H]⁺=459.2. ¹H NMR (400 MHz, DMSO) δ 7.56 (d, J=8.3 Hz, 1H), 7.51 (d, J=7.3 Hz, 2H), 7.17 (d, J=8.2 Hz, 1H), 6.01 (s, 1H), 4.37-4.30 (m, 2H), 4.08-3.99 (m, 2H), 3.56 (s, 3H), 3.27-3.21 (m, 2H), 3.18-3.09 (m, 3H), 3.06-2.98 (m, 2H), 2.41 (s, 3H), 2.24-2.17 (m, 2H), 2.06-1.97 (m, 2H).

Example 27: 5-methyl-8-(4-(5-methylbenzo[d]oxazol-2-yl)piperidin-1-yl)-6-oxo-3-(pyrrolidin-3-yloxy)-5,6-dihydro-1,5-naphthyridine-2-carbonitrile

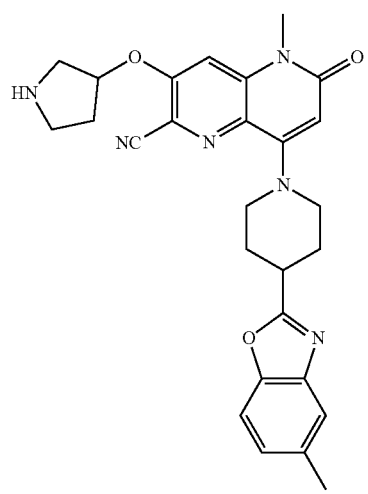

27

The preparation of example 27 referred to the similar procedure as example 26 with the reactant tert-butyl (2-bromoethyl)carbamate replaced by tert-butyl 3-bromopyrrolidine-1-carboxylate. LCMS: MS m/z (ESI) [M+H]⁺=485.2. ¹H NMR (400 MHz, DMSO) δ 8.36 (s, 1H), 7.52 (d, J=8.3 Hz, 1H), 7.49-7.40 (m, 2H), 7.16 (d, J=8.2 Hz, 1H), 6.04-5.91 (m, 1H), 5.52-5.34 (m, 1H), 4.02 (d, J=12.3 Hz, 2H), 3.54 (s, 3H), 3.45-3.41 (m, 1H), 3.34-3.22 (m, 2H), 3.19-3.04 (m, 4H), 2.39 (s, 3H), 2.26-2.15 (m, 3H), 2.14-1.92 (m, 3H).

Example 28: (R)-5-methyl-8-(4-(5-methylbenzo[d]oxazol-2-yl)piperidin-1-yl)-6-oxo-3-((tetrahydrofuran-3-yl)oxy)-5,6-dihydro-1,5-naphthyridine-2-carbonitrile

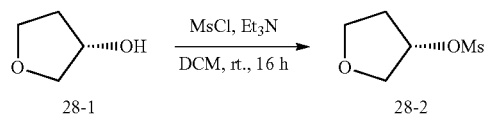

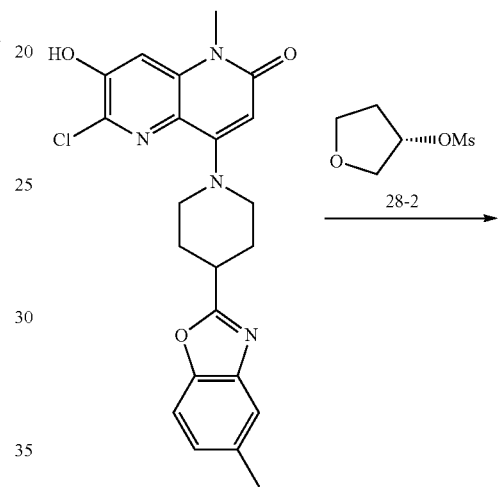

22-2

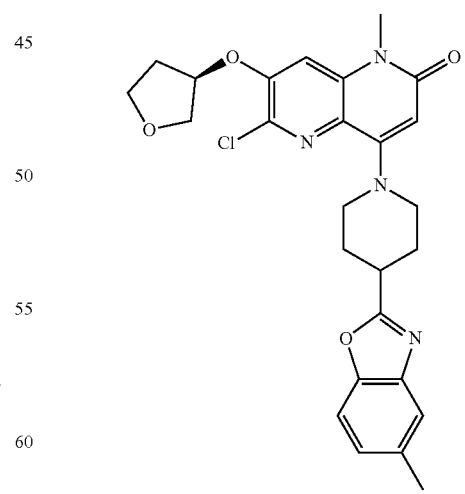

28-3

-continued

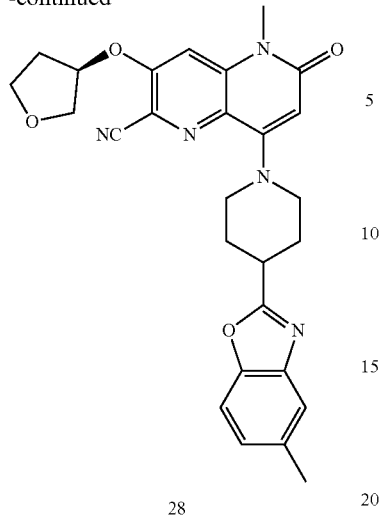

28

To a solution of 28-1 (500 mg, 5.68 mmol) in dry DCM (15 mL) was added Et₃N (1.72 g, 2.37 mL, 17.0 mmol) and MsCl (975 mg, 8.51 mmol) under N₂. After stirring at room temperature for 16 h, the mixture was added DCM (20 mL) and washed with water (20 mL×2) and brine (15 mL). The organic layer was dried over Na₂SO₄, filtered, and concentrated under reduced pressure to afford compound 28-2 (900 mg), which was used for next step without further purification.

To a solution of 22-2 (100 mg, 0.24 mmol) and 28-2 (117 mg, 0.71 mmol) in DMF (5 mL) was added Cs₂CO₃ (460 mg, 1.41 mmol). After stirring at 100° C. for 3 h, the reaction mixture was diluted with EtOAc (20 mL), washed with water (20 mL×3) and brine (20 mL). The organic layer was dried over Na₂SO₄, filtered, and concentrated under reduced pressure. The resulting residue was purified by column chromatography on silica gel eluting to give compound 28-3 (65 mg, 55.8%). LCMS: MS m/z (ESI) [M+H]⁺=495.3.

A mixture of 28-3 (70 mg, 0.14 mmol), Zn (9.25 mg, 0.14 mmol), Zn(CN)₂ (16.6 mg, 0.14 mmol), Zn(OAc)₂ (25.9 mg, 0.14 mmol), dppf (77.9 mg, 0.14 mmol) and Pd₂dba₃-CHCl₃ (146.2 mg, 0.14 mmol) in DMA (2 mL) was stirred at 150° C. under microwave condition for 1 h. The mixture was quenched with water (10 mL) and extracted with EtOAc (3×10 mL). The combined organic layers were washed with water (15 mL) and brine (15 mL). The organic layer was dried over Na₂SO₄, filtered, and concentrated under reduced pressure. The resulting residue was purified by prep-HPLC to give example 28 (26.5 mg, 38.6%). LCMS: MS m/z (ESI) [M+H]⁺=486.2. ¹H NMR (400 MHz, DMSO) δ 7.55 (d, J=8.0 Hz, 1H), 7.50-7.48 (m, 2H), 7.17 (d, J=8.0 Hz, 1H), 6.02 (s, 1H), 5.57-5.48 (m, 1H), 4.05-4.02 (m, 2H), 3.97-3.96 (m, 2H), 3.95-3.93 (m, 1H), 3.83-3.81 (m, 1H), 3.56 (s, 3H), 3.32-3.25 (m, 1H), 3.19-3.10 (m, 2H), 2.42 (s, 3H), 2.37-2.33 (m, 1H), 2.22-2.20 (m, 2H), 2.12-2.00 (m, 3H).

Example 29: (S)-5-methyl-8-(4-(5-methylbenzo[d]oxazol-2-yl)piperidin-1-yl)-6-oxo-3-((tetrahydrofuran-3-yl)oxy)-5,6-dihydro-1,5-naphthyridine-2-carbonitrile

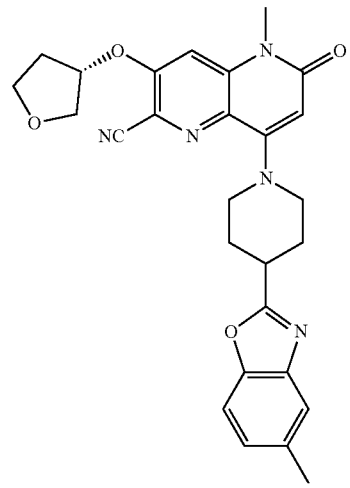

29

The preparation of example 29 referred to the similar procedure as example 28 with the reactant (S)-tetrahydrofuran-3-ol replaced by (R)-tetrahydrofuran-3-ol. LCMS: MS m/z (ESI) [M+H]⁺=486.2. ¹H NMR (400 MHz, DMSO) δ 7.55 (d, J=8.4 Hz, 1H), 7.49 (d, J=9.4 Hz, 2H), 7.17 (d, J=8.2 Hz, 1H), 6.02 (s, 1H), 5.59-5.49 (m, 1H), 4.09-3.98 (m, 2H), 3.97-3.88 (m, 3H), 3.85-3.75 (m, 1H), 3.56 (s, 3H), 3.33-3.25 (m, 1H), 3.20-3.09 (m, 2H), 2.42 (s, 3H), 2.40-2.27 (m, 1H), 2.26-2.14 (m, 2H), 2.13-1.95 (m, 3H).

Example 30: 3-(2-hydroxyethoxy)-5-methyl-8-(1-(5-methylbenzo[d]oxazol-2-yl)-1,2,3,6-tetrahydropyridin-4-yl)-6-oxo-5,6-dihydro-1,5-naphthyridine-2-carbonitrile

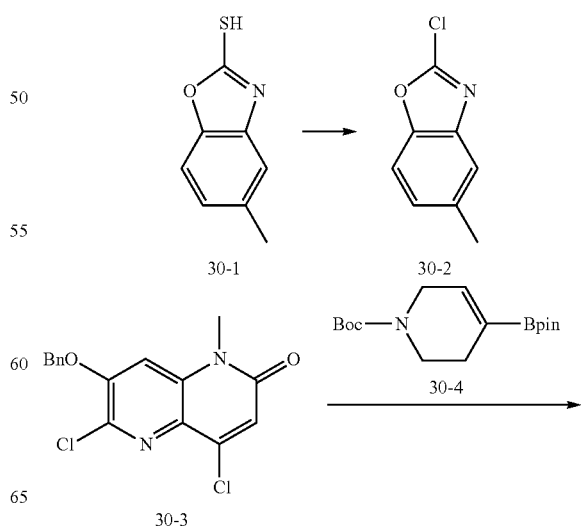

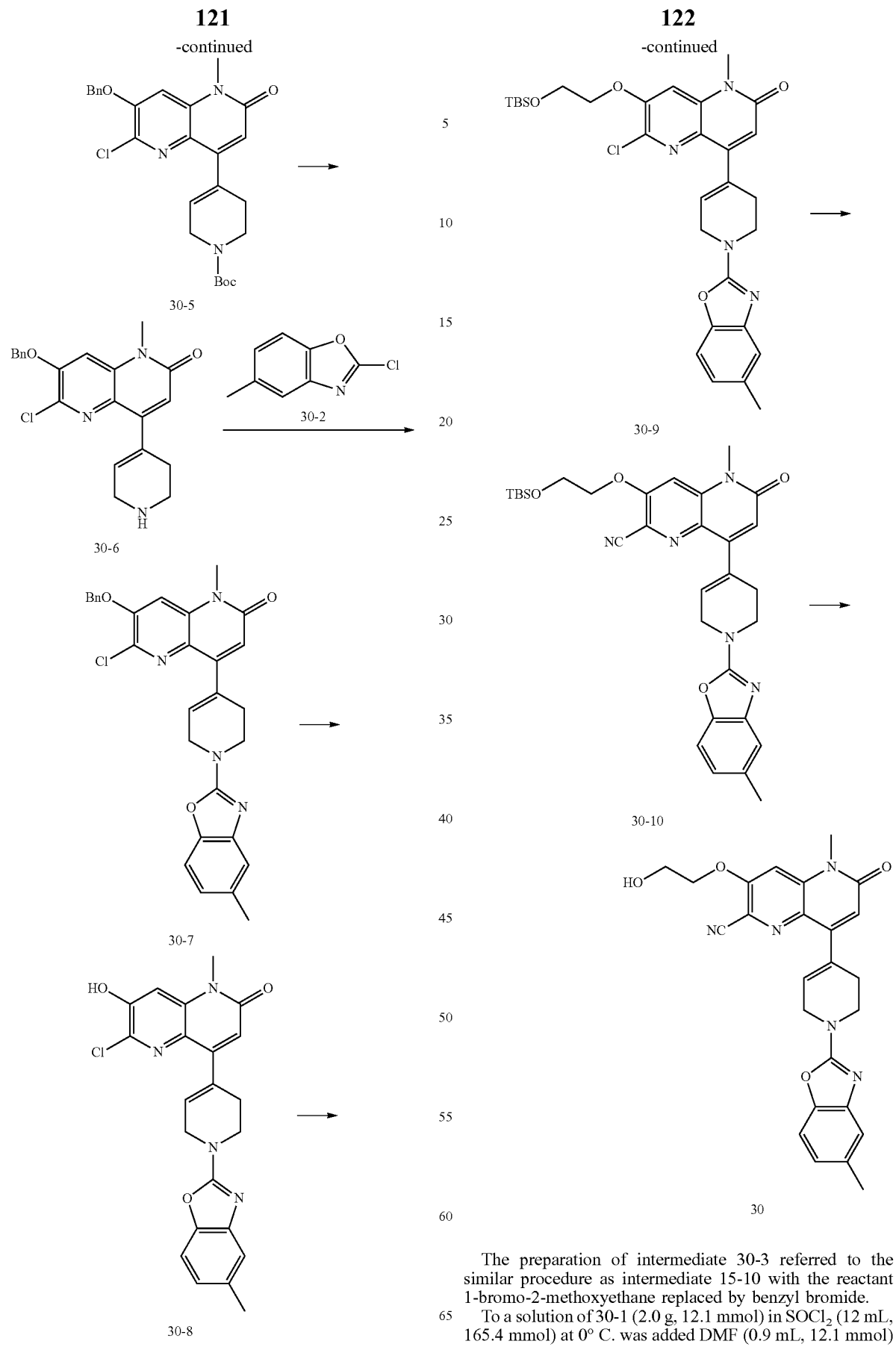
The preparation of intermediate 30-3 referred to the similar procedure as intermediate 15-10 with the reactant 1-bromo-2-methoxyethane replaced by benzyl bromide.
To a solution of 30-1 (2.0 g, 12.1 mmol) in $SOCl_2$ (12 mL, 165.4 mmol) at 0° C. was added DMF (0.9 mL, 12.1 mmol) dropwise. After stirring at room temperature for 0.5 h, the mixture was concentrated under reduced pressure. The residue was dissolved with DCM (30 mL) and neutralized with Sat. Na$_2$CO$_3$ to pH=7. The organic layer was washed with water (10 mL) and brine (10 mL), dried over Na$_2$SO$_4$, and concentrated to give crude product, which was purified by column chromatography on silica gel to give 30-2 (1.2 g, 59.2%). LCMS: MS m/z (ESI) [M+H]$^+$=168.0.

A mixture of 30-3 (500 mg, 1.49 mmol), 30-4 (369 mg, 1.19 mmol), K$_2$CO$_3$ (618 mg, 4.48 mmol) and Pd(dppf)Cl$_2$ (54.6 mg, 0.075 mmol) in dioxane (8 mL) and H$_2$O (0.8 mL) was stirred at 80° C. for 2 h under N$_2$. The reaction mixture was added with H$_2$O (10 mL) and extracted with EtOAc (10 mL×3). The combined organic layers were washed by brine (30 mL×2), dried over Na$_2$SO$_4$, filtered, and concentrated under reduced pressure. The resulting residue was purified by C$_{18}$ reverse phase column chromatography to give compound 30-5 (200 mg, 27.8%). LCMS: MS m/z (ESI) [M+H]$^+$=482.2. $^1$H NMR (400 MHz, CDCl$_3$) δ 7.48-7.26 (m, 5H), 7.00 (d, J=8.3 Hz, 1H), 6.56 (d, J=4.1 Hz, 1H), 6.07 (s, 1H), 5.23 (s, 2H), 4.07-4.01 (m, 2H), 3.58 (t, J=5.5 Hz, 2H), 3.51 (s, 3H), 2.62-2.50 (m, 2H), 1.48-1.37 (s, 9H).

To a solution of 30-5 (170 mg, 0.35 mmol) in DCM (2.5 mL) was added TFA (0.5 mL). After stirring at room temperature for 1 h, the mixture was concentrated under reduced pressure to give compound 30-6 (170 mg), which was used for the next step without further purification. LCMS: MS m/z (ESI) [M+H]$^+$=382.0.

To a mixture of 30-6 (170 mg, 0.31 mmol) and 30-2 (105 mg, 0.63 mmol) in DMF (3 mL) was added DIEA (0.52 mL, 3.12 mmol). After stirring at 70° C. for 2 h, the mixture was added with water (10 mL) and extracted with EtOAc (10 mL×3). The combined organic layers were washed by water (10 mL×2) and brine (10 mL), dried over Na$_2$SO$_4$, filtered, and concentrated under reduced pressure. The resulting residue was purified by column chromatography on silica gel to give compound 30-7 (120 mg, 75.1%). LCMS: MS m/z (ESI) [M+H]$^+$=513.3.

To a solution of 30-7 (195 mg, 0.38 mmol) in DCM (5 mL) was added BBr$_3$ (1.0 mL, 1M in DCM) dropwise at 0° C. After stirring at room temperature for 1 h, the mixture was diluted with DCM (20 mL) and quenched with MeOH (1 mL) dropwise at −78° C. The mixture was washed with water (2×10 mL) and brine (10 mL), dried over Na$_2$SO$_4$, filtered, and concentrated under reduced pressure. The resulting residue was purified by column chromatography on silica gel to give 30-8 (120 mg, 74.7%). LCMS: MS m/z (ESI) [M+H]$^+$=423.0.

To a solution of 30-8 (100 mg, 0.24 mmol) in DMF (8 mL) was added Cs$_2$CO$_3$ (462 mg, 1.42 mmol) and (2-bromoethoxy)(tert-butyl)dimethylsilane (170 mg, 0.71 mmol). After stirring at 100° C. for 3 h, the reaction mixture was diluted with EtOAc (20 mL), washed with water (10 mL×3) and brine (10 mL), dried over Na$_2$SO$_4$, filtered, and concentrated under reduced pressure. The resulting residue was purified by column chromatography on silica gel to give compound 30-9 (55 mg, 40.0%). LCMS: MS m/z (ESI) [M+H]$^+$=581.3.

A mixture of 30-9 (50 mg, 0.086 mmol), Zn (6 mg, 0.092 mmol), Zn(CN)$_2$ (20 mg, 0.171 mmol), Zn(OAc)$_2$ (15 mg, 0.082 mmol), dppf (40 mg, 0.087 mmol) and Pd$_2$(dba)$_3$ (25 mg, 0.027 mmol) in DMA (1 mL) was stirred at 150° C. in a sealed tube under microwave condition for 1 h. The mixture was diluted with EtOAc (15 mL), washed with water (10 mL×2) and brine (10 mL), dried over Na$_2$SO$_4$, filtered, and concentrated under reduced pressure to give crude product 30-10, which was used for the next step without further purification. LCMS: MS m/z (ESI) [M+H]$^+$=515.4.

To a solution of 30-10 (50 mg, 0.052 mmol) in THF (2 mL) was added TBAF (0.15 mL, 1 M in THF). After stirring at room temperature for 1 h, the mixture was diluted with EtOAc (15 mL), and then washed with H$_2$O (10×2) and brine (10 mL), dried over Na$_2$SO$_4$, filtered, and concentrated under reduced pressure. The resulting residue was purified by prep-HPLC to give example 30 (6.9 mg). LCMS: MS m/z (ESI) [M+H]$^+$=458.1. $^1$H NMR (400 MHz, DMSO) δ 7.63 (s, 1H), 7.29 (d, J=8.1 Hz, 1H), 7.12 (s, 1H), 6.83 (d, J=8.1 Hz, 1H), 6.67 (s, 1H), 6.26 (s, 1H), 5.12-5.00 (m, 1H), 4.42 (t, J=4.6 Hz, 2H), 4.34-4.23 (m, 2H), 3.91-3.76 (m, 4H), 3.63 (s, 3H), 2.76-2.65 (m, 2H), 2.34 (s, 3H).

Example A: DGKA Inhibition ADP-Glo Assay

The DGKA inhibition reactions were performed using ADP-Glo assay. The reactions were carried out in 50 mM HEPES, 100 mM NaCl, 10 mM MgCl$_2$, 1 mM CaCl$_2$, 0.005% TritonX-100 and 1 mM DTT as working solution (pH=7.5). 30 nL DMSO solution of each test compound (Top concentration 0.4 μM with 10 point, 4-fold dilution series for each compound) were transferred to 384 well plate by Echo and 5 μL DGKA (SignalChem, D21-10BG) enzyme working solution at 2× final reaction concentration was added to each well. After incubated at 25° C. for 15 minutes, 5 μL substrate working solution contain 40 μM ATP (Promega, V915B) and 200 μM DLG (SignalChem, D430-59) were added to initiate reaction. After enzymatic reaction at 25° C. for 60 min, ADP Glo assay reagents (Promega, V9102) were added and luminescence was recorded using an EnVision following the instruction of manual. The percent inhibition was calculated from luminescence by no enzyme control reactions for 100% inhibition and DMSO only reactions for 0% inhibition. The IC$_{50}$ value was calculated via a regression analysis of the inhibition rate.

The data for Example A is shown in Table 3.

TABLE 3

| Example | DGKA IC$_{50}$ (nM) |
|---|---|
| 1 | 1.99 |
| 2 | 0.47 |
| 3 | 2.35 |
| 4 | 4.43 |
| 5 | 103 |
| 6 | 1.23 |
| 7 | 15.97 |
| 8 | 7.74 |
| 9 | 2.04 |
| 10 | 0.36 |
| 11 | 0.66 |
| 12 | 1.35 |
| 13 | 4.11 |
| 14 | 143.0 |
| 15 | 0.19 |
| 16 | 0.35 |
| 17 | 0.12 |
| 18 | 0.10 |
| 19 | 2.36 |
| 20 | 0.13 |
| 21 | 0.23 |
| 22 | 0.15 |
| 23 | 0.27 |
| 24 | 0.31 |
| 25 | 5.29 |
| 26 | 3.34 |
| 27 | 13.6 |
| 28 | 0.14 |

TABLE 3-continued

| Example | DGKA IC$_{50}$ (nM) |
|---|---|
| 29 | 0.70 |
| 30 | 0.65 |

Example B: IL-2 Release Detection Assay

Isolate Human Pan T cells from PBMC according to T cell isolation kit (Stemcell, 17951). The suspend T cell in RPMI 1640 medium containing 10% FBS, 1% PS and 55 μM β-Mer at a density of 3*10^6 cells/well/3 ml are seeded into 6 well plate, recovered overnight at 37° C.&5% CO$_2$. Harvest overnight recovered T cells are suspended in fresh RPMI1640 medium containing 10% FBS, 1% PS and 55 μM β-Mer, seeded 1*10^5/200 μl cells into the anti-CD$_3$ pre-coated 96 well plate. Add dilutions of compounds into the cells and incubate at 37° C. &5% CO$_2$ for 24 hours. IL-2 in cell supernatant was detected by ELISA Kit (R&D, DY202). Fit the compound EC$_{50}$ in non-linear regression equation: Y=Bottom+(Top−Bottom)/(1+10^((Log EC50−X)*Hill-Slope)), X=compound concentration, Y=Activation %. Top and Bottom: Plateaus in same units as Y. Log EC$_{50}$: same log units as X. Activation fold: Top activation/DMSO control. Activation % at 100 nM: Activation of non-linear regression equation curve at the concentration of 100 nM/DMSO control*100%.

The data for Example B is shown in Table 4.

TABLE 4

| Example | EC$_{50}$ (nM) | Activation fold | Activation % at 100 nM |
|---|---|---|---|
| 1 | 452 | 17.7 | 416 |
| 2 | 326 | 5.3 | 234 |
| 3 | 174 | 7.8 | 370 |
| 4 | 200 | 3.5 | 211 |
| 9 | 476 | 7.7 | 206 |
| 10 | 1246 | 7.3 | 143 |
| 11 | 832 | 6.1 | 169 |
| 12 | 262 | 8.5 | 340 |
| 15 | 963 | 6.5 | 214 |
| 16 | 346 | 6.29 | 253 |
| 17 | 1204 | 8.2 | 159 |
| 18 | 123 | 6.9 | 355 |
| 21 | 132 | 10.1 | 520 |
| 23 | 294 | 24.5 | 931 |
| 24 | 512 | 25.6 | 679 |
| 29 | 446 | 8.5 | 292 |
| 30 | 682 | 11.0 | 244 |

Example C: Pharmacokinetic Profile Evaluation

Species and strain: CD-1 mice of SPF. Source: Sino-British SIPPR/BK Lab Animal Ltd, Shanghai. 3 mice were intravenously administrated with given compounds (Formulation: 5% DMSO+10% Solutol+85% Saline) or orally gavage administrated with given compounds (Formulation: 5% DMSO+10% Solutol+85% Saline). The blood samples were taken via cephalic vein at timepoints 0.083 h, 0.25 h, 0.5 h, 1 h, 2 h, 4 h, 8 h and 24 h after intravenous administration or at timepoints 0.25 h, 0.5 h, 1 h, 2 h, 4 h, 6 h, 8 h and 24 h after oral gavage administration, 30 μL/time point. Blood samples were placed in tubes containing K2-EDTA and stored on ice until centrifuged. The blood samples were centrifuged at 6800 g for 6 minutes at 2-8° C. within 1 h after collected and stored frozen at approximately −80° C. An aliquot of 10 μL plasma samples were protein precipitated with 200 μL MeOH in which contains 10 ng/mL Verapamil (IS). The mixture was vortexed for 1 min and centrifuged at 18000 g for 7 min. Transfer 180 μL supernatant to 96 well plates. An aliquot of 6 μL supernatant was injected for LC-MS/MS analysis by LC-MS/MS-04 (API4000) instrument. The analytical results were confirmed using quality control samples for intra-assay variation. The accuracy of >66.7% of the quality control samples should be between 80-120% of the known value(s). Standard set of parameters including Area Under the Curve (AUC(0-t) and AUC(0-∞)), elimination half-live (T1/2), maximum plasma concentration (Cmax), will be calculated using noncompartmental analysis modules in FDA certified pharmacokinetic program Phoenix WinNonlin 7.0 (Pharsight, USA).

The data for Example C is shown in Table 5:

TABLE 5

| Mouse PK profile after oral administration at 5 mg/kg | | | | |
|---|---|---|---|---|
| Example | T$_{1/2}$ (h) | Cmax (ng/mL) | AUC$_{0-t}$ (ng*h/mL) | AUC0$_{0-\infty}$ (ng*h/mL) |
| 1 | 1.46 | 1885 | 5975 | 6148 |
| 12 | 3.56 | 1096 | 5464 | 5942 |
| 23 | 3.51 | 1823 | 11970 | 12108 |
| 28 | 2.67 | 677 | 3413 | 3463 |
| Ex570 | 1.66 | 749 | 2395 | 2500 |

The mouse PK data of compounds disclosed herein demonstrated much improved PK properties, especially for the AUC$_{0-t}$ and AUC$_{0-\infty}$ as compared with an existing compound (Example 570,

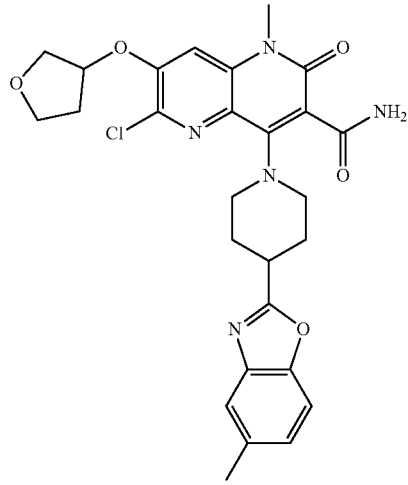 [SMILES: Cc1ccc2oc(C3CCN(c4c(C(N)=O)c(=O)n(C)c5cc(OC6CCOC6)c(Cl)nc45)CC3)nc2c1]

in WO2021105117).

What is claimed is:

1. A compound of Formula (If), or a pharmaceutically acceptable salt thereof:

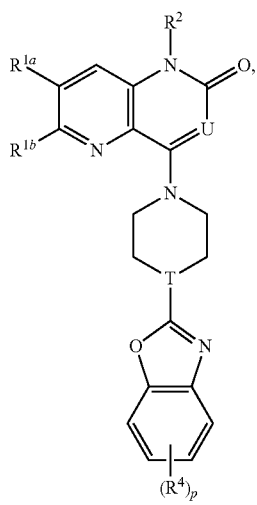

Formula (If)

wherein:
each $R^{1a}$ and $R^{1b}$ is independently halogen, —CN, —OR$^a$, or —NR$^c$R$^d$,
$R^2$ is $C_1$-$C_6$alkyl;
U is N or CH;
T is CH;
each $R^4$ is independently halogen or $C_1$-$C_6$alkyl;
p is 1 or 2;
each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, $C_1$-$C_6$alkylene(cycloalkyl), or $C_1$-$C_6$alkylene(heterocycloalkyl), wherein each alkyl, alkylene, cycloalkyl, and heterocycloalkyl is independently optionally substituted with one or more R;
$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, $C_1$-$C_6$alkylene(cycloalkyl), $C_1$-$C_6$alkylene(heterocycloalkyl), wherein each alkyl, alkylene, cycloalkyl, and heterocycloalkyl is independently optionally substituted with one or more R;
or $R^c$ and $R^d$ are taken together with the atom to which they are attached to form a heterocycloalkyl optionally substituted with one or more R; and
each R is independently halogen, —CN, —OH, —S(═O)CH$_3$, —S(═O)$_2$CH$_3$, —S(═O)$_2$NH$_2$, —S(═O)$_2$NHCH$_3$, —S(═O)$_2$N(CH$_3$)$_2$, —NH$_2$, —NHCH$_3$, —N(CH$_3$)$_2$, —C(═O)CH$_3$, —C(═O)OH, —C(═O)OCH$_3$, $C_1$-$C_6$alkyl, $C_1$-$C_6$alkoxy, $C_1$-$C_6$haloalkyl, $C_1$-$C_6$hydroxyalkyl, $C_1$-$C_6$aminoalkyl, $C_1$-$C_6$heteroalkyl, or $C_3$-$C_6$cycloalkyl;
or two R on the same atom form an oxo.

2. The compound of claim 1, or a pharmaceutically acceptable salt thereof, wherein each $R^{1a}$ and $R^{1b}$ is independently halogen, —CN, —O-heterocycloalkyl, —O—$C_1$-$C_6$alkyl, —O—$C_1$-$C_6$haloalkyl, —O—$C_1$-$C_6$hydroxylalkyl, —O—$C_1$-$C_6$aminoalkyl, or —NH—$C_1$-$C_6$hydroxylalkyl.

3. The compound of claim 1, or a pharmaceutically acceptable salt thereof, wherein each $R^{1a}$ and $R^{1b}$ is independently —CN, —O-heterocycloalkyl, —O—$C_1$-$C_6$alkyl, —O—$C_1$-$C_6$haloalkyl, —O—$C_1$-$C_6$hydroxylalkyl, or —O—$C_1$-$C_6$aminoalkyl.

4. The compound of claim 1, or a pharmaceutically acceptable salt thereof, wherein each $R^{1a}$ and $R^{1b}$ are independently —CN or —O—$C_1$-$C_6$hydroxylalkyl.

5. The compound of claim 1, wherein the compound is selected from the group consisting of:

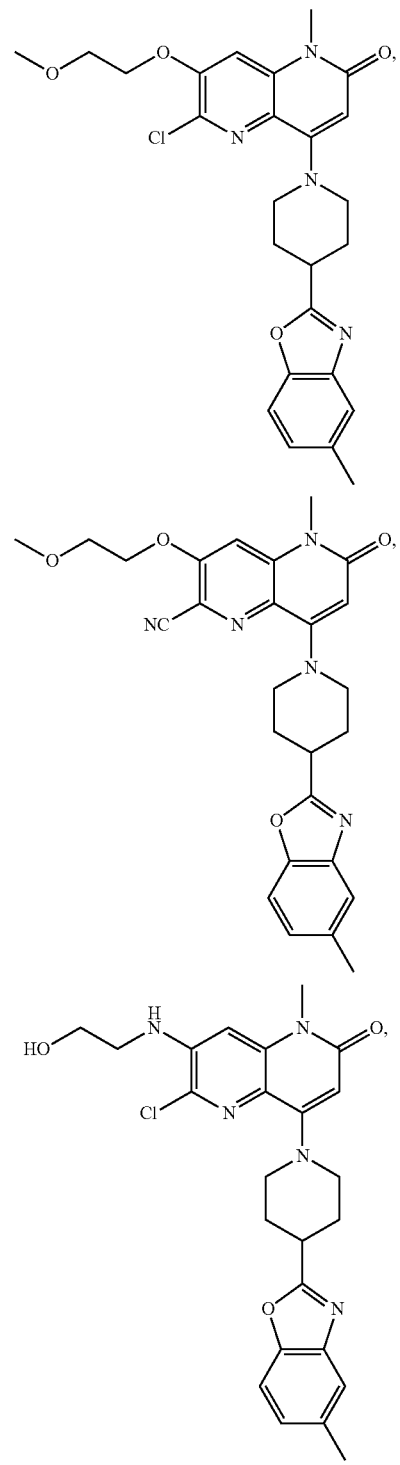

129
-continued
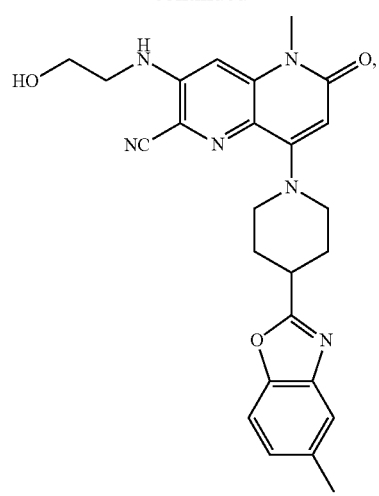
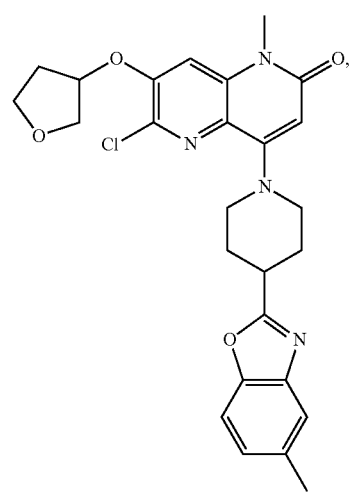
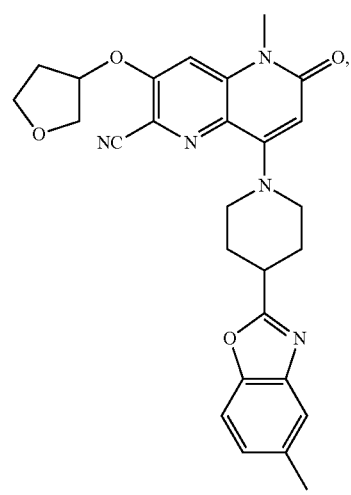
130
-continued
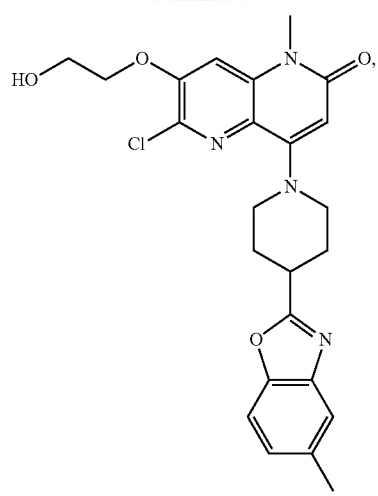
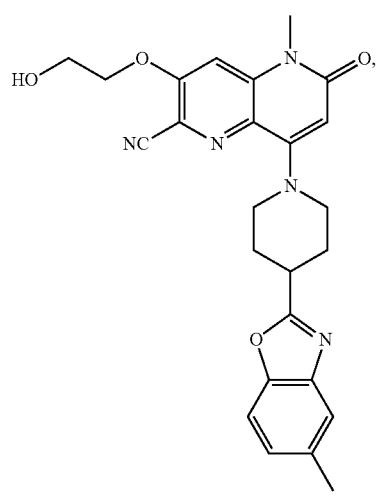
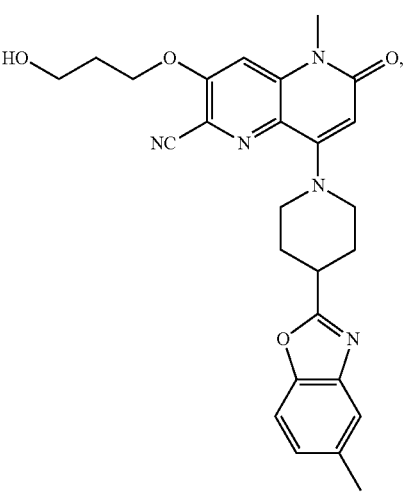

131
-continued
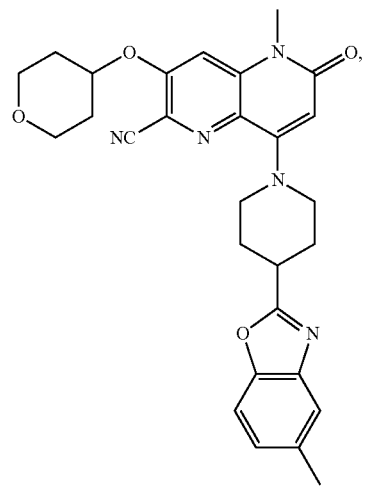
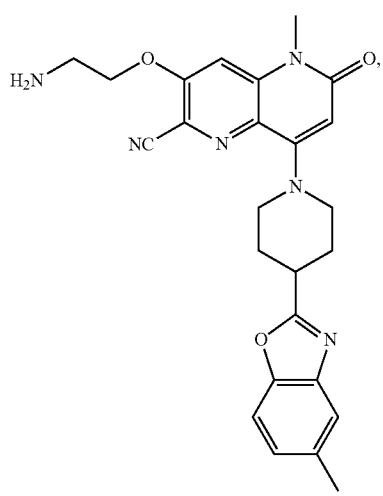
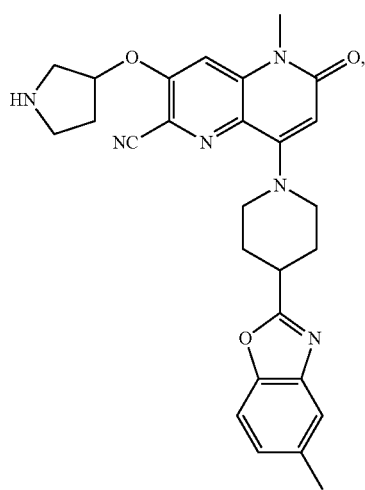
132
-continued
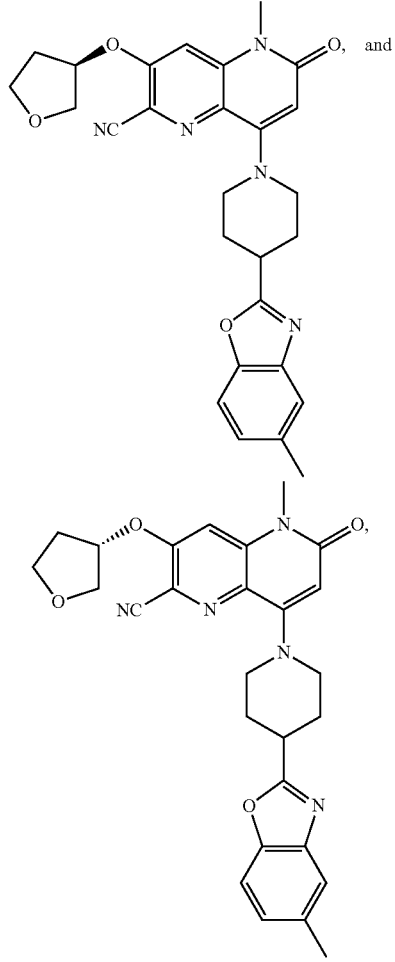
or a pharmaceutically acceptable salt thereof.
6. The compound of claim 1 that is
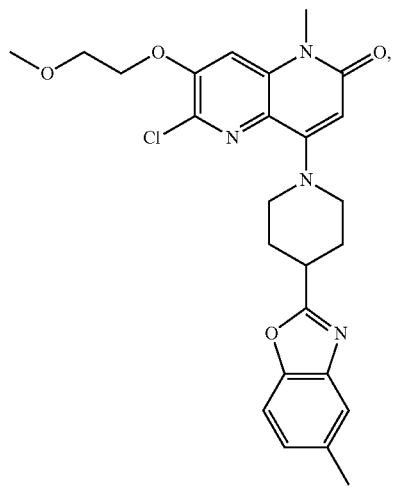 [SMILES: COCCOc1cc2c(nc1Cl)c(N1CCC(c3nc4cc(C)ccc4o3)CC1)cc(=O)n2C]
or a pharmaceutically acceptable salt thereof.

7. The compound of claim 1 that is

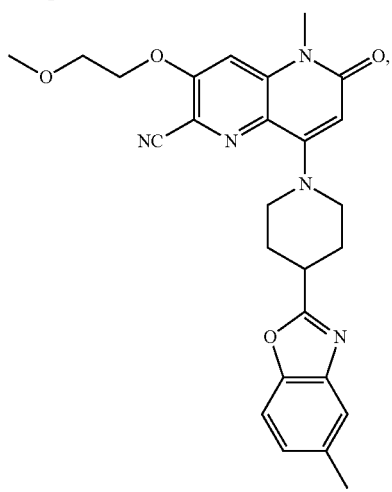 [SMILES: COCCOc1cc2c(nc1C#N)c(N1CCC(c3nc4cc(C)ccc4o3)CC1)cc(=O)n2C]

or a pharmaceutically acceptable salt thereof.

8. The compound of claim 1 that is

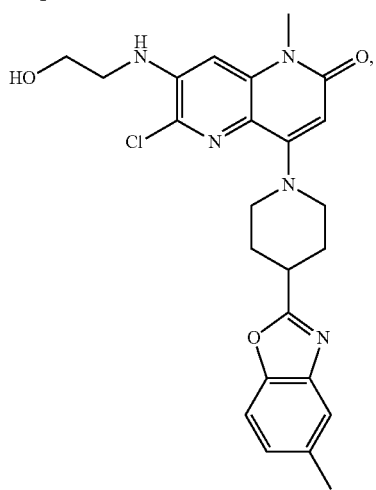

or a pharmaceutically acceptable salt thereof.

9. The compound of claim 1 that is

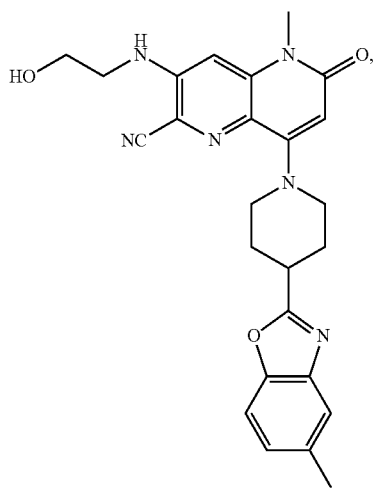 [SMILES: Cc1ccc2oc(C3CCN(c4cc(=O)n(C)c5cc(NCCO)c(C#N)nc45)CC3)nc2c1]

or a pharmaceutically acceptable salt thereof.

10. The compound of claim 1 that is

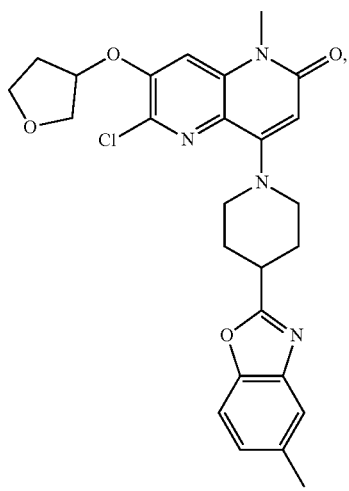 [SMILES: Cc1ccc2oc(C3CCN(c4cc(=O)n(C)c5cc(OC6CCOC6)c(Cl)nc45)CC3)nc2c1]

or a pharmaceutically acceptable salt thereof.

11. The compound of claim 1 that is

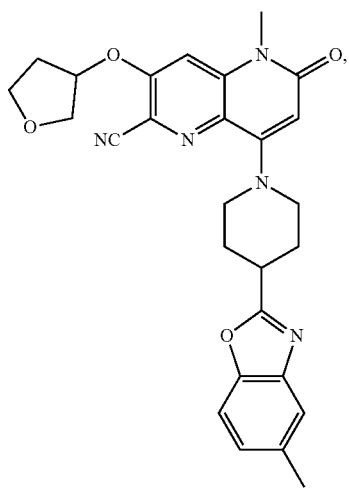 [SMILES: Cc1ccc2oc(C3CCN(c4cc(=O)n(C)c5cc(OC6CCOC6)c(C#N)nc45)CC3)nc2c1]

or a pharmaceutically acceptable salt thereof.

12. The compound of claim 1 that is
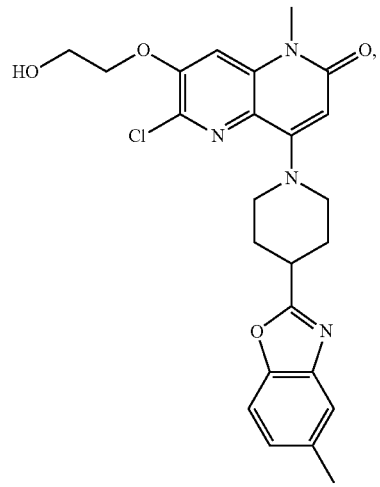
or a pharmaceutically acceptable salt thereof.
13. The compound of claim 1 that is
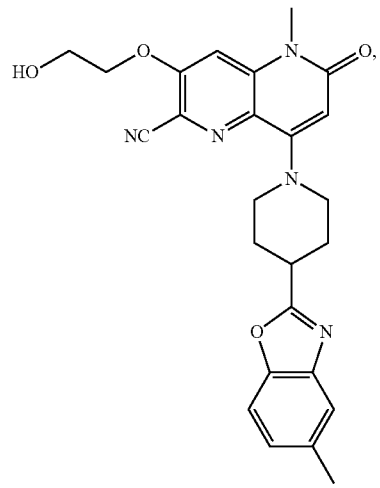
or a pharmaceutically acceptable salt thereof.
14. The compound of claim 1 that is
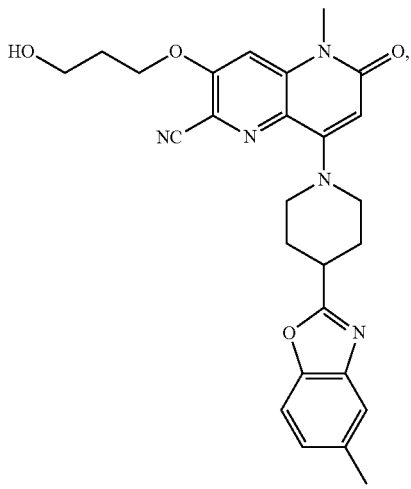 [SMILES: Cc1ccc2oc(C3CCN(c4cc(=O)n(C)c5cc(OCCCO)c(C#N)nc45)CC3)nc2c1]
or a pharmaceutically acceptable salt thereof.
15. The compound of claim 1 that is
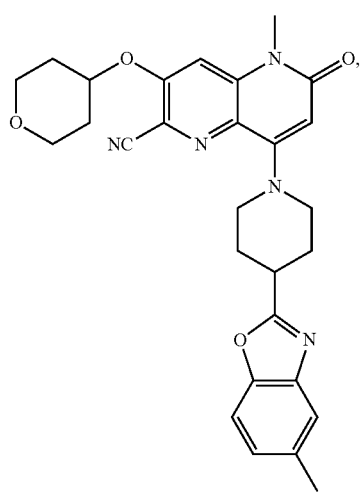 [SMILES: Cc1ccc2oc(C3CCN(c4cc(=O)n(C)c5cc(OC6CCOCC6)c(C#N)nc45)CC3)nc2c1]
or a pharmaceutically acceptable salt thereof.

16. The compound of claim 1 that is

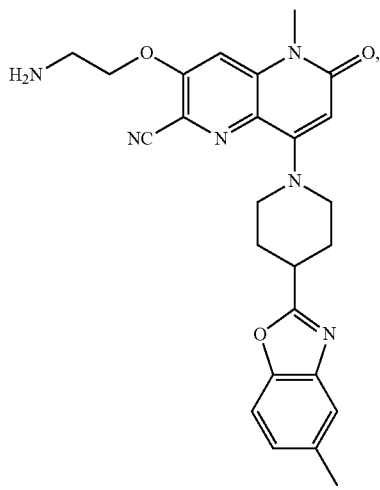 [SMILES: Cc1ccc2oc(C3CCN(c4cc(=O)n(C)c5cc(OCCN)c(C#N)nc45)CC3)nc2c1]

or a pharmaceutically acceptable salt thereof.

17. The compound of claim 1 that is

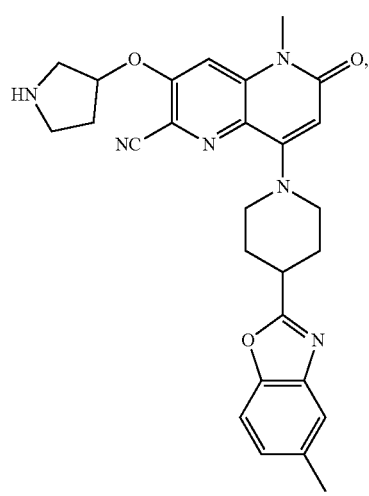 [SMILES: Cc1ccc2oc(C3CCN(c4cc(=O)n(C)c5cc(OC6CCNC6)c(C#N)nc45)CC3)nc2c1]

or a pharmaceutically acceptable salt thereof.

18. The compound of claim 1 that is

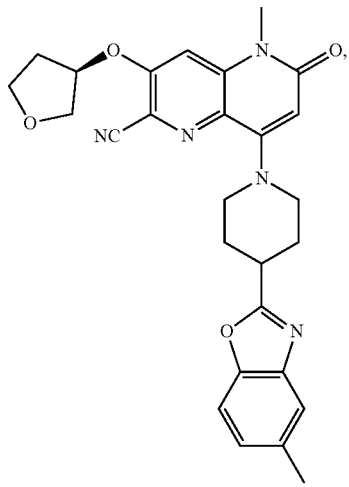 [SMILES: Cc1ccc2oc(C3CCN(c4cc(=O)n(C)c5cc(O[C@@H]6CCOC6)c(C#N)nc45)CC3)nc2c1]

or a pharmaceutically acceptable salt thereof.

19. The compound of claim 1 that is

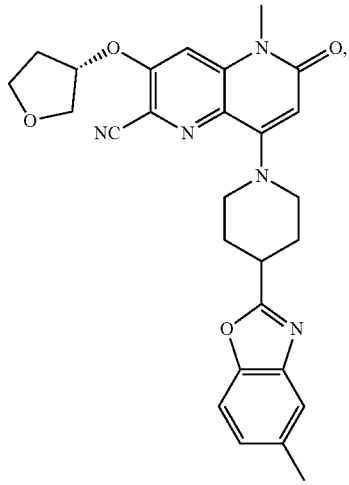 [SMILES: Cc1ccc2oc(C3CCN(c4cc(=O)n(C)c5cc(O[C@H]6CCOC6)c(C#N)nc45)CC3)nc2c1]

or a pharmaceutically acceptable salt thereof.

20. A pharmaceutical composition comprising the compound of claim 1, or a pharmaceutically acceptable salt thereof, and a pharmaceutically acceptable excipient.

* * * * *

UNITED STATES PATENT AND TRADEMARK OFFICE
CERTIFICATE OF CORRECTION

| | |
|---|---|
| PATENT NO. | : 12,077,538 B2 |
| APPLICATION NO. | : 18/507595 |
| DATED | : September 3, 2024 |
| INVENTOR(S) | : Hongfu Lu et al. |

It is certified that error appears in the above-identified patent and that said Letters Patent is hereby corrected as shown below:

In the Claims

Claim 1, Lines 52-53 replace:
"each R is independently halogen, —CN, —OH, —S(—O)CH$_3$"
With:
--each R is independently halogen, —CN, —OH, —S(=O)CH$_3$--

Signed and Sealed this
Eighth Day of October, 2024

*Katherine Kelly Vidal*

Katherine Kelly Vidal
*Director of the United States Patent and Trademark Office*